United States Patent [19]
Kozlowski

[11] Patent Number: 5,152,751
[45] Date of Patent: Oct. 6, 1992

[54] HYPODERMIC NEEDLE SAFETY SHIELD

[76] Inventor: David J. Kozlowski, 560 Hoover St., Napa, Calif. 94559

[21] Appl. No.: 621,642

[22] Filed: Dec. 4, 1990

[51] Int. Cl.⁵ .............................................. A61M 5/32
[52] U.S. Cl. .................................. 604/192; 604/198; 604/263
[58] Field of Search .............. 604/192, 198, 187, 263, 604/197, 110, 171, 195, 196, 233, 234, 223, 111

[56] References Cited

U.S. PATENT DOCUMENTS

| | | | |
|---|---|---|---|
| 4,040,421 | 8/1977 | Young | 128/218 |
| 4,194,505 | 3/1980 | Schmitz | 604/196 |
| 4,573,976 | 3/1986 | Sampson et al. | 604/263 |
| 4,813,940 | 3/1989 | Parry | 604/198 |
| 4,816,022 | 3/1989 | Poncy | 604/198 |
| 4,820,277 | 4/1989 | Norelli | 604/192 |
| 4,826,484 | 5/1989 | Haber | 604/110 |
| 4,826,488 | 5/1989 | Nelson | 604/192 |
| 4,826,489 | 5/1989 | Haber | 604/195 |
| 4,826,490 | 5/1989 | Byrne | 604/195 |
| 4,826,491 | 5/1989 | Schramm | 604/198 |
| 4,838,869 | 6/1989 | Allard | 604/195 |
| 4,838,871 | 6/1989 | Luther | 604/192 |
| 4,842,587 | 6/1989 | Poncy | 604/198 |
| 4,863,435 | 9/1989 | Sturman | 604/198 |
| 4,872,552 | 10/1989 | Unger | 206/365 |
| 4,883,469 | 11/1989 | Glazier | 604/192 |
| 4,915,696 | 4/1990 | Feimer | 604/192 |
| 4,923,447 | 5/1990 | Morgan | 604/198 |
| 4,946,447 | 8/1990 | Hardcastle | 604/198 |
| 4,994,034 | 2/1991 | Botich et al. | 604/198 |
| 4,994,046 | 2/1991 | Wesson et al. | 604/109 |
| 5,000,740 | 3/1991 | Ducharme et al. | 604/198 |
| 5,026,356 | 6/1991 | Smith | 604/198 |
| 5,030,209 | 7/1991 | Wonderer et al. | 604/198 |
| 5,053,014 | 10/1991 | Van Mengten | 604/198 |

Primary Examiner—C. Fred Rosenbaum
Assistant Examiner—Chalin Smith

[57] ABSTRACT

A manually operated needle-shielding safety device attachable to a standard hypodermic needle and syringe medical apparatus (42). By forward directed thumb or finger stroke upon a proximally projecting pushrod (128) slidably operable within a pushrod channel (82) positioned parallel to and radially removed from the primary syringe barrel plunger (44), the elongated shield (148) is pushed from a housing (66) mounted at the base of the hypodermic needle and syringe apparatus (42), rotated longitudinally from an inverted position, and advanced to the distal end of the syringe apparatus (42) against resistance from a rubber band (64) or integral expansion spring (244). The distal portion of the shield (148) surmounts the tip of the needle (54) and the needle (54) enters the shield (148) laterally through an opening in the shield face (154). The operator then releases thumb or finger pressure upon the pushrod (128) and the enclosed forward end of the shield (148) is pulled rearward by the rubber band (64) or integral expansion spring (244) to surround and safely contain the needle (54) tip.

The device can be deployed quickly, surely, and conveniently at the user's option immediately after the injection process, with one hand, without the need to shift finger grip upon the hypodermic apparatus (42), and without interfering with the user's concentration upon other important medical tasks. The invention can be used with most currently manufactured needle and syringe devices and does not require modification of existing needle designs, needle hub designs including luer connection designs and low-dose minimum "dead space" designs, needle cementing processes and equipment, fluid chamber designs, and fluid chamber piston engines.

23 Claims, 35 Drawing Sheets

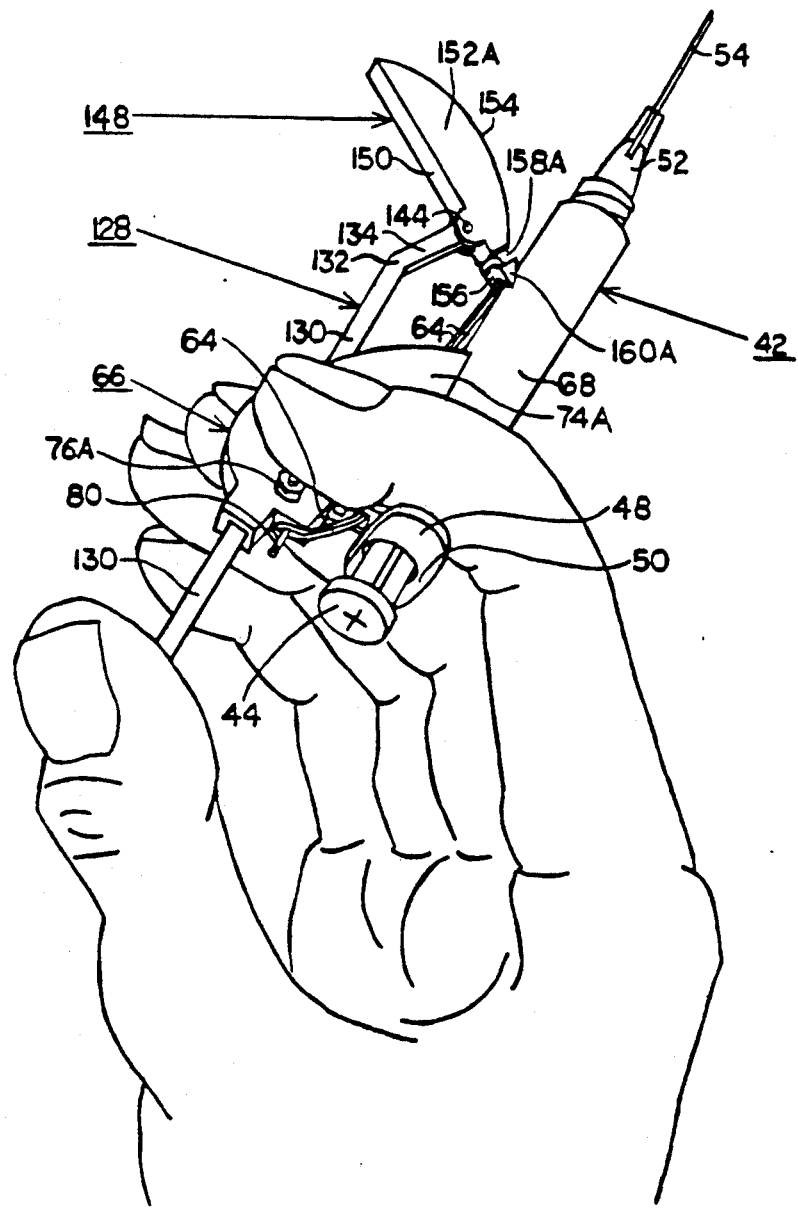
FIG. 1-A

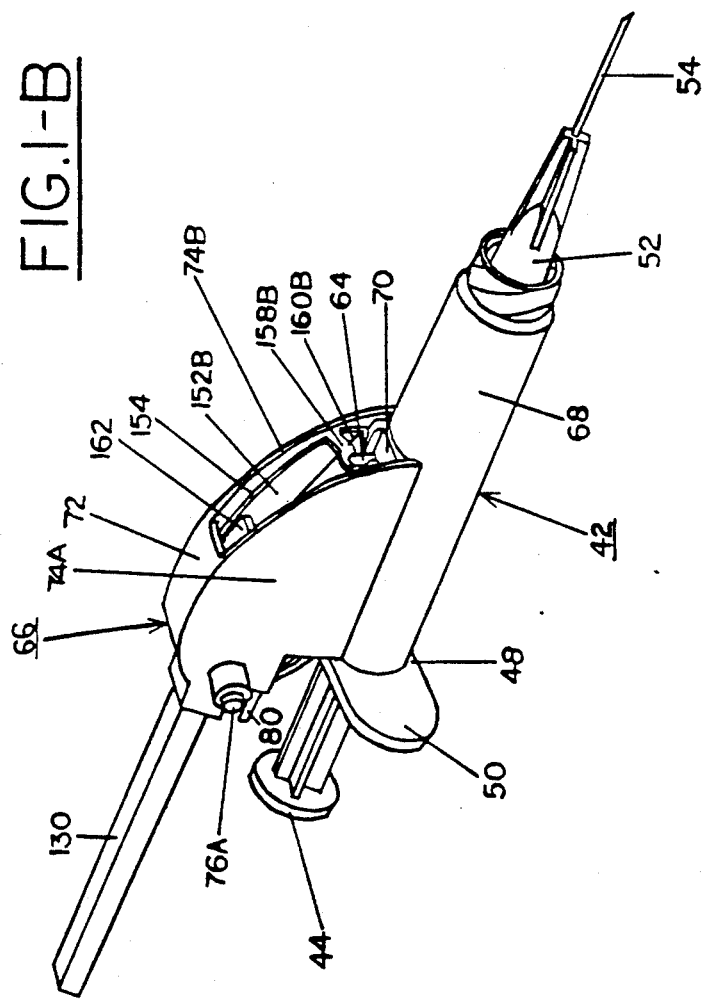

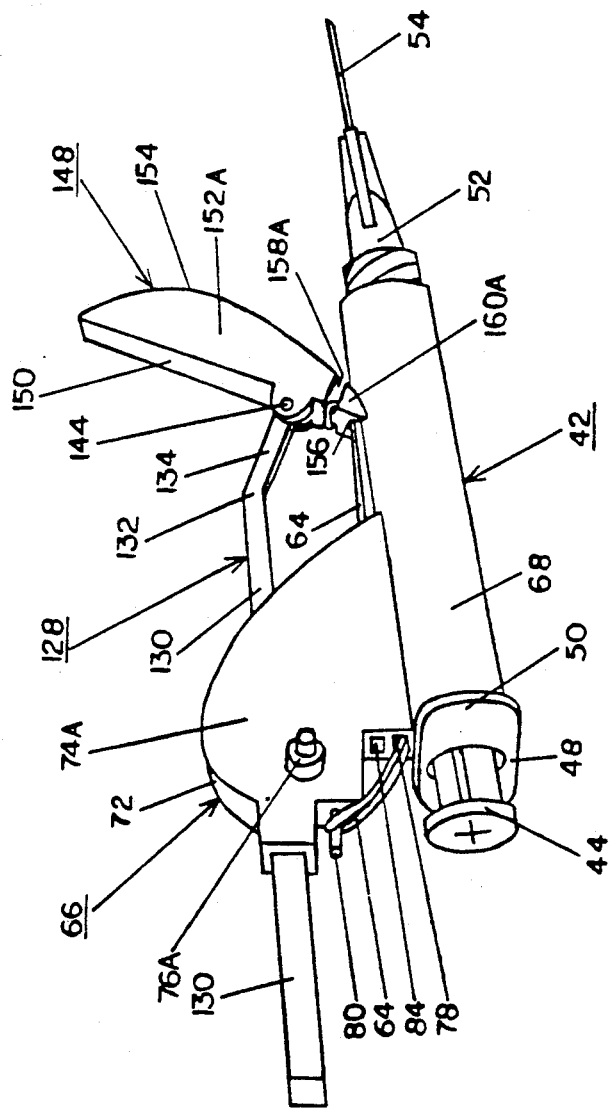
FIG.1-C

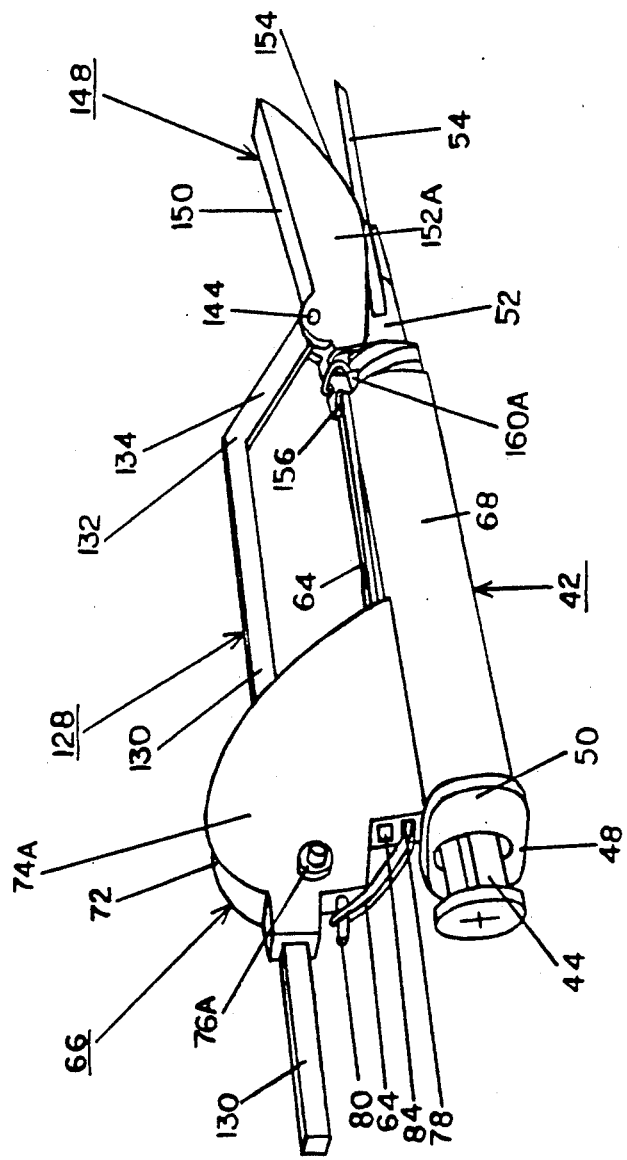

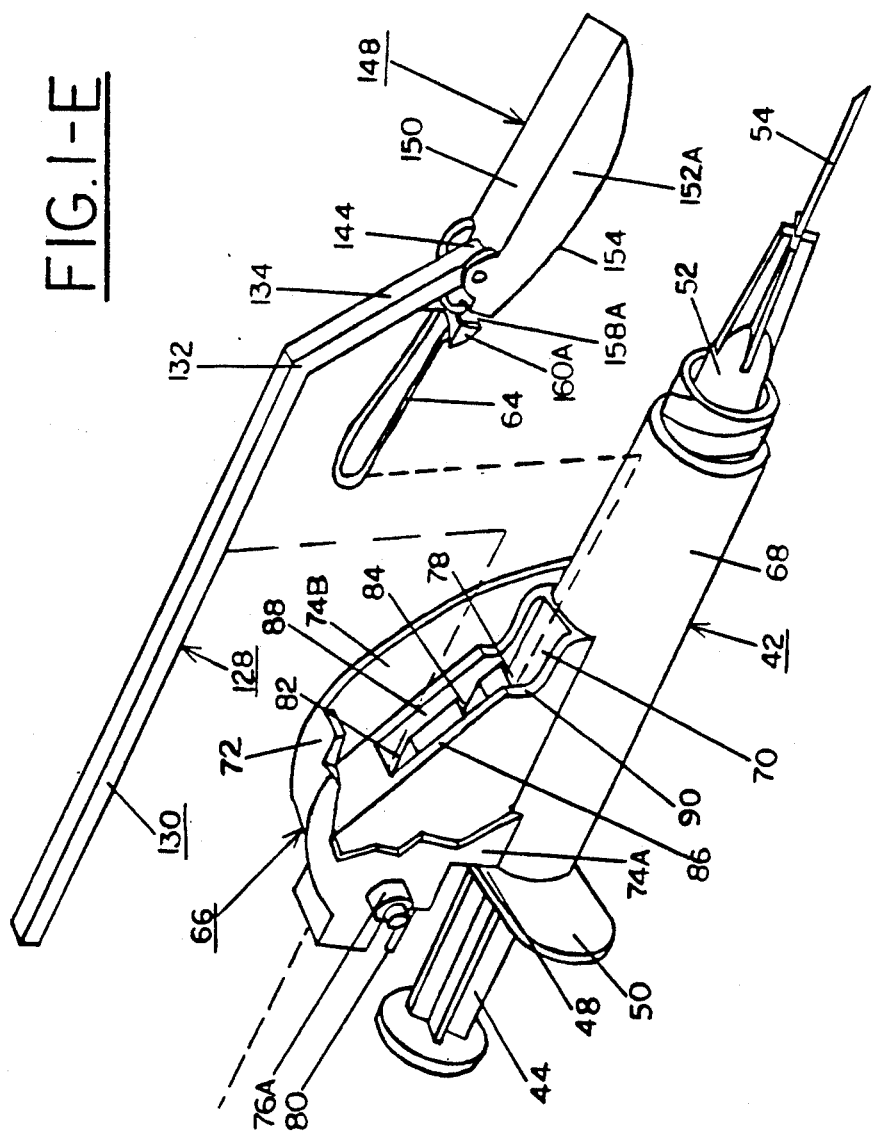

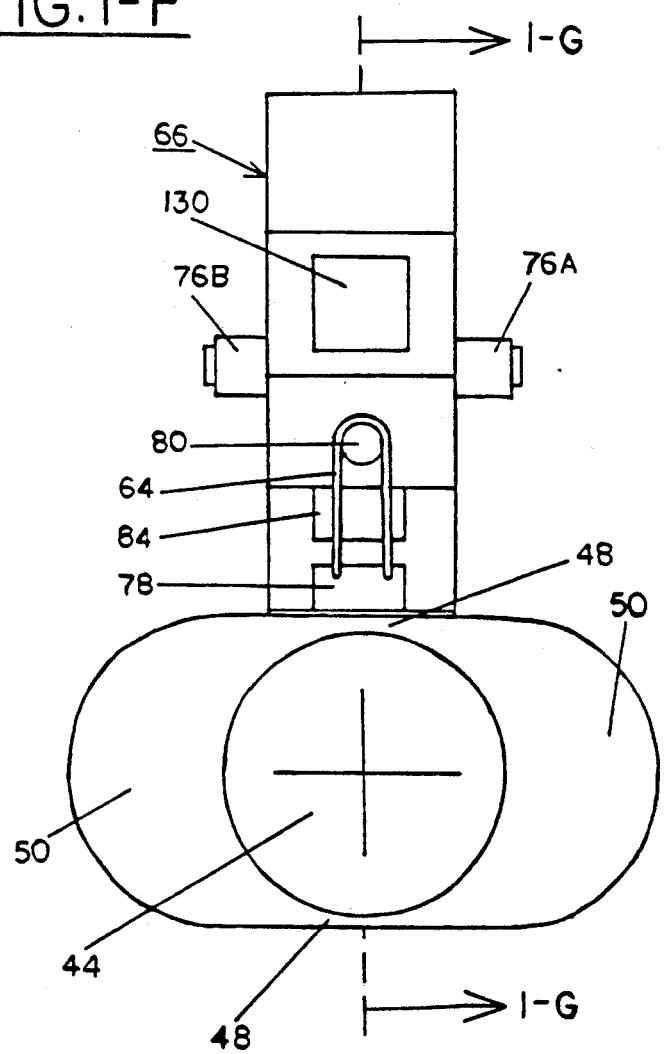

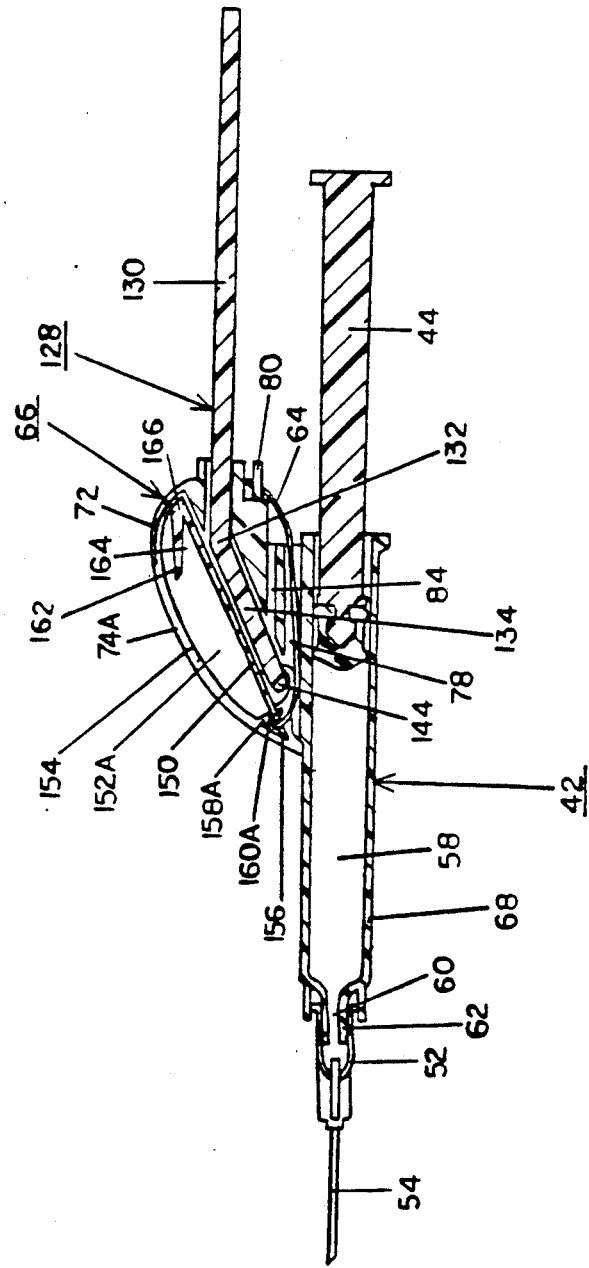

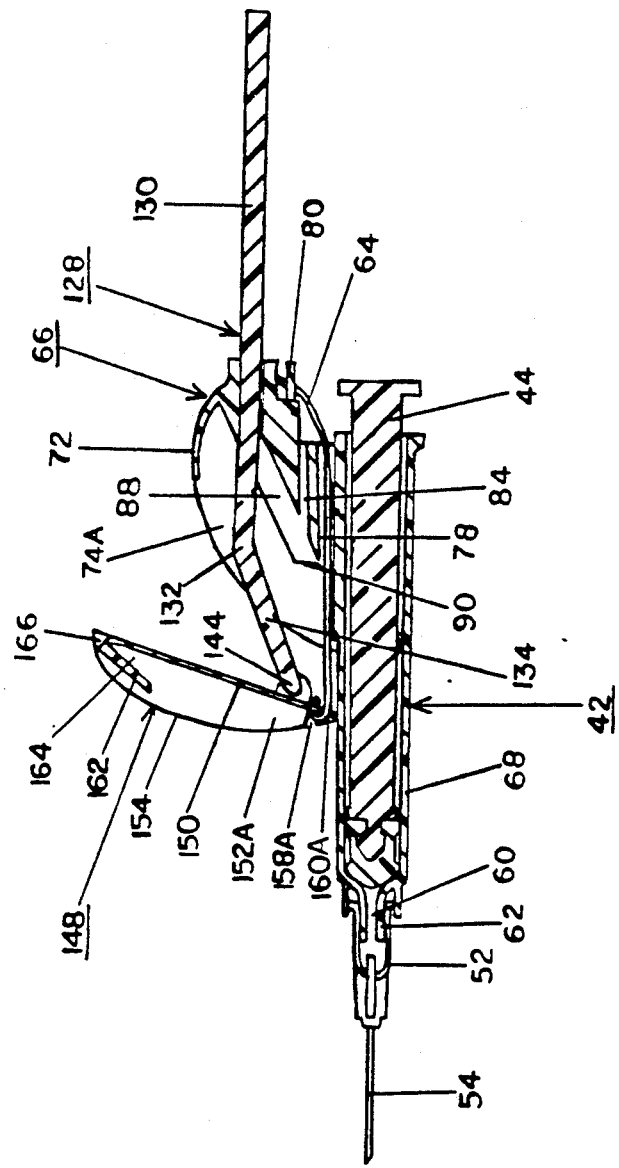

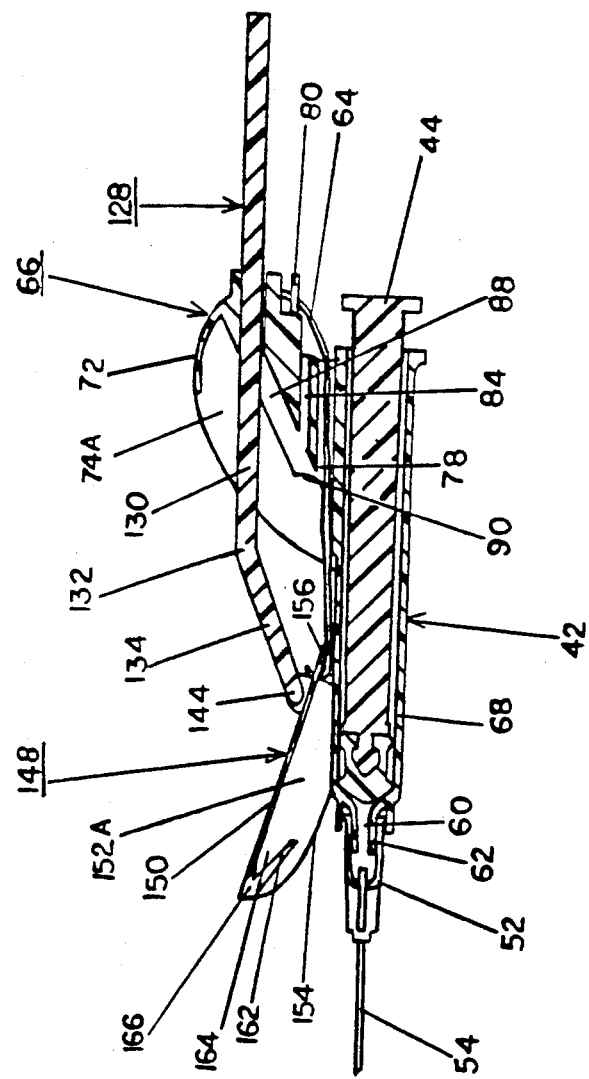

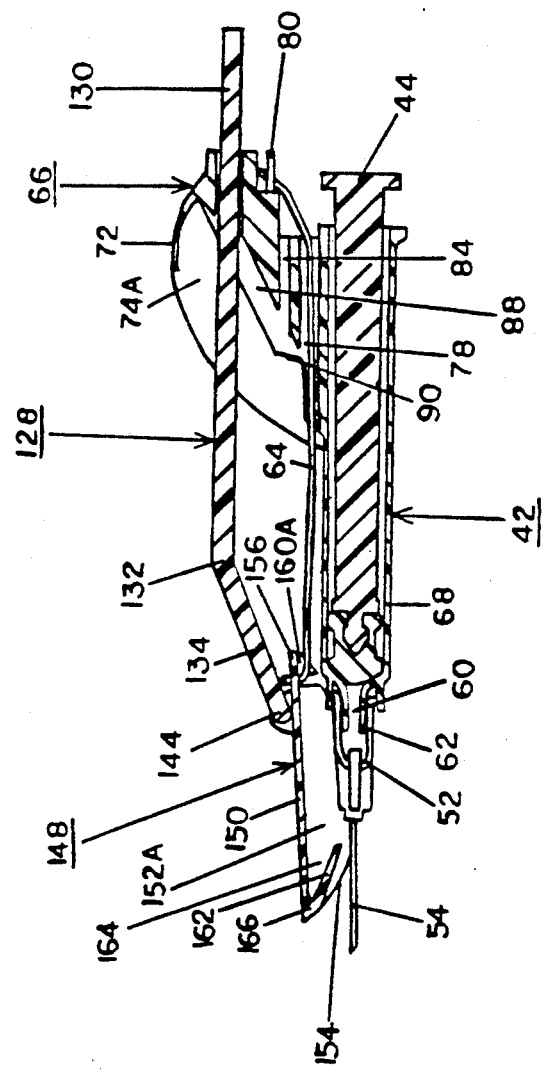

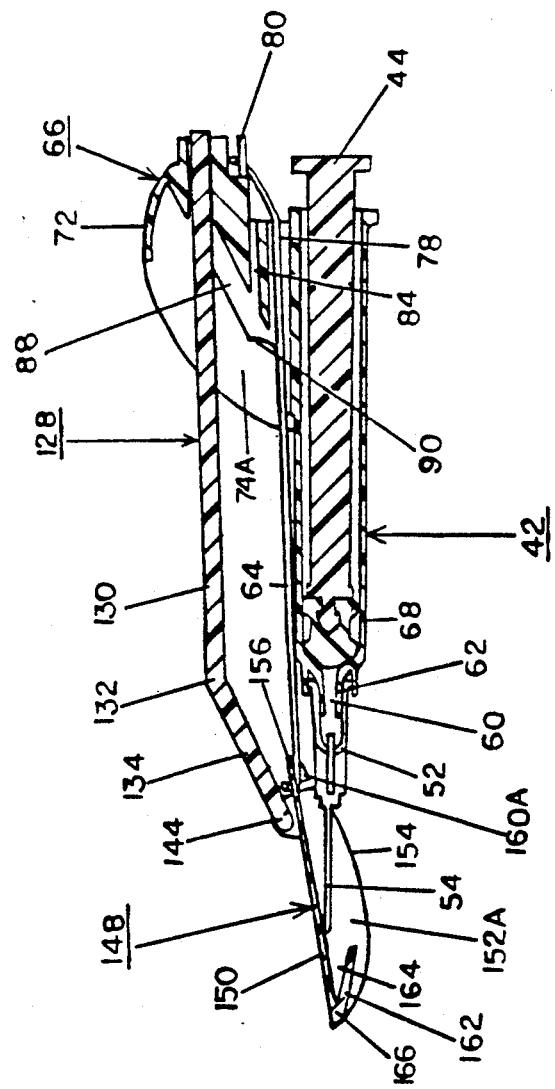

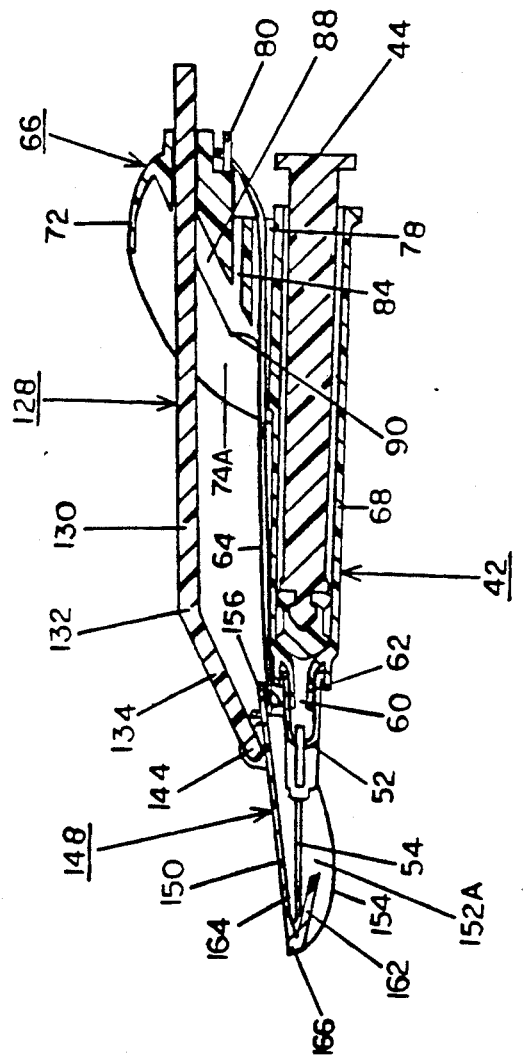
FIG.1-L

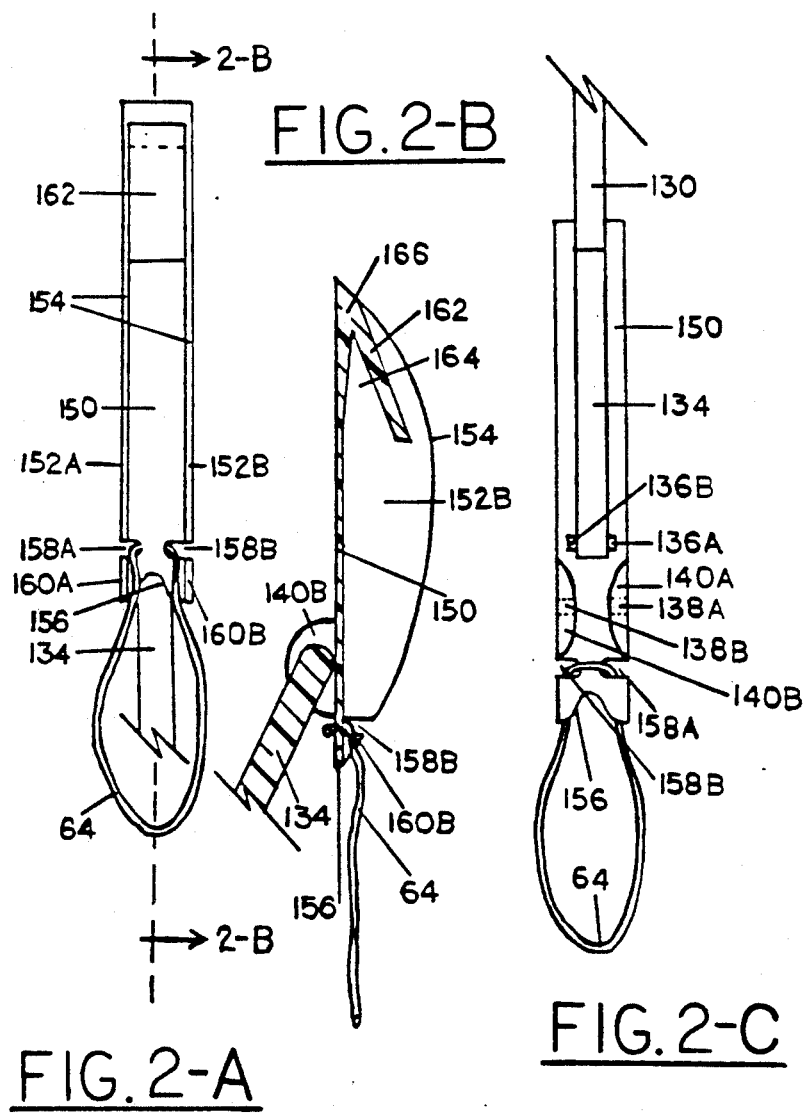

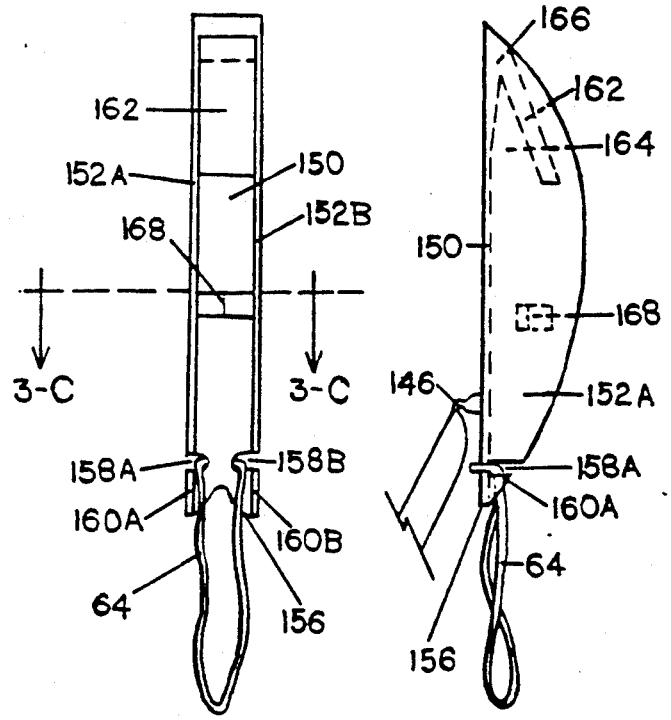

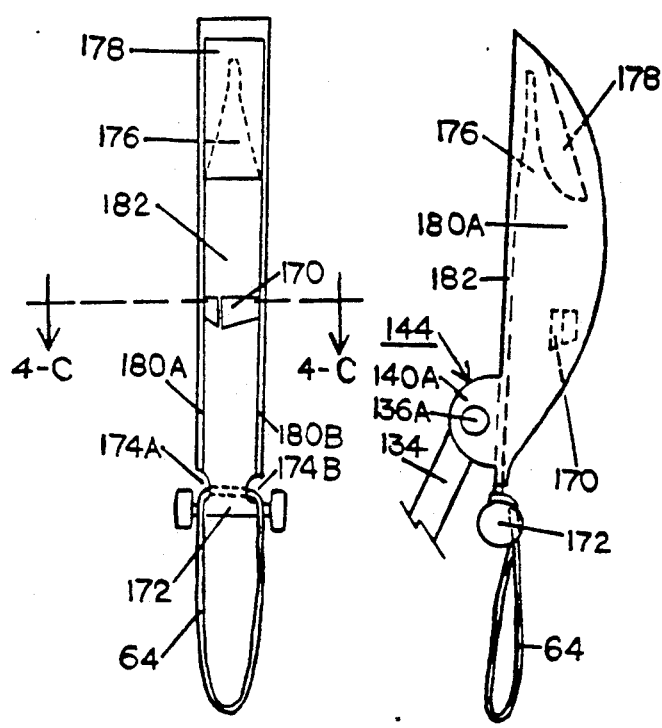
FIG.4-A  FIG.4-B
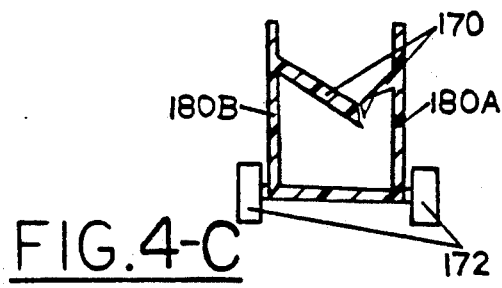
FIG.4-C

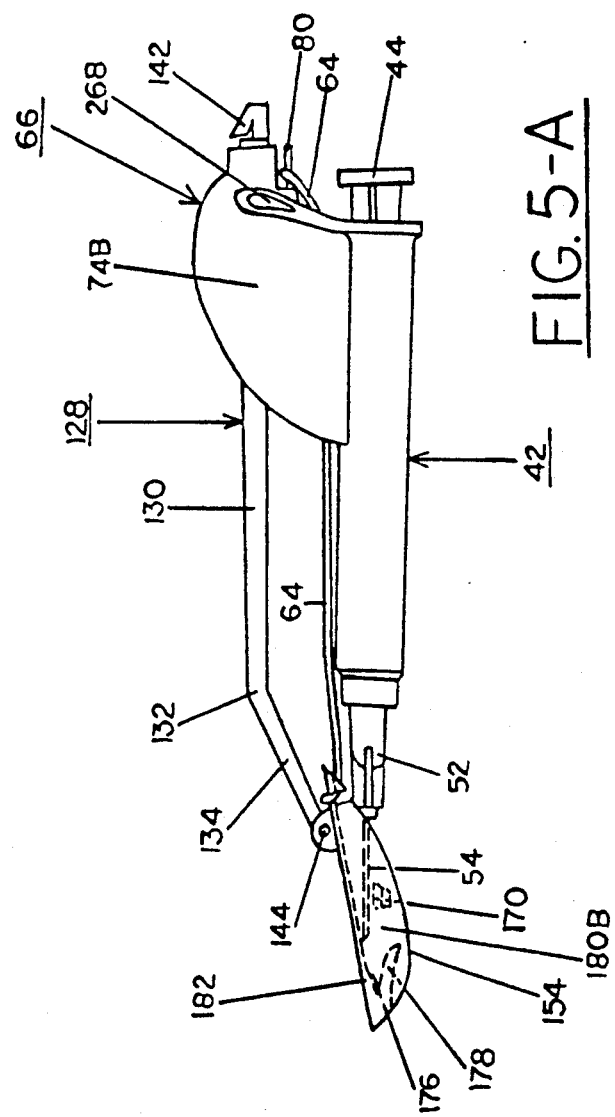

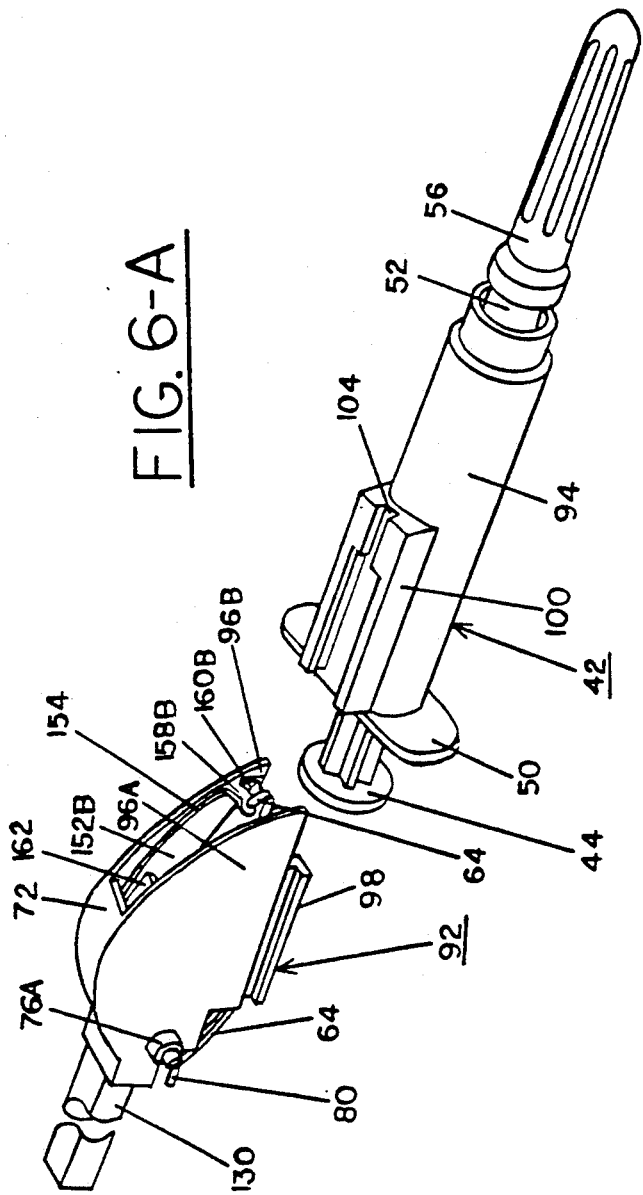

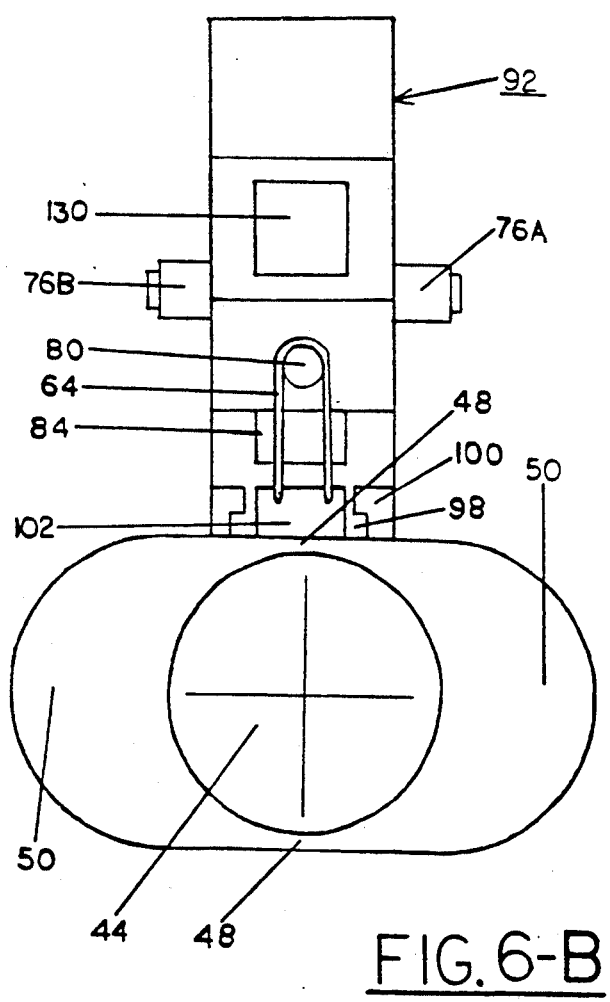
FIG. 6-B

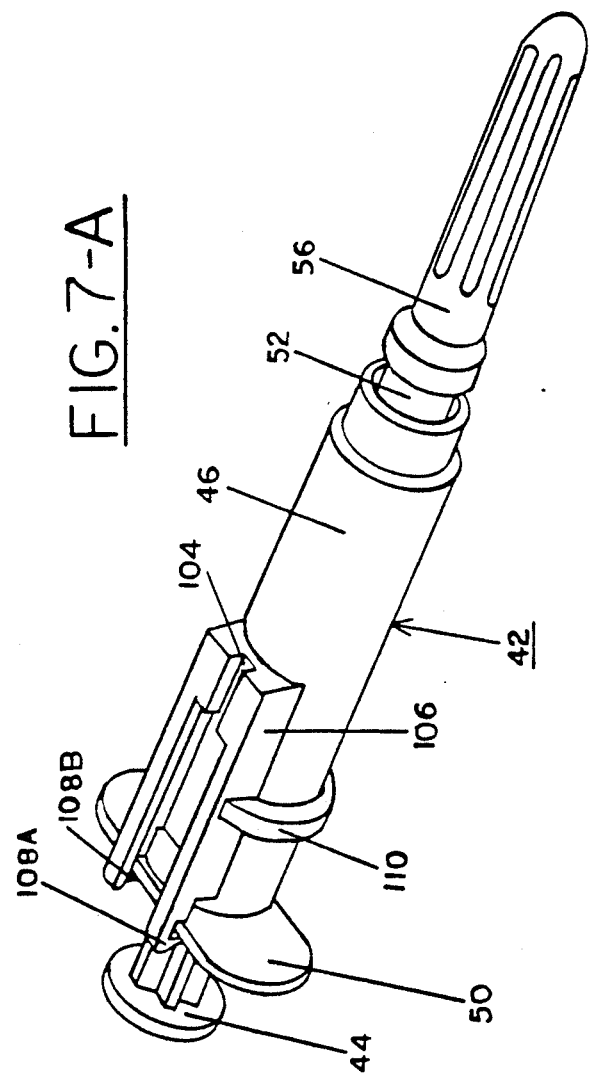

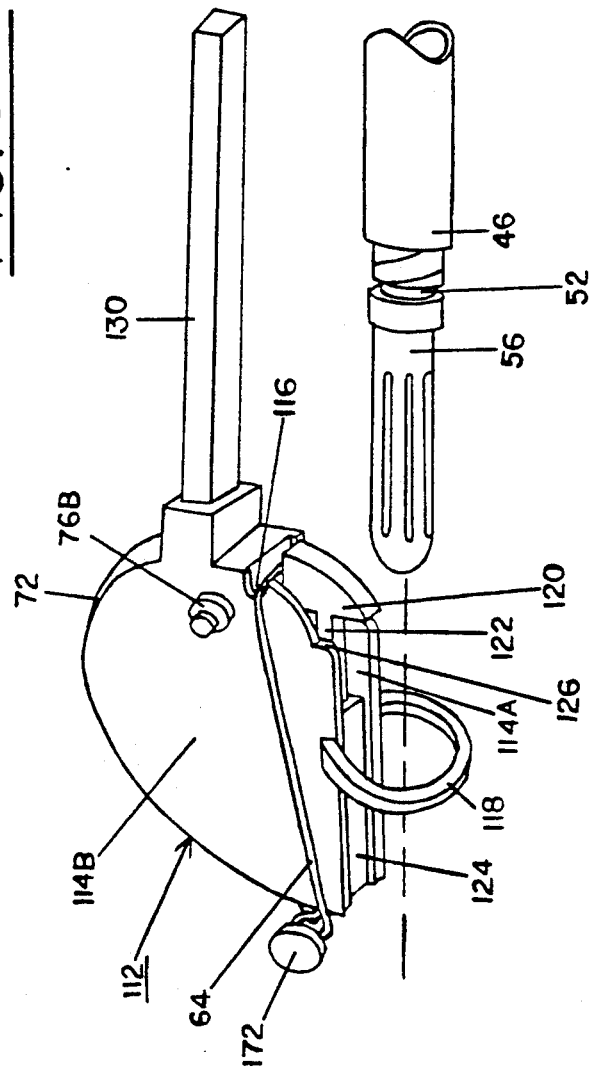

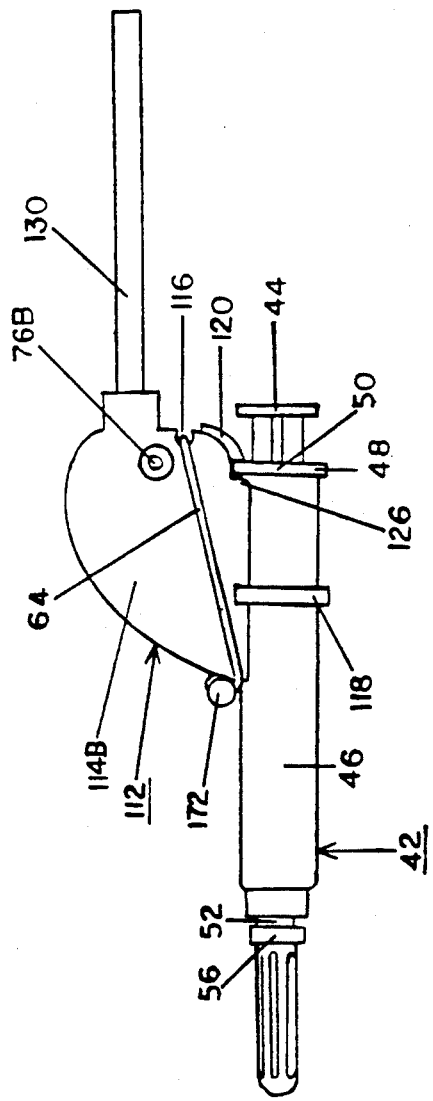
FIG. 8-B

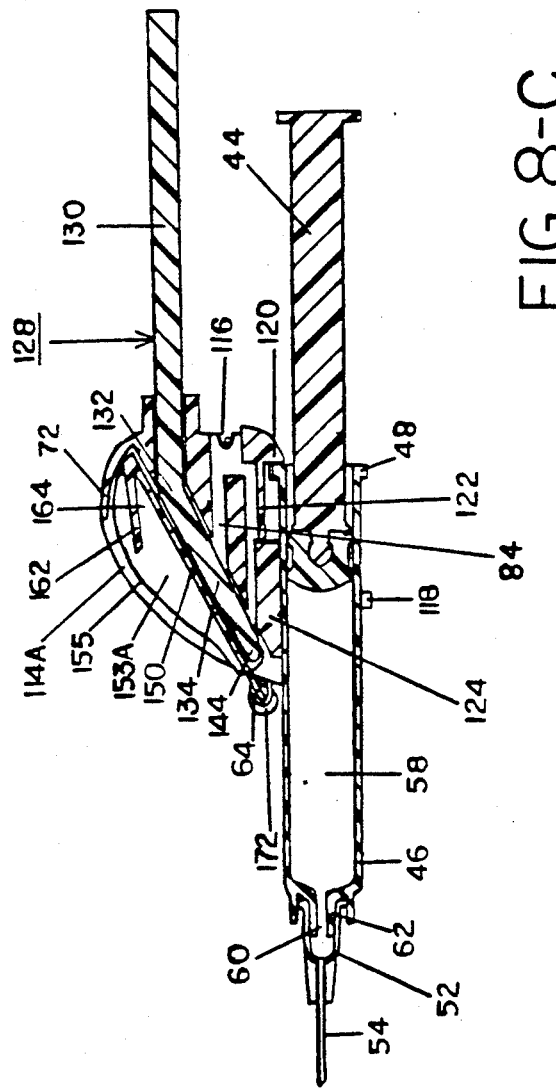

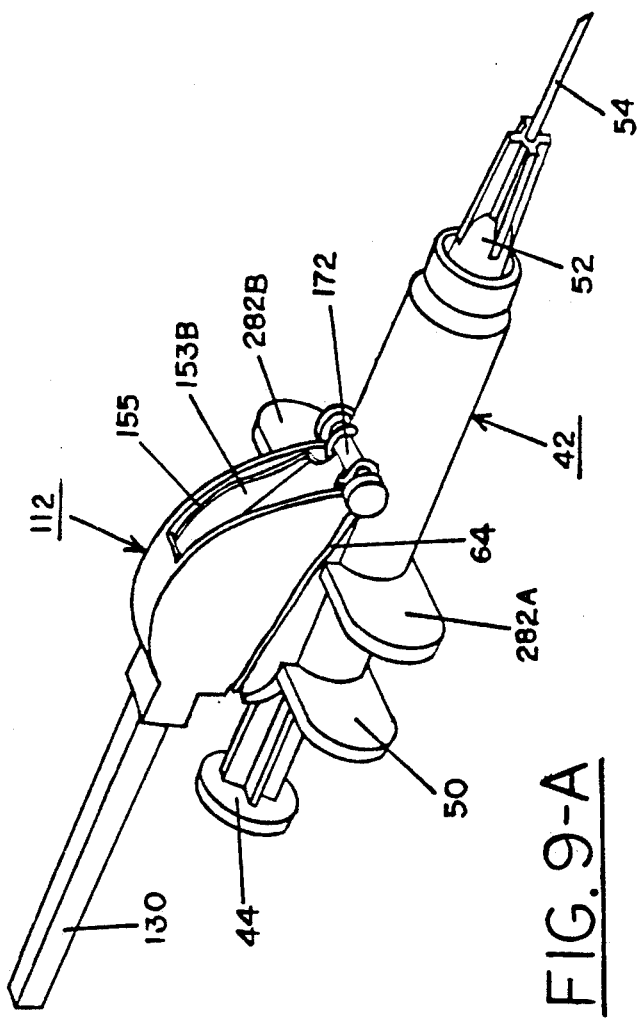
FIG. 9-A

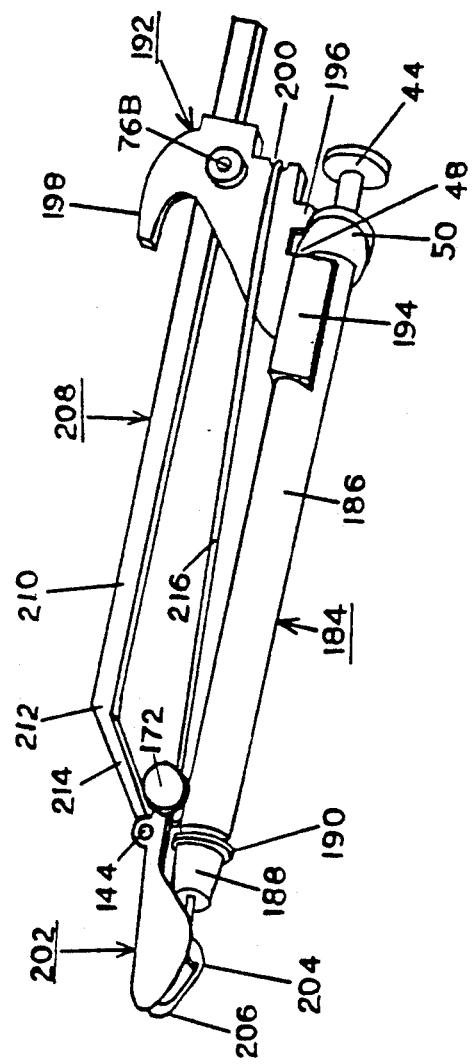

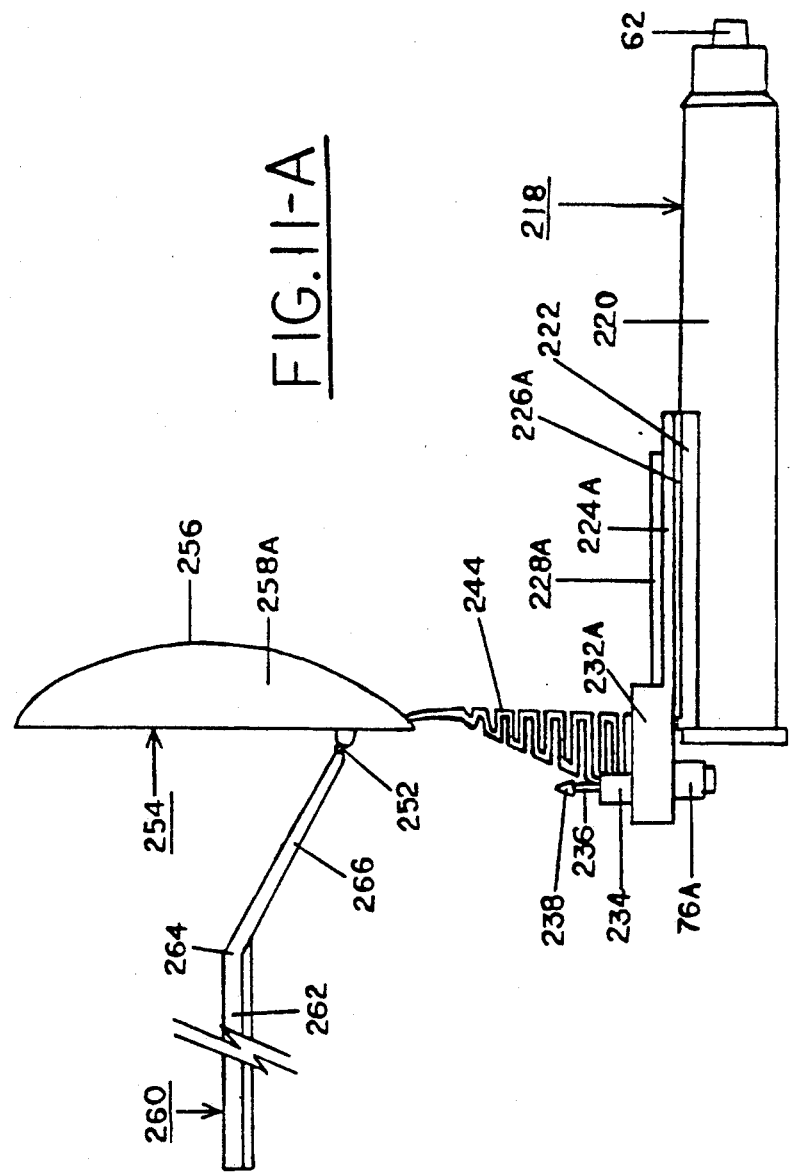
FIG.11-A

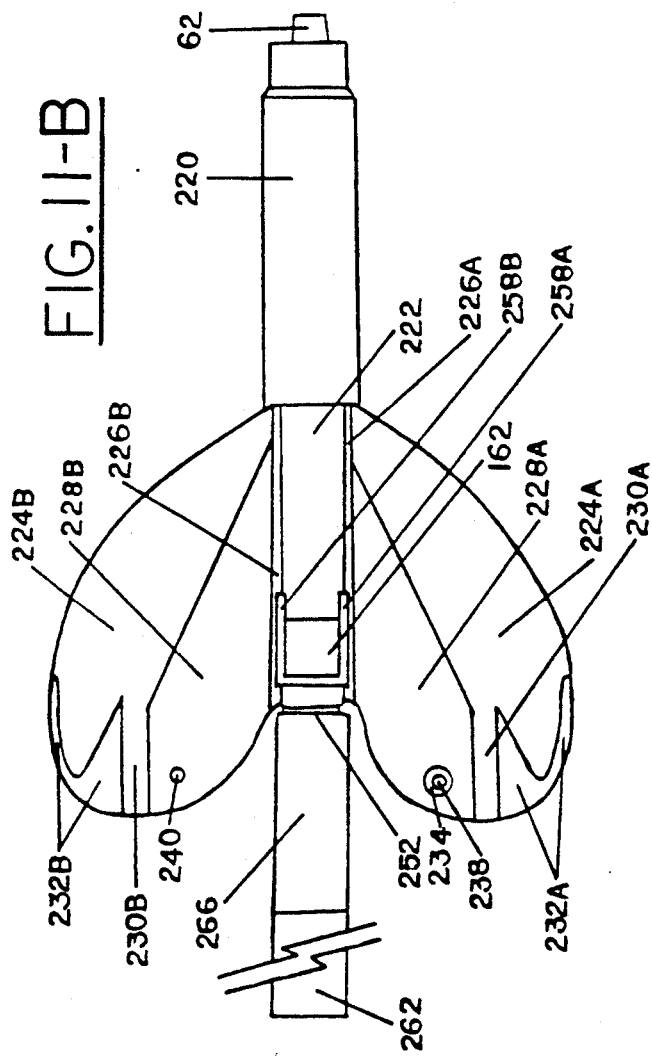

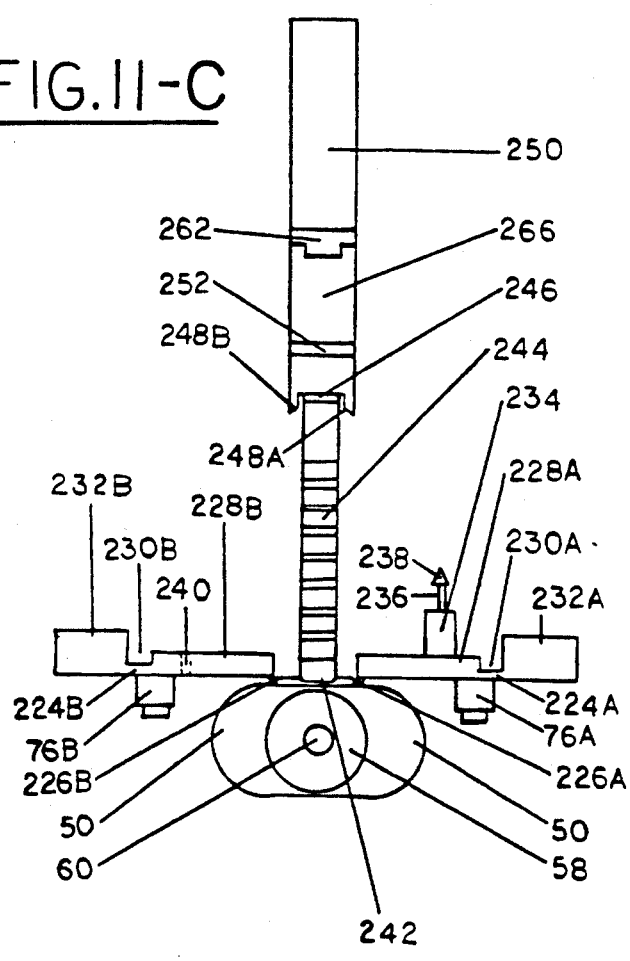

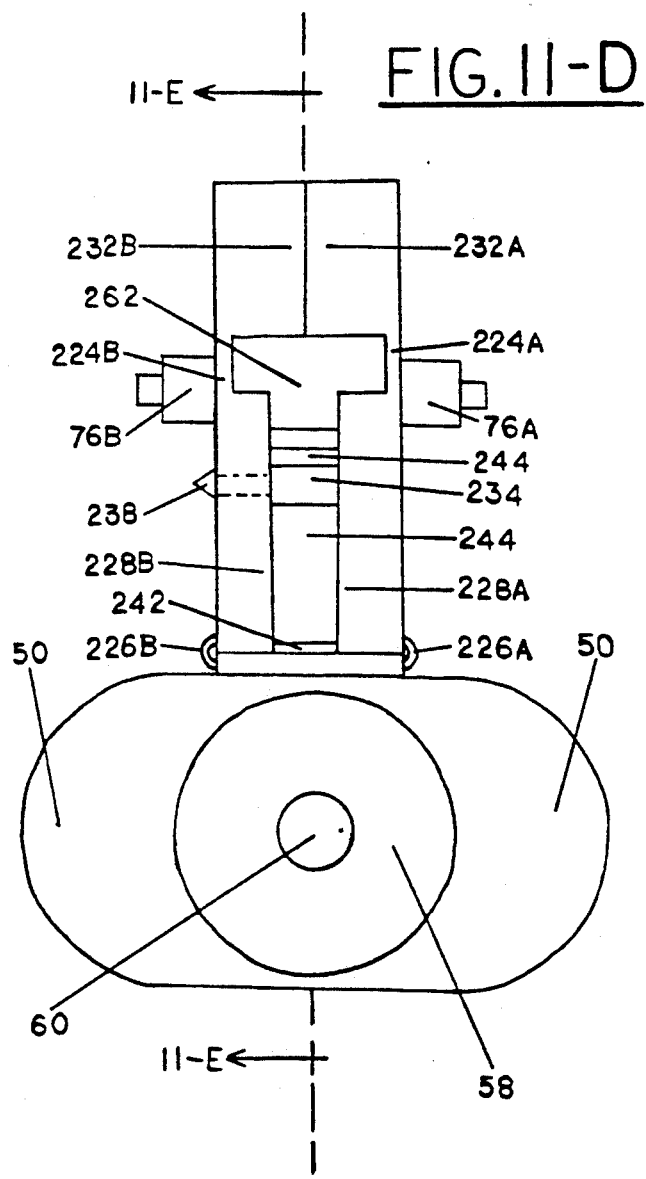

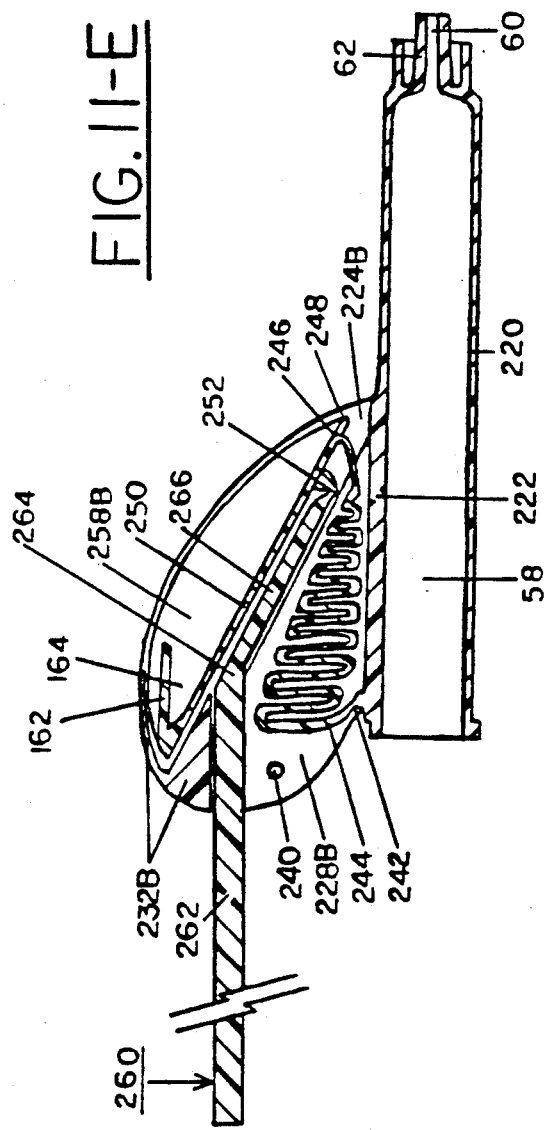

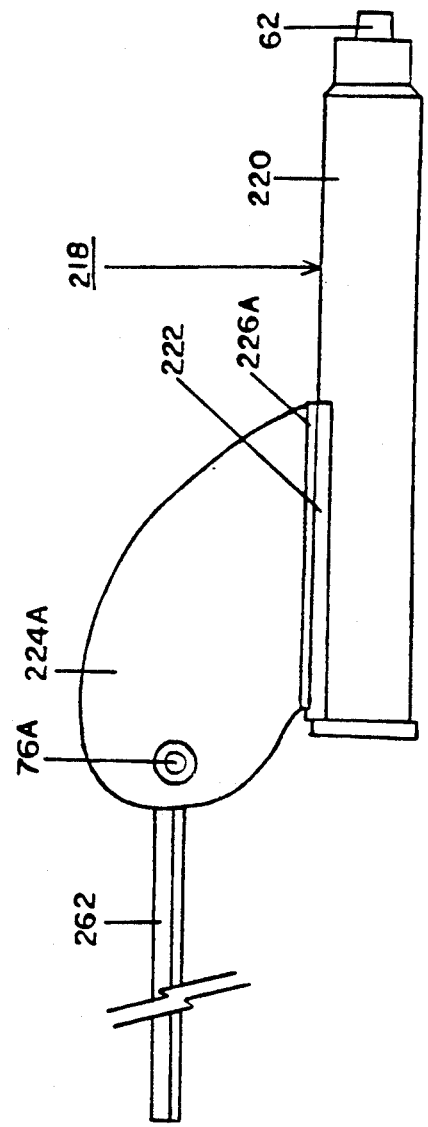

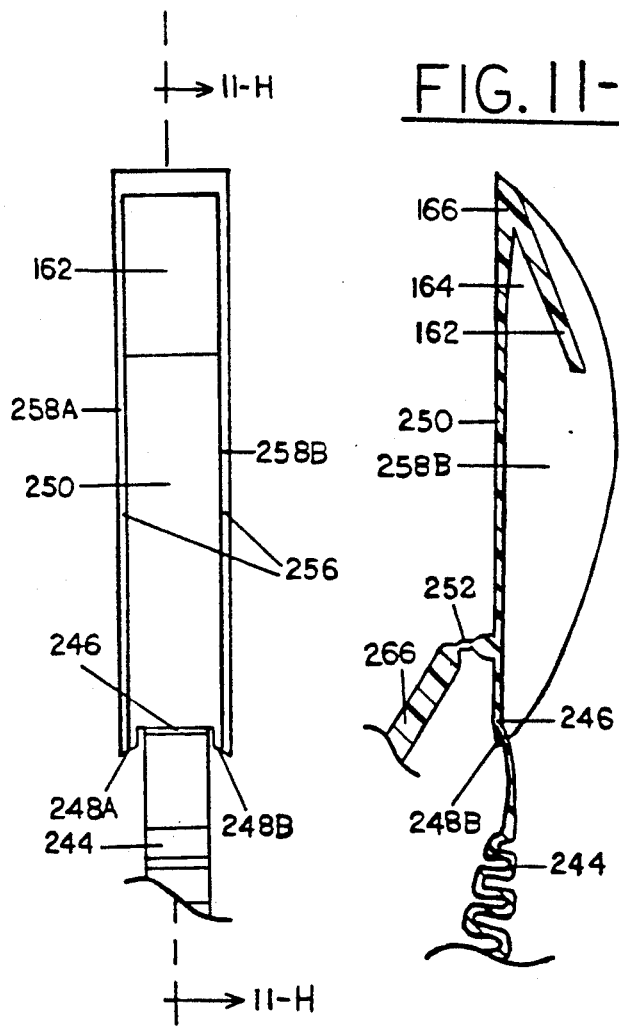

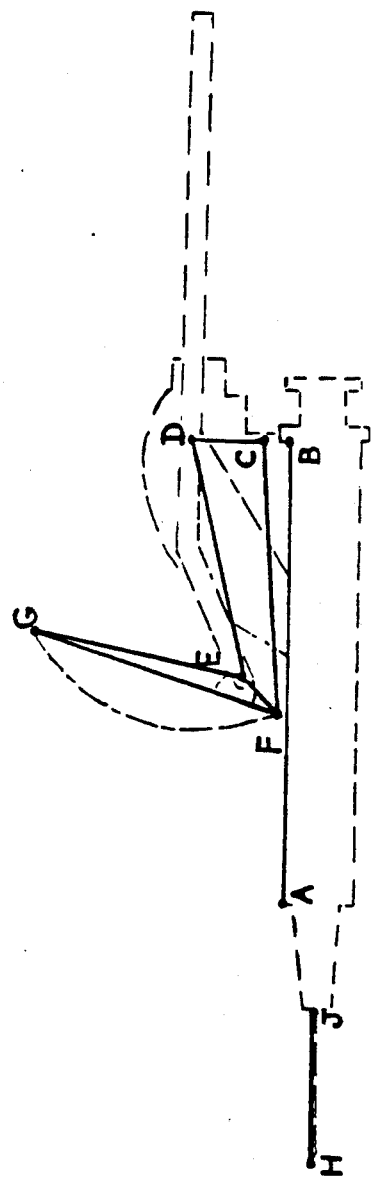

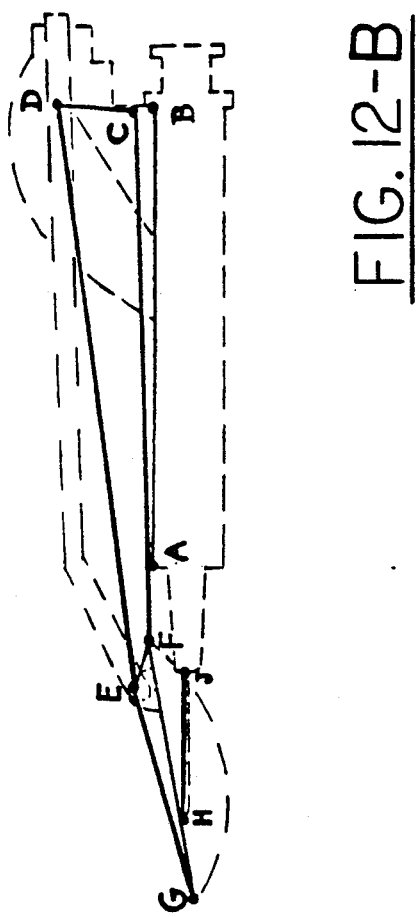
FIG.12-B

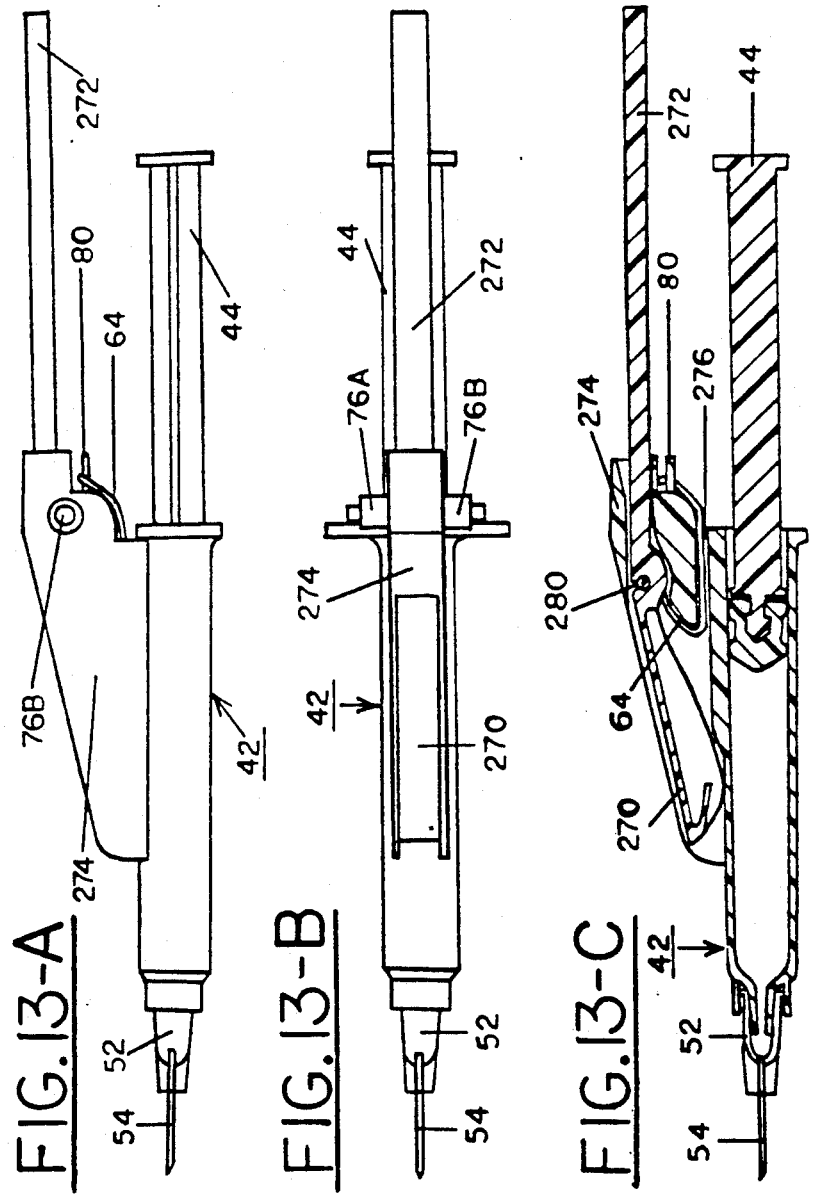

HYPODERMIC NEEDLE SAFETY SHIELD

BACKGROUND OF THE INVENTION

1. Field of Invention

This invention relates to shielding the needle points of hand-held hypodermic needle and syringe injection devices, thereby increasing user convenience and reducing the spread of infectious disease due to accidental needle pricks.

2. Discussion of the Problem

The Washington Post reported in 1987 that on an average day 2,200 American health care workers suffer accidental hypodermic needle punctures.

The two obvious dangers associated with accidental needle punctures are infectious injury and death by disease. The Center for Disease Control says that 200 to 300 health care workers die annually because of the direct or indirect consequences of occupationally acquired hepatitis B, and that annually 12,000 become infected with the disease. At least 20 other pathogens are transmitted by needle puncture, including AIDS.

Accidental needle sticks produce other serious but less obvious consequences. Even if an accidental needle puncture does not transmit disease, health care workers and their spouses or sexual partners suffer long-term psychological injury waiting for test results and anticipating the onset of disease. Significant amounts of time are lost from work because of mental suffering, and reduced on-the-job efficiency results merely from being preoccupied with the possibility of disease transmission.

Infectious needle sticks raise health care insurance rates and increase workers' compensation insurance claims and rates. On-the-job friction between workers and employers takes place as an awareness of the dangers of needle sticks is heightened and some workers become irritated by what they perceive as a lack of concern for their well-being.

And now the costly potential for products liability litigation looms larger against against manufacturers and suppliers of traditional hypodermic injection devices as new safer designs become more practical, especially if such alternative designs are not at least made available as an option to potential plaintiffs.

Because of the vast numbers used, hand-held, single-use, disposable hypodermic needle and syringe devices are the single largest causitive instrumentality of accidental puncture injury in the heath care setting. But the greatest percentage of accidental needle sticks from these devices occur not during their primary use during the injection process. It is during the preparation of these devices for disposal, or during disposal, or after disposal, that the greatest percentage of these accidents take place.

Recapping after use, or more accurately, positioning the cap prior to recapping after use, is the most common mechanism of injury. In positioning the cap, the hand holding the cap is moved toward the hand holding the contaminated needle. Bringing the hand holding the cap toward the needle is a movement distinct from, and occurring prior to, the more precise and thoughtfully executed recapping process itself. Since greater distances and tolerances for error are involved in positioning the cap prior to recapping, it is often performed nonchalantly, without deliberation and careful attention, sometimes with disastrous consequences.

Because the process of getting the cap back on the device after use results in so many punctures of the hand holding the cap, the Center for Disease Control has recommended that syringe devices be disposed of after use without replacing the cap.

But an article appearing in the Aug. 4th, 1988 edition of the New England Journal of Medicine recognizes that leaving needles uncapped is not an adequate solution. Although failing to recap a needle would certainly reduce recapping accidents, many other accident sequences occur precisely because the used needles involved are in an uncapped condition. If needles withdrawn from patients are simply left uncapped as a matter of course, the frequency of accidental encounters with needles intentionally left uncapped will increase as the frequency of recapping accidents declines.

The article suggests that safer syringe design is a better solution than not recapping. Such design should be an integral part of the device and should allow capping to take place while keeping hands out of harm's way.

The Center for Disease Control itself recognizes the value of bringing innovation of design to bear on the problem when it says in its published guidelines to prevent the spread of AIDS and hepatitis B, "Whenever possible, the employer should identify devices and other approaches to modifying the work environment which will reduce exposure risk."

The National Academy of Sciences Committee on Trauma Research has categorically stated that improvement in product design is among the best of the ways available to reduce puncture injuries to health care workers.

3. Discussion of Prior Art

Most design proposals intended to make hand-held hypodermic needle and syringe devices, herein sometimes called "hypo units" for brevity, safer to use and dispose of can be categorized according to one of four general approaches, each of which suffers serious drawbacks.

A. The First Approach

The first approach is to mount a protective cylindrical sheath about the exterior of the syringe barrel of the hypo unit. The distal end of such a sheath has a small aperture or larger opening through which the needle projects. Such a guard slides forward upon the syringe barrel axially into a protective, needle-containment mode in conjunction with a manual push, twist, or other movement or combination of movements. Representative of this approach are U.S. Pat. No. 4,573,976 to Sampson (1986), U.S. Pat. No. 4,826,491 to Schramm (1989), and U.S. Pat. No. 4,826,488 to Nelson (1989).

The major drawbacks associated with this sort of approach are as follows:

(1) The capping process nominally requires two hands, or at a minimum, an awkward repositioning of the one hand, making instant implementation impossible. The user must either take time out from whatever task is being performed to complete the capping process or must lay the hypo unit down uncapped until the capping process can be completed at a later, more convenient time, when both hands are free. This is a major drawback.

(2) The cap obscures the fluid chamber. This inhibits illumination of the chamber and makes monitoring the chamber contents more difficult, both when loading the unit and when injecting the patient.

(3) The capping mechanism constitutes an awkward and unacceptable enlargement to the distal portion of the hypo unit, thereby becoming an irritation and impeding the primary use of the apparatus, especially when holding the unit at acute angles to the surface of the patient's skin during insertion into a vein.

B. The Second Approach

The second approach is to attach a cap around the hub of the needle instead of around the barrel of the syringe. These caps usually slide axially into and out of a protective mode either in conjunction with manual push, twist, or other movement or combination of movements such as U.S. Pat. No. 4,826,490 to Byrne (1989), U.S. Pat. No. 4,816,022 to Poncy (1989), and U.S. Pat. No. 842,587 to Poncy (1989), or by manually triggered spring action such as U.S. Pat. No. 4,813,940 to Parry (1989), or automatically triggered spring action, such as U.S. Pat. No. 4,863,435 to Sturman (1989).

Except that the fluid chambers of these devices are not obscured, these devices suffer from every drawback present in the first approach, plus the additional following drawbacks:

(1) The manually operated devices in this category require that the hand not holding the syringe must be brought unreasonably near the needle point.

(2) The automatically triggered devices in this category prevent intelligent manual control and result in premature or otherwise unwanted operation.

(3) Many of these devices are overly complicated and costly to manufacture. Additionally, manufacturing some of them under sterile conditions would be difficult and costly and involve the invention of costly new manufacturing equipment.

(4) Most involve an elongation of the needle hub and a consequent weakening of the apparatus' ability to safely tolerate lateral stress. Also, the elongation of the needle hub requires more "dead space" and the consequent wasting of medicine.

(5) None of these devices permit the use of any of the currently standard needle and needle hub configurations, and therefore whole product lines of time tested needles and syringes would have to be abandoned to introduce these new devices on a wide scale.

C. The Third Approach

The third approach comprises those needle and syringe combinations where the needle is automatically retracted or manually retractable up into the evacuated fluid chamber or some other internal cavity of the apparatus after use, either by the force of a primary or secondary push or pull of the plunger, such as U.S. Pat. No. 4,826,484 to Haber (1989), and U.S. Pat. No. 4,826,489 to Haber (1989), or by spring action such as U.S. Pat. No. 4,838,869 to Allard (1989), thereby withdrawing the needle point from an exposed position. The drawbacks are:

(1) These devices often require two hands to operate, thereby preventing instant implementation. Again, this is a major drawback. Those devices in this category that do not require two hands to operate are often automatically operated and thus prevent manual control.

(2) Most of these devices impede unrestricted observation of the fluid chamber.

(3) Many of these devices possess an unacceptable enlargement or unwieldy extension of the distal end of the hypo unit.

(4) Perhaps the chief drawback to these devices are that they are vastly over-complicated. They are simply prohibitively expensive to manufacture, especially under sterile conditions. The complexity of design could lead to manufacturing defects, in one case possibly resulting in a dangerous malfunction involving aspiration and injection of air into the patient. And if air were present in the system, the less than adequate view of the fluid chamber could contribute to preventing a timely discovery of the situation.

(5) None of these devices permit the use of any of the currently standard needle and needle hub configurations.

D. The Fourth Approach

The fourth approach comprises needle covers that swing longitudinally on hinges mounted close to the distal end of the apparatus, near the needle hub, either in a unitary fashion such as U.S. Pat. No. 4,838,871 to Luther (1989) and U.S. Pat. No. 4,872,552 to Unger (1989), or in pairs like alligator jaws such as U.S. Pat. No. 4,820,277 to Norelli (1989), between a position exposing the needle to a position covering the needle. The cover or covers may be manually placed from one position to another or moved into place by triggering the motive power of a spring or elastic material such as U.S. Pat. No. 4,883,469 to Glazier (1989). The drawbacks to this type of approach are:

(1) The operation of most of these devices require that the operator place fingers within unacceptably close distances to the needle and move fingers in dangerous directions in relation to the needle tip. Capping in the conventional way appears far safer than the utilization of some of these devices.

(2) The use of most of these devices requires an awkward repositioning of the hand or requires two hands, precluding instant implementation.

(3) Most are overly complicated to manufacture.

(4) Most involve an unacceptable enlargement or modification to the shape of the distal end of the hypo unit.

(5) None of these devices permit the use of any of the currently standard needle and needle hub configurations.

E. The Feimer Approach

One device that doesn't fit well into any of the four categories listed above deserves special attention. This is U.S. Pat. No. 4,915,696 to Feimer (1990). This is the only example of prior art uncovered by the present inventor that uses a control rod, referred to in the Feimer patent as a "needle securing plunger," pushed from the rear to work the mechanism. The advantage of such a control, if it is not positioned so as to accidentally interfere with the operation of the primary plunger, is that it enables the operator to implement the capping process at his or her discretion instantly, without the need to reposition the hand or the need to involve the free hand, which may be engaged in other important tasks.

But the Feimer invention has major drawbacks.

The control rod is positioned so close to the primary plunger that it gets in the way, thus constituting an annoying impediment to using the hypo unit for its primary function of injecting medicine or withdrawing blood for analysis.

The Feimer design also precludes any use involving the removal of the needle from the syringe barrel.

The device prior to use also encumbers the distal portion of the hypo unit, which is undesirable.

The device cannot be used in conjunction with a conventional cap of a type currently supplied in conjunction with existing needle and needle hub designs, thus precluding the option of using a conventional cap secured to a conventional hub after loading of the medicine and before patient injection, which in some settings is a common practice. It also precludes the option of using a conventional cap during use after blood withdrawal. Removing the device from the tip of a needle after deployment, using the technique described in the Feimer patent, also requires fingers to be placed dangerously close to the needle point.

If for any reason the operator could not use the "needle securing plunger" device because of a malfunction, or if for any other reason the operator did not want to use it, the Feimer design does not permit the use of a conventional cap to be used as an alternative means of capping the needle.

Considering manufacturers have a great investment of time and money in their current product lines, the Feimer device has the major disadvantage of not being adaptable for use with most of the needle, needle hub, and cap designs currently being manufactured and marketed.

Because the Feimer device has a very small "needle pocket" to receive the needle tip, it would not transmit to the operator an unmistakable visual message that the needle tip has been properly engaged fully into the "needle pocket." If the pocket has been advanced a little too far, or not quite far enough, and has therefore failed to engage properly, such misengagement could easily go unnoticed. Nor would the device transmit an unmistakable tactile message of proper or improper engagement.

It appears that occasional failure might be expected because of the inability of the most convenient construction materials, such as the plastic that syringes are made of, to remain in a stressed position for long storage periods without losing some "memory." There is an inherent tendency for long thin flexible plastic parts to warp or undergo changes in the nature of their resiliency under prolonged flection, thereby causing them not to unfailingly engage with precision as planned within a wide range of rapid speeds and varying loads.

Because the "needle securing plunger" is too close to the syringe barrel plunger to allow unencumbered use of the main plunger without accidental interference from the "needle securing plunger," the distal end of the "needle guide structure portion" of the "needle securing plunger" could encounter the patient by being inadvertently pushed during the depression of the main plunger, causing the "needle guide structure portion" to become misaligned as well as interfering with the injection.

If a hypodermic needle were to be even slightly bent during the injection process, the "needle pocket" and the "needle guide structure portion" could lose their alignment with the shaft of the needle. And the smallness of the parts would make discovery of failure difficult and render the instrument more dangerous than an instrument known to be uncapped.

The Feimer device also appears prone to failure due to puncture of the "needle pocket" during an accidental forceful frontal collision. The New England Journal of Medicine, in an article dated Aug. 4, 1988, reports that long needles puncturing through the tops of improperly mated short caps is a significant cause of needle sticks. If needles regularly puncture conventional cap tops, it would seem that they could also puncture through the tiny "needle pocket" of the Feimer device.

The Feimer device also appears prone to failure even after an otherwise successful deployment due to the likelihood of a mechanical uncoupling of the needle tip from the "needle pocket" during an accidental encounter exerting even a moderate lateral force upon the distal end of the hypo unit. After deployment, it places a pair of small sharp prongs like hooks at the very end of the needle, prongs that seem almost perfectly designed to snag fabric and thereby disengage the invention from the needle tip.

Also, the needle could easily be pulled free from the "needle pocket" of a unit if, during the disposal process, many units were disposed of together and became entangled with one another. Such an event would produce a danger to any subsequent handler of the refuse. As the Aug. 8, 1988 New England Journal of Medicine article also points out, the handling of refuse is a major mode of needle stick injury.

In short, the Feimer device interferes with the primary use of the hypo unit during the operation of the primary plunger, and it also depends for its proper functioning on the tediously precise alignment, advancement, and terminal placement of a very small "needle pocket" supported at the end of a long, flexible plunger shaft having a tiny vee notch on its end as its means of alignment and guidance. This plunger shaft is designed to remain in storage under tension and must operate in an identical manner under widely varying activation speeds and thumb forces. If the device fails to function as planned either during or at any time after its deployment, discovery of the malfunction may not be apparent until an unfortunate accidental encounter with a supposedly protected needle. If such an accidental encounter causes someone serious harm, in view of the obvious danger of accidental disengagement, misengagement, or puncture of so small a "needle pocket," a manufacturer or supplier of the device would likely face a subsequent costly and possibly successful products liability suit.

F. Summary of Prior Approaches

Considering all the above, an explanation of why the various new safety designs have not achieved wide acceptance becomes obvious. The designs offered to date have serious drawbacks. They all constitute, in one way or another, an unacceptable compromise to the suitability of the unit to achieve its primary function with ease and economy.

OBJECTIVES AND ADVANTAGES OF THE PRESENT INVENTION

The primary objective of this invention is to lessen the incidence of accidental infectious needle punctures that sometimes occur during the handling, operation, and disposal of hypodermic needle and syringe injection devices.

A secondary objective is to increase the operating convenience of such devices.

This invention meets these objectives by providing a mechanism that can be connected to an otherwise ordinary hypo unit and that enables the operator to quickly, surely, and easily shield the needle point immediately upon its withdrawal from the patient. And in meeting these objectives, the invention enhances rather than reduces the operating efficiency of the injection device.

Furthermore, this invention enables the operator to maintain manual control over the initiation of such shielding process, thus avoiding the possibility that premature or otherwise unwanted deployment of the shield might take place.

This invention also enables the operator to accomplish the shielding process with one hand, without the need to change or shift finger positions or grip upon the syringe barrel.

Perhaps most importantly, this invention allows the operator to perform the shielding process easily and safely without the necessity of carefully observing and visually monitoring and verifying the progress and completion of such shielding process during a time when such operator's attention may be necessarily distracted or divided between other important competing medical tasks. A fast glance or tactile sensation alone imparts to the user adequate information concerning the progress and completion of the shielding process.

Additionally, this invention provides these advantages without requiring modification to existing needle designs, needle hub designs including luer connection designs and low-dose minimum "dead space" designs, needle cementing processes and equipment, fluid chamber designs, and fluid chamber piston designs—all of which have proven themselves in the course of time to be effective to the point of elegance in their precision, simplicity, reliability, and ease of use.

The invention can be used with all types of hypo units, including re-useable types, types having needles cemented directly into the distal end of the syringe barrel, types having needles secured to syringe barrel nozzles via slip-on needle hubs, and types having eccentric syringe barrel nozzles.

Aside from the problem of accidental needle punctures, modern hypodermic needle and syringe designs are perfectly suited to their intended uses and methods of manufacture. What is needed, and what this invention provides, is not an extensive redesign of the critical functional parts of these devices, but a method and mechanism that will preserve the existing functional parts of these devices while rendering them safer to use.

Specifically, this invention permits the shielding mechanism to be kept entirely separate and away from the distal portion of the hypo unit until the shield is intentionally deployed. Such a configuration permits time-tested, currently standard needles and needle hubs to be used and permits an unimpeded view of the fluid chamber. The invention does not interfere with the manufacture of the injection device, the loading of the injection device, or the use of the injection device.

Various embodiments of the invention permit it to be constructed and mounted in various ways that afford various advantages. It can be added onto a conventional hypo unit without any modification to the conventional hypo unit. Or it can be mounted into a shoe affixed to a modified syringe barrel of a hypo unit in such a way as to permit an operator the option, which he or she may want to exercise for various reasons, of easily discarding the entire invention prior to using the hypo unit to which it is mounted. Or the entire invention, with all essential working parts, can be molded integral with the syringe barrel of a hypo unit, in one piece, from one type of material such as plastic, thus reducing the variable costs involved in its manufacture and assembly.

This invention permits the operator's thumb or finger to push the primary plunger without accidentally encountering the pushrod that operates the shielding device. Such unintentional encounter is prevented by positioning the pushrod a significant distance away from the primary plunger. Also, the proximal end of the pushrod extends farther to the rear of the apparatus than does the primary plunger, eliminating any chance that the end of the pushrod will be encountered accidentally when pushing the primary plunger. Such an arrangement also allows the operator to maintain a tactile understanding of the position of the operating parts of the device without visual surveillance; that is, the operator is able to find and selectively push first the primary plunger and then the pushrod without the necessity of visually monitoring the process. Thus, the operator's attention need not be diverted from other important medical tasks.

The shielding device, although visually unusual, actually aids rather that hinders the use of the hypo unit for its primary function. The housing allows the operator's fingers to assume greater contact with and and control of the hypo unit and makes accidentally dropping the hypo unit less likely than it would be in the absence of the housing. Also, the projecting finger nubs help stabilize the hypo unit during depression of the pushrod without interfering with any aspect of hypo unit's primary use.

The pushrod allows the operator to operate the shield at the precise time the operator chooses, which could be immediately after the operator withdraws the needle from the patient, or which could be not at all if the operator chooses in a particular situation to instead use a needle shearing device, or a puncture resistant disposal container, or a cap of the ordinary, currently available variety.

Further objects and advantages of this invention will become apparent from a consideration of the drawings and ensuing description of it.

DESCRIPTION OF DRAWINGS

FIG. 1-A shows the invention being held and operated by a human hand.

FIG. 1-B is a perspective view of the invention showing the side and front areas, with the shield in its position of containment within the housing prior to deployment.

FIGS. 1-C and 1-D are perspective views of the invention showing the side and rear areas.

FIG. 1-C depicts the invention with the shield in a position of partial rotation during deployment.

FIG. 1-D depicts the invention after the shield has completed the first phase of rotation and is sliding toward the distal end of the hypo unit.

FIG. 1-E is a partially exploded view showing the pushrod, the hingedly connected shield, and the attached rubber band, and showing the interior of the housing in a cut-away perspective from the top front right side.

FIG. 1-F is a rear view of the basic version of the invention.

FIGS. 1-G to 1-L, inclusive, are sectional views from the side, bisecting the invention longitudinally and showing it in various stages of operation.

FIG. 1-G shows the invention affixed atop an otherwise conventional syringe barrel filled with medicine prior to the hypo unit being used to inject a patient. The shield is in a position of containment within the housing prior to deployment.

FIG. 1-H shows the shield undergoing rotation during deployment after the plunger has been fully depressed into the syringe barrel during the injection process.

FIG. 1-I shows the shield after the first phase of rotation, as it is sliding in a distal direction along the exterior surface of the syringe barrel during deployment.

FIG. 1-J shows the shield during the process of deployment, advancing up the needle.

FIG. 1-K shows the shield during process of deployment, after the needle retaining plate has surmounted the needle tip but before the shield has been drawn rearward by the rubber band.

FIG. 1-L shows the needle tip contained within the needle enclosure of the shield after consummation of the deployment process.

FIG. 2-A is a detailed front view, with phantom lines added, of a shield of the type shown or partially shown in FIGS. 1-A through 1-L.

FIG. 2-B is a detailed side view of the shield shown in FIG. 2-A.

FIG. 2-C is a view of the distal end of the pushrod and the back of the rotating spine of the shield prior to the two being connected, showing the hinge plates, the phantom outline of the receiving holes, and the pintles of the fulcrum hinge.

FIG. 3-A and FIG. 3-B are the front and side view, respectively, with phantom lines added, of a shield of the type shown or partially shown in FIGS. 2-A, 2-B, and 2-C, modified so that it connects to the pushrod via a bendable fulcrum hinge instead of a pintle, or "T" type, fulcrum hinge, and possessing the additional feature of a needle trap.

FIG. 3-C is a sectional view of the needle trap shown in FIGS. 3-A and 3-B.

FIG. 4-A and FIG. 4-B are the front view and side view, respectively, with phantom lines added, of a shield with an alternate configuration at its proximal end referred to herein as a rolling heel, and possessing an alternate needle trap and a modified needle enclosure.

FIG. 4-C is a sectional view of the alternate needle trap shown in FIGS. 4-A and 4-B.

FIG. 5-A is a side view, with phantom lines added, showing the shield in the process of deployment, and showing the wedge-shaped stopper, the alternate needle trap, and the modified needle enclosure.

FIG. 6-A is a perspective view depicting an alternate housing having a foot that permits the housing to be secured to, and subsequently optionally removed from, the hypo unit via a shoe affixed to the syringe barrel.

FIG. 6-B is a rear view of the housing depicted in FIG. 6-A.

FIG. 7-A is a perspective view of an alternate version of the shoe shown in FIG. 6-A possessing a circumference ring and pawl configuration that permits attachment to an unmodified typical syringe barrel.

FIG. 8-A is a perspective view of a second alternate housing that mounts to a conventional hypo unit via a circumference ring and pawl arrangement.

FIG. 8-B is a side view of the housing depicted in FIG. 8-A, mounted to a conventional syringe barrel.

FIG. 8-C is a sectional view from the side, showing the housing depicted in FIG. 8-B bisected longitudinally.

FIG. 9-A shows a housing similar to that shown in 8-A and 8-B, but equipped with secondary finger flanges instead of finger nubs.

FIG. 10-A shows a third alternate housing and accompanying low-dosage shield design affixed to a low-dosage hypo unit via a clip projecting from the underside of the housing.

FIG. 11-A is a side view of yet another embodiment of the invention which combines the syringe barrel and all the essentials of the basic invention into one integral part which can be molded from plastic or some other material in one piece, in one operation, and then assembled in a folding operation. The embodiment is depicted prior to implementation of the folding operation.

FIG. 11-B is a top view of the embodiment shown in FIG. 11-A.

FIG. 11-C is a rear view of the embodiment shown in FIG. 11-A.

FIG. 11-D is a rear view of the embodiment shown in FIG. 11-A, after being folded and secured into an assembled product.

FIG. 11-E is a sectional side view of the embodiment shown in FIG. 11-A, folded into a an assembled product.

FIG. 11-F is a side view of the embodiment shown in FIG. 11-A, folded and secured into a an assembled product.

FIG. 11-G is a front view, with phantom lines added, of a shield of the type shown or partially shown in FIGS. 11-A, 11-B, 11-C, and 11-E.

FIG. 11-H is a sectional side view of the shield shown in FIG. 11-G.

FIGS. 12-A and 12-B show and label certain angles, lines, and points which relate to the operation of the invention and which are discussed in the text. FIGS. 12-A and 12-B correspond with, and should be studied in conjunction with, FIGS. 1-H and 1-K, respectively.

FIG. 13-A is a side view of the non-rotating embodiment of the invention before deployment.

FIG. 13-B is a top view of the non-rotating embodiment of the invention before deployment.

FIG. 13-C shows a sectional view of the the non-rotating embodiment of the invention from the side before deployment.

FIG. 13-D shows the non-rotating embodiment of the invention from the side during deployment.

FIG. 13-E shows a sectional view of the the non-rotating embodiment of the invention from the side after deployment.

LIST OF REFERENCE NUMERALS

42: Hypodermic Needle and Syringe Apparatus, or "Hypo Unit"
44: Typical Plunger
46: Typical Syringe Barrel
48: Typical Syringe Barrel Rim
50: Typical Finger Flanges
52: Typical Luer Lock Needle Hub
54: Typical Hypodermic Needle
56: Typical Hypodermic Needle Cap
58: Typical Fluid Chamber
60: Typical End Hole
62: Typical Syringe Barrel Nozzle
64: Rubber Band
66: Housing
68: Housing-Modified Syringe Barrel
70: Floor
72: Roof
74A: Right Wall
74B: Left Wall
76A: Right Finger Nub 76B: Left Finger Nub
78: Rubber Band Channel
80: Rubber Band Peg
82: Pushrod Channel
84: Structural Cavity
86: Spine Ledge
88: Fore-End Slot
90: Vertical Drop-off and Cutout
92: First Alternate Housing
94: Shoe-Modified Syringe Barrel
96A: First Alternate Right Side Wall
96B: First Alternate Left Side wall
98: Slotted Foot
100: Slotted Shoe
102: First Alternate Rubber Band Channel
104: Shoe Groove
106: Alternate Slotted Shoe
108A: Right Shoe Pawl
108B: Left Shoe Pawl
110: Shoe Ring
112: Second Alternate Housing
114A: Second Alternate Right Side Wall
114B: Second Alternate Left Side Wall
116: Rubber Band Notch
118: Circumference Ring
120: Pawl
122: Blade Spring
124: Second Alternate Floor
126: Rim Stop
128: Pushrod
130: Shaft
132: Elbow
134: Fore-End
136A: Right Pintle
136B: Left Pintle
138A: Right Receiving Hole
138B: Left Receiving Hole
140A: Right Hinge Plate
140B: Left Hinge Plate
142: Wedge-Shaped Stopper
144: Pintle, or "T" Type, Fulcrum Hinge
146: Bendable Fulcrum Hinge
148: Shield
150: Rotating Spine
152A: Right Shield Wall
152B: Left Shield Wall
153A: Rolling Heel Right Shield Wall
153B: Rolling Heel Left Shield wall
154: Shield Face
155: Rolling Heel Shield Face
156: Rocking Heel
158A: Rocking Heel Right Side Inlet
158B: Rocking Heel Left Side Inlet
160A: Right Shield Wall Tip
160B: Left Shield Wall Tip
162: Needle Retaining Plate
164: Needle Enclosure
166: Point Barrier
168: Needle Trap
170: Alternate Needle Trap
172: Rolling Heel
174A: Rolling Heel Right Side Inlet
174B: Rolling Heel Left Side Inlet
176: Modified Needle Enclosure
178: Modified Needle Retaining Plate
180A: Modified Right Shield Wall
180B: Modified Left Shield Wall
182: Modified Rotating Spine 184: Typical Low Dosage Hypo Unit
186: Typical Low Dosage Syringe Barrel
188: Typical Low Dosage Needle Hub
190: Typical Projecting Hub Lip
192: Third Alternate Housing
194: Clip
196: Fixed Pawl
198: Third Alternate Roof
200: Third Alternate Rubber Band Notch
202: Low Dosage Shield
204: Low Dosage Shield Face
206: Low Dosage Lip Surmounting Ramp
208: Low Dosage Pushrod
210: Low Dosage Shaft
212: Low Dosage Elbow
214: Low Dosage Fore-End
216: Small Rubber Band
218: Integral Assembly
220: Integral Syringe Barrel
222: Integral Floor
224A: Integral Right Wall Wing
224B: Integral Left Wall Wing
226A: Integral Right Wall Hinge
226B: Integral Left Wall Hinge
228A: Integral Right Fore-End Shelf
228B: Integral Left Fore-End Shelf
230A: Integral Right Portion of Pushrod Channel
230B: Integral Left Portion of Pushrod Channel
232A: Integral Right Roof
232B: Integral Left Roof
234: Integral Spacer
236: Integral Fastening Dowel
238: Integral Fastening Crown
240: Integral Fastening Hole
242: Integral Bendable Spring Mooring Point
244: Integral Expansion Spring
246: Integral Bendable Heel Connection
248A: Integral Right Rocking Heel
248B: Integral Left Rocking Heel
250: Integral Rotating Spine
252: Integral Bendable Fulcrum Hinge
254: Integral Shield
256: Integral Shield Face
258A: Integral Right Shield Wall
258B: Integral Left Shield wall
260: Integral Pushrod
262: Integral Shaft
264: Integral Elbow
266: Integral Fore-End
268: Alternate Finger Nub Design
270: Rigid Shield
272: Rigid Pushrod
274: Rigid Housing
276: Rigid Pushrod Channel
278: Rigid Rubber Band Channel
280: Rigid Rubber Band Notch
282A: Right Secondary Finger Flange
282B: Left Secondary Finger Flange
284: Modified Circumference Ring

DESCRIPTION OF THE INVENTION

The invention is composed of four distinct components. There is more than one version of each component. Different versions of each of the four components provide alternative advantages.

Operating embodiments of the invention are constructed by assembling particular versions of each of the four components together into a working mechanism which is affixed to an otherwise ordinary hand-held hypodermic needle and syringe injection apparatus used in a medical context to draw or inject fluid.

Any otherwise ordinary hand-held hypodermic needle and syringe injection apparatus used in conjunction with any particular embodiment of the invention is referred to hereinafter as a "hypo unit."

Referring to FIG. 1-C, a basic embodiment of the invention assembled from a basic version of each of the four components of the invention may be seen connected to a hypo unit 42. The four basic components of the invention are a housing 66; a pushrod 128; a shield 148; and a method of resilient or semiresilient resistance, which in its basic version, as shown in FIG. 1-C, is a rubber band 64.

To avoid digressions and tangential explanations concerning its nature in later sections, a description of hypo unit 42, which is essentially a standard needle and syringe apparatus with which the invention works, is presented in Subsection A. A detailed description of the four components of the invention, including an explanation of each of the versions of each of the four components, is presented in Subsections B, C, D, and E. Subsection F describes the preferred embodiment of the invention. Subsection G describes an additional, simplified, embodiment of the invention, referred to herein as the non-rotating embodiment.

A. Description of the Hypo Unit

1. Necessary Modifications to the Hypo Unit

In all cases, the hypo units used in conjunction with the several embodiments of the invention are of completely ordinary manufacture and typical function, subject to the following exception: A portion of the exterior, proximal surfaces of the syringe barrels of the hypo units used in conjunction with three of the embodiments of the invention are in one of three ways modified for use with those embodiments. Such modification is for the purpose of securing those particular embodiments to those particular syringe barrels.

Although all three of these syringe barrel modifications are described and numbered with particularity, for simplicity the aggregation of standard hypodermic needle and syringe apparatus parts with which the invention functions, together with any modified or unmodified syringe barrel used therewith, is given the generalized designation of "hypo unit" and given the part number "42."

The first way that the syringe barrel of hypo unit 42 is modified for use with a particular embodiment of the invention is by its being manufactured integral with housing 66, thereby insuring a permanent and conveniently accomplished connection between housing 66 and hypo unit 42. FIG. 1-C shows hypo unit 42 having a housing-modified syringe barrel 68 which in this way permanently joins to housing 66.

The second way that the syringe barrel of hypo unit 42 is modified for use with a particular embodiment of the invention is by its being manufactured integral with an entire and complete embodiment of the invention made entirely in one piece, in one molding process, from one type of plastic material. Such an integral syringe barrel 220 is shown in FIGS. 11-A, 11-B, 11-C, 11-D, 11-E, and 11-F. (Incidentally, the first number in the designation of the figures identifies a particular parts group; the second number, that is, the number which follows the hyphen, identifies different views or perspectives of that particular parts group.)

The third way that the syringe barrel of hypo unit 42 is modified for use with a particular embodiment of the invention is by its being manufactured integral with a slotted shoe 100 comprising a portion of its exterior proximal surface, into which a slotted foot 98 on the bottom of the housing component of the invention can conveniently be inserted. Such a modification is depicted in FIGS. 6-A and 6-B, showing a shoe-modified syringe barrel 94 manufactured as one piece with slotted shoe 100. Slotted foot 98, on the bottom side of a first alternate housing 92, permits first alternate housing 92 to be conveniently attached to and removed from hypo unit 42.

With the important exception of the the three syringe barrel modifications described above, every part of every hypo unit used in conjunction with the invention is of ordinary manufacture, presently commercially available, and used without modification. And not all embodiments of the invention even require hypo units to have syringe barrel modifications of any type.

Some embodiments of the invention attach to syringe barrels of completely ordinary design, such as a typical syringe barrel 46 depicted in FIGS. 7-A, 8-A, 8-B, 8-C, and 9-A. A typical low dosage syringe barrel 186 shown as a part of a typical low dosage hypo unit 184, as depicted in FIG. 10-A, is also of current commercially available design and manufacture.

2. The Operational Specifics of the Hypo Unit

Hypo unit 42 used with the basic embodiment of the invention may be described with particularity as having, as depicted in FIG. 1-C, a housing-modified syringe barrel 68 opened at the proximal end, into which is inserted a typical plunger 44 that can be operated by a human thumb or finger.

A typical end hole 60, such as the one shown sectionally from the side in FIG. 1-G and from the rear in FIGS. 11-C and 11-D, longitudinally transfixes a typical syringe barrel nozzle 62, such as the one shown in FIGS. 11-A, 11-B, 11-E, 11-F. A typical luer lock needle hub 52 as shown in FIG. 1-C, or some similar type of connecting device such as a typical low-dosage needle hub 188 as can be seen in FIG. 10-A, fits onto nozzle 62, thereby allowing a typical hypodermic needle 54, as shown in FIG. 1-C, which is cemented into the hub, to be attached to the distal end of the housing-modified syringe barrel 68 as shown in FIG. 1-C. A sealed connection is thereby formed between the hollow interior of needle 54 and a typical fluid chamber 58 identical to that shown sectionally in FIG. 1-G and from the rear in FIGS. 11-C and 11-D. Alternately, needle 54 is cemented directly into the distal end of the syringe barrel in some hypo units.

A typical syringe barrel rim 48, or bead, circumscribes the opening at the proximal end of housing-modified syringe barrel 68 shown in FIG. 1-C. Typical syringe barrel rim 48 also circumscribes the proximal opening of typical syringe barrel 46 shown in FIGS. 7-A, 8-A, 8-B, 8-C, and 9-A, and typical low-dose syringe barrel 186 shown in FIG. 10-A. Integral with rim 48 are typical finger flanges 50 projecting radially away from rim 48 in opposite directions, generally within the plane defined by rim 48.

Needle 54 is typically affixed to the distal end of hypo unit 42 and delivered from its point of manufacture to its point of use capped with a typical hypodermic needle cap 56 of the type that can be seen in FIGS. 6-A, 7-A, 8-A, and 8-B. Cap 56 secures to and generally engages with the hub structure of needle 54, such as luer lock needle hub 52 shown in FIG. 1-C, or low dosage needle hub 188 shown in FIG. 10-A.

Though only two varieties of needle hubs are shown in the drawings, the invention is well suited for use with hypo units having all types of needle attachment arrangements, including those hypo units having no detachable hub, wherein the needles are permanently cemented into the distal end of the syringe barrel. The invention can also be used with hypo units having needles secured to syringe barrel nozzles via slip-on, or slip-tip, needle hubs; and those hypo units having needle hubs secured to off-center syringe barrel nozzles, commonly referred to as eccentric tips.

B. Description of the Housing

There are five versions of the housing component. The first version is basic housing 66 shown in FIGS. 1-A through 1-L. The second version is first alternate housing 92 depicted in FIGS. 6-A and 6-B. The third version is a second alternate housing 112 depicted in FIGS. 8-A, 8-B, and 8-C. The fourth version is a third alternate housing 192 depicted in FIG. 10-A. And the fifth version is an integral assembly 218 shown in FIGS. 11-A through 11-F.

Each of these versions is discussed in Subparts 1, 2, 3, 4, and 5 below. The most important features of the housing component of the invention are summarized in Subpart 6.

1. The Basic Version of the Housing

Housing 66, shown in FIGS. 1-A through 1-L, is the basic version of the housing component. It is made as one piece with, and thus permanently connected to, housing-modified syringe barrel 68.

Housing 66 is depicted in FIG. 1-E in a cutaway perspective view. Housing 66 is a structure situated near the proximal end of hypo unit 42. It possesses a generally hollow distal portion wherein shield 148 is contained in an inverted position prior to deployment. Three rectangular holes run through the solid proximal portion of housing 66 in a longitudinal direction, all generally parallel to one another and all parallel to and within the same plane as the longitudinal axis of hypo unit 42.

The topmost hole, that is, the hole radially most distant from the longitudinal axis of hypo unit 42, is a pushrod channel 82. The cross-sectional shape of pushrod channel 82 is complimentary to the cross-sectional shape of a shaft 130. Shaft 130 constitutes the proximal portion of pushrod 128. The other two parts of pushrod 128 are a fore-end 134, which constitutes the distal portion of pushrod 128, and an elbow 132, which joins shaft 130 to fore-end 134. Pushrod channel 82 supports and aligns pushrod 128 while permitting shaft 130 to slide longitudinally within pushrod channel 82 along a line generally parallel to the longitudinal axis of hypo unit 42.

The center hole is a structural cavity 84, which is present merely to reduce weight and reduce consumption of construction material without significantly compromising the structural integrity of housing 66.

The bottommost hole, that is, the hole closest to hypo unit 42, is a rubber band channel 78.

Housing 66 has a right wall 74A and a corresponding left wall 74B. A floor 70 comprises the interior bottom surface of housing 66. The top part of housing 66 is enclosed by a roof 72.

From the exterior surface of right wall 74A projects a right finger nub 76A having the general shape of a tiny two-tier wedding cake. There is a corresponding left finger nub 76B projecting from the exterior surface of left wall 74B which is not visible in FIG. 1-E but that may be seen in FIG. 1-F. The two-tier, "wedding cake" shape of nubs 76A and 76B is designed to enhance friction and a mechanical coupling effect between the nubs and the surface texture of a health care worker's gloved or ungloved finger tips, while at the same time minimizing the size of the nubs.

Ideally, finger nubs 74A and 74B should be located one on each side of the longitudinal axis of shaft 130. That is, the longitudinal axis of shaft 130 should intersect the midpoint of an imaginary perpendicular line segment extending from the center of right finger nub 74A to the center of left finger nub 74B.

However, placing nubs 74A and 74B slightly closer to the longitudinal axis of the hypo unit, as they are shown in all the illustrations, makes them more accessible to users with small fingers and does not significantly impair their primary function, which is to assist the user in directing thumb force applied to the proximal end of shaft 130 straight forward along a line in accord with the longitudinal axis of shaft 130.

"An alternate finger nub design 268 is shown in FIG. 5-A. In this embodiment the nubs are cross-sectionally elongated and made intregral with the finger flanges. This one-piece construction provides the benefits of allowing more control of the apparatus by having the nubs near the longitudinal axis of shaft 130 while also allowing them to be easily reachable, even by very small finger tips."

Again referring to the cutaway view of FIG. 1-E, it is shown that the interior of housing 66 is constructed so that an internal surface area, herein called a spine ledge 86, faces forward and upward at an oblique angle. To the rear of spine ledge 86 is the solid part of housing 66 through which runs pushrod channel 82, structural cavity 84, and rubber band channel 64. Forward of spine ledge 86 is the aforementioned hollow area of housing 66 wherein shield 148 is contained prior to deployment.

Into the face of spine ledge 86 is set a fore-end slot 88, which permits the lateral entry of obliquely sloping fore-end 134 located at the distal end of pushrod 128. Fore-end slot 88 permits the surface of a rotating spine 150 to lay flush against spine ledge 86 while shield 148 is contained in housing 66 prior to deployment. A vertical drop-off and cut out 90 at the distal end of spine ledge 86 provides clearance for a pintle, or "T" type, fulcrum hinge 144 situated at the distal end of fore-end 134.

As can be seen in FIG. 1-C and the sectional view in FIG. 1-H, that portion of housing 66 through which runs shaft 130, and which immediately surrounds and defines pushrod channel 82, extends rearward past syringe barrel rim 48 a distance that equals or slightly exceeds the distance that plunger 44 extends rearward past syringe barrel rim 48 when plunger 44 is fully depressed into hypo unit 42. Situated parallel to and directly beneath this rearmost projecting portion of housing 66 is a rubber band peg 80, which projects rearward from a portion of housing 66 situated directly below the proximal portion of pushrod channel 82.

2. The First Alternate Housing

First alternate housing 92 shown in FIGS. 6-A and 6-B is in most respects identical housing 66 shown in FIGS. 1-A through 1-L, but differs as to the method of attaching the invention to hypo unit 42. Unless otherwise noted, all parts and design features of first alternate housing 92 should be assumed to be identical with housing 66, which is the basic version of the housing component of the invention.

Referring to FIG. 6-A unless otherwise noted, it is shown that first alternative housing 92 has no structure similar to floor 70 of housing 66 shown in FIGS. 1-A through 1-L. Instead, first alternative housing 92 possesses slotted foot 98 along the outside bottom edges of a first alternate right side wall 96A and a first alternate left side wall 96B. Because there is no floor structure between the two halves of slotted foot 98, a first alternate rubber band channel 102 is open on the bottom side. This open bottom side is presented to the top surface of slotted shoe 100 when first alternate housing 92 is engaged into slotted shoe 100 affixed to hypo unit 42.

Slotted shoe 100, which receives slotted foot 98, is attached to hypo unit 42 by being made in one piece with shoe-modified syringe barrel 94 shown in FIG. 6-A.

Referring to FIG. 7-A unless otherwise noted, an alternate slotted shoe 106 is shown that provides a system for attachment of first alternate housing 92 to unmodified typical syringe barrel 46 by inserting hypo unit 42, cap 56 and all, distal end first, through a shoe ring 110 projecting from the bottom side of alternate slotted shoe 106. Alternate slotted shoe 106 is then pulled rearward until a right and a left shoe pawl 108A and 108B surmount and engage upon syringe barrel rim 48.

In both slotted shoe 100 shown in FIG. 6-A and alternate slotted shoe 106 shown in FIG. 7-A, a shoe groove 104 in the top distal portion of the structure provides additional clearance for rubber band 64.

3. The Second Alternate Housing

Second alternate housing 112, which is shown in FIGS. 8-A, 8-B, and 8-C, is in most aspects of design and function the same as housing 66, which is the basic version of the housing component of the invention shown in FIGS. 1-A through 1-L. Except as otherwise noted, all parts and design features of second alternate housing 112 should be assumed to be the same as the parts and design features of the basic version of the housing.

Second alternate housing 112 differs from housing 66 mainly in the method used to secure it to hypo unit 42. Also, the shield component used in conjunction with second alternate housing 112 has a rolling heel 172 instead of a rocking heel 156, which will be discussed below in Subsection D.

Second alternate housing 112 is designed for nonremovable attachment to an ordinary, completely unmodified typical syringe barrel 46. The method of attachment is by way of a circumference ring 118 projecting from the bottom portion of second alternate housing 112, and a pawl 120 integral with and operated by a blade spring 122.

As seen in FIGS. 8-A and 8-C, blade spring 122 is mounted longitudinally along the proximal bottom side of second alternative housing 112. It is situated between the proximal bottom edges of a second alternate right side wall 114A and a second alternate left side wall 114B. Blade spring 122 occupies part of that space which would, in first alternate housing 92 shown in FIG. 6-A, be the open bottom side of first alternate rubber band channel 102.

On the distal bottom side of second alternate housing 112 is a second alternate floor 124 located between the distal bottom edges of second alternate right and left side walls 114A and 114B. At the proximal bottom side of second alternate housing 112, second alternate floor 124 narrows and separates from the walls to become blade spring 122. Pawl 120 is located at the proximal end of blade spring 122.

The forward facing edges of second alternate right and left side walls 114A and 114B, as shown in FIGS. 8-A, 8-B, and 8-C, are somewhat shortened, or blunted off, near the bottom of second alternate housing 112 as compared to the walls of the basic version of the housing. This allows clearance for rolling heel 172 to protrude from the distal end of second alternate housing 112 both to the front and to the sides when the shield component is in a position of containment within second alternate housing 112 prior to deployment.

To mount second alternate housing 112 to hypo unit 42, hypo unit 42 is put distal-end-first into circumference ring 118 while needle 54 is still protected by unremoved cap 56. The second alternate housing 112 is then pulled rearward upon hypo unit 42 until pawl 120 surmounts and engages upon syringe barrel rim 48. A rim stop 126, clearly shown in FIG. 8-B, prevents second alternate housing 112 from being pulled rearward beyond its intended position at the base of typical syringe barrel 46.

Referring to FIG. 8-A unless otherwise noted, it may be seen that the rear bottom portions of second alternate right and left side walls 114A and 114B extend farther rearward than the side walls of the basic version of the housing shown in FIGS. 1-A through 1-L. Formed into the bottom rear edges of second alternate right and left side walls 114A and 114B is a rubber band notch 116 that facilitates rubber band 64 being securely strung around the outside of second alternate housing 112. Unlike the basic version of the housing, second alternate housing 112 has no rubber band peg 80 as is shown connected to housing 66 in FIGS. 1-A through 1-L.

As can be seen from the cutaway view in FIG. 8-C, there is an absence of structural material below and behind the proximal opening of structural cavity 84 to allow for the unobstructed movement of pawl 120.

In FIG. 9-A a variation is seen where a right secondary finger flange 282A and a left secondary finger flange 282B has been attached to a modified circumference ring 284. Also, right and left finger nubs 76A and 76B have been omitted in this variation.

Right and left secondary finger flanges 282A and 282B prevent the barrel of hypo unit 42 from rotating between the operator's forefinger and middle finger. These secondary flanges thus constitute an alternative to right and left finger nubs 76A and 76B as a method of depressing pushrod 128 straight forward without oblique misdirection of thumb force in the direction of typical finger flanges 50.

Secondary flanges similar to right and left secondary finger flanges 282A and 282B can be used in conjunction with any embodiment of the invention, but circumference ring 118 used with second alternate housing 112 provides a particularly convenient attachment point for such secondary flanges.

4. The Third Alternate Housing

Third alternate housing 192, shown in FIG. 10-A, is designed to be affixed to typical low dosage syringe barrel 186 of typical low dosage hypo unit 184. Relative to other hypo units, these low dosage units are small, and therefore third alternate housing 192 is designed to minimize size, weight, and complexity.

Third alternate housing 192 connects to low dosage hypo unit 184 via a clip 194 and a fixed pawl 196. A circumference ring of the type possessed by second alternate housing 192 shown in FIG. 8-A cannot be used, because a typical projecting hub lip 190 projects from typical low dosage needle hub 188 situated at the distal end of typical low dosage hypo unit 184 shown in FIG. 10-A. This projecting lip renders a circumference ring impractical. Furthermore, a syringe barrel of such a low dosage unit is usually of a smaller diameter than the cap placed upon the needle at the distal end of the unit, making insertion of the capped distal end of a low dosage unit into a circumference ring doubly impractical.

Clip 194, made of a semirigid material such as plastic, is a one-piece device with semiflexible open jaws permitting forced lateral insertion of low dosage syringe barrel 186. Clip 194 is simply pushed laterally onto the base of low dosage syringe barrel 186, with fixed pawl 196 going behind the barrel's rim and the proximal end of clip 194 going in front of the barrel's rim. Functioning together, fixed pawl 196 and the proximal end of clip 194 prevent forward or rearward movement of third alternate housing 192.

Though clip 194 and fixed pawl 196 are designed for use with typical low dosage hypo unit 184 as shown in FIG. 10-A, there is no reason why a similar attachment method could not be used to secure other embodiments of the invention to other types of unmodified syringe barrels. Furthermore, there is no reason why other attachment means could not be used to attach other embodiments of the invention to low dosage hypo units.

Third alternate housing 192, depicted in FIG. 10-A, dispenses with the side walls, the rubber band channel, and the structural cavity of the basic version of the housing, but the pushrod channel is retained. Below the proximal opening of the pushrod channel is a third alternate rubber band notch 200 in the rear bottom portion of third alternate housing 192, for placement of a small rubber band 216 strung externally, in the manner employed in conjunction with second alternate housing 112 shown in FIGS. 8-A, 8-B, and 8-C.

Third alternate housing 192 also has a third alternate roof 198 that provides the user with a stable gripping surface and prevents premature rotation of a low dosage shield 202.

Naturally, specific low dosage design features discussed here, such as the lack of housing walls and the lack of a structural cavity to save weight and material, are design options that need not necessarily be incorporated into a low dosage embodiment.

5. The Integral Assembly

The housing portion of the integral assembly 218 depicted in FIGS. 11-A through 11-F is formed by bringing together an integral right wall wing 224A and an integral left wall wing 224B. The unification of these two parts produces a housing structure with a form and function similar to the basic version of the housing component shown in FIGS. 1-A through 1-L, but possessing certain differences.

Referring to FIG. 11-B, it may be seen that right and left wings 224A and 224B are connected to an integral floor 222 by an integral right wall hinge 226A and an integral left wall hinge 226B, respectively. Integral floor 222, in turn, is integrally connected to integral syringe barrel 220.

It may be seen in FIG. 11-C that as the two wings are rotated upon their hinged bottom edges toward one another, an integral fastening dowel 236 engages into an integral fastening hole 240 which runs through left wing 224B and through an integral left fore-end shelf 228B. Fastening dowel 236 projects from an integral spacer 234, which projects in turn from integral right fore-end shelf 228A, which projects from the inside surface of right wing 224A. The tapered, conical shape of an integral fastening crown 238 at the end of dowel 236 permits dowel 236 to be pressed into fastening hole 240 to its full extent, the depth of its entry being controlled and limited by the face of integral spacer 234 coming into contact with the inside surface of left fore-end shelf 228B at the perimeter of fastening hole 240.

Referring to FIG. 11-D, it may be seen that the back surface of fastening crown 238, once it breaches the far rim of fastening hole 240, prevents dowel 236 from thereafter being subsequently withdrawn, thereby preventing the two wings from thereafter coming apart and thus insuring the structural integrity of the housing formed by their union.

Crown 238 and fastening hole 240 permanently mate in the above described manner due to crown 238 having a slightly larger diameter than the inside diameter of fastening hole 240, and due to the parts being composed of a material flexible enough to permit fastening crown 238 to be pressed through fastening hole 240 but resilient enough to prevent crown 238 from being subsequently withdrawn.

As the two wings come together, they bring into position other parts that are made integral with the inside surfaces of the wings, forming the internal structure of the housing.

Still referring to FIG. 11-D unless otherwise noted, it can be seen that an integral right roof 232A and an integral left roof 232B, which project from the inside surfaces of right and left wings 224A and 224B, respectively, abut one another at the top of the assembled housing structure, thereby lending strength and stability to the structure and preventing premature rotation of an integral shield 254 shown clearly in FIGS. 11-A, 11-G, and 11-H. If required, one or more stabilizing dowels and complimentary receiving holes may be placed in integral right roof 232A and integral left roof 232B, respectively, to lend further stability to the housing structure.

Also projecting from the interior surfaces of the wings are integral right and left fore-end shelves 228A and 228B, as shown clearly in FIGS. 11-C and 11-D. Right shelf 228A and left shelf 228B do not project as far from the interior surfaces of the wings as does right roof 232A and left roof 232B, and therefore right shelf 228A and left shelf 228B do not come into contact with one another when the wings are rotated into their locked-together position. Instead, they are separated by a distance controlled and defined by the length of integral spacer 234. When the invention is folded and locked together into its assembled orientation, an integral expansion spring 244 fits into the cavity between right shelf 228A and left shelf 228B.

It can be seen from an examination of FIG. 11-B and 11-D that the dual internal ledges running parallel to the longitudinal axis of integral syringe barrel 220, formed by the proximal parts of right shelf 228A and left shelf 228B, constitute the bottom of the channel through which travels the proximal part of an integral pushrod 260. More specifically, the cross-sectional shape of integral shaft 262 forms a "T," and the cross-bar portion of this "T" is supported by, and slides along, these internal ledges. The top part of the channel through which travels integral shaft 262 is formed by the lowermost surfaces of right roof 232A and left roof 232B.

As FIG. 11-E suggests, after the wings are fastened together, when integral shield 254 is in a position of containment prior to deployment, the obliquely slanting, dual internal ledges formed by the distal parts of right shelf 228A and left shelf 228B, which can be seen spread apart in an overhead perspective in FIG. 11-B, form obliquely sloping surfaces against which the underside of an integral fore-end 266 lays flush.

Projecting from the outside surfaces of right wall wing 224A and left wall wing 224B are right and left finger nubs 76A and 76B, which are identical to the nub projections affixed to the other versions of the housing.

6. Summary of the Most Important Features Shared by All Versions of the Housing Component of the Invention First: The housing component provides a containment structure that insulates the moving parts of the invention from the operator's grip, thereby preventing the operator's fingers from interfering with the deployment of the invention; it also provides a secure gripping surface which enhances the operator's manipulation of the hypo unit during all stages of use, including its primary use of patient injection.

Second: The housing component provides a structural framework that rigidly supports the pushrod channel in a position radially displaced from the surface of the hypo unit.

Third: The housing component provides a convenient structural surface upon which to affix the finger nubs that assist in pushing the radially displaced pushrod in the correct straight-forward direction.

Fourth: The housing component contains a roof portion that insures that the shield component will not rotate or get in the way until it is pushed from the housing component.

Fifth: The housing component provides a convenient structural framework into which to hook, loop, attach, or otherwise moor the proximal end of the rubber band or expansion spring.

Sixth: The housing component possesses the method whereby the contained invention is secured to the hypo unit.

C. Description of the Pushrod

The pushrod component is mountable slidably within a channel supported by the housing component of the invention. It causes the shield component, which is attached to the distal end of the pushrod component, to be pushed forward along the surface of the hypo unit against the tension of a rubber band or other method of resistance in response to manual pressure applied in a forward direction against the pushrod's proximal end.

There are five variations of the pushrod: the basic version; the version equipped with a wedge-shaped stopper; the bendable fulcrum hinge version; the low dosage pushrod version; and the integral pushrod version. Each of these versions is explained below in Subparts 1, 2, 3, 4, and 5. The most important features of the pushrod component of the invention are summarized in Subpart 6.

1. Basic Version of the Pushrod

Pushrod 128, which is the basic version of the pushrod component, is clearly depicted in FIG. 1-E. Pushrod 128 is composed of shaft 130, elbow 132, and fore-end 134.

Pushrod 128, that is, the basic version of the pushrod, can be used in conjunction with housing 66, first alternate housing 92, and second alternate housing 112.

FIG. 1-C shows that shaft 130 is a straight, cross-sectionally square, elongated member. In the exploded view presented in FIG. 1-E, it can be seen that shaft 130 is inserted, proximal-end-first, into the distal opening of pushrod channel 82 during assembly of the various components of the invention. Pushrod 128 is thereafter slidable within pushrod channel 82.

More specifically, pushrod 128 slides forward when thumb or finger pressure applied against the proximal end of shaft 130 in a distal direction overcomes the resistance of rubber band 64. Pushrod 128 slides rearward when such thumb or finger pressure is removed or reduced and rubber band 64 is allowed to rebound.

The square cross-sectional shape of pushrod 128, combined with the complimentary cross-sectional shape of pushrod channel 82, prevents shaft 130 from rotating about its longitudinal axis within pushrod channel 82. Any other out-of-round cross-sectional shape, such as the "T" shaped cross-section of integral shaft 262 shown from the rear in FIG. 11-D, would serve this purpose equally as well.

Shaft 130 is approximately as long as the syringe barrel of the hypo unit with which it functions. The proximal end of shaft 130 terminates in a blunt face suitable for pushing with a thumb or finger. The distal end of shaft 130 rigidly connects to fore-end 134 at an oblique angle. This rigid junction of shaft 130 and fore-end 134 constitutes elbow 132.

Fore-end 134 is a straight, cross-sectionally square, elongated member, having cross-sectional dimensions the same as shaft 130. The proximal end of fore-end 134 terminates at elbow 132. The distal end of fore-end 134 terminates at pintle, or "T" type, fulcrum hinge 144, which connects fore-end 134 to shield 148.

FIG. 2-C shows the components of the pintle, or "T" type, fulcrum hinge prior to assembly. This hinge is composed of a right pintle 136A and a left pintle 136B projecting laterally in opposite directions from one another from the distal end of fore-end 134 in a "T" type configuration. Pintles 136A and 136B engage into a right receiving hole 138A and a left receiving hole 138B which are made into a pair of semicircular hinge plates herein called a right hinge plate 140A and a left hinge plate 140B. Right hinge plate 140A and left hinge plate 140B are mounted parallel to one another upon the back of, and near the proximal end of, rotating spine 150. The distance between hinge plates 140A and 140B equals the width of fore-end 134, excluding the width of pintles 136A and 136B.

To assist in engaging pintles 136A and 136B into receiving holes 138A and 138B, hinge plates 140A and 140B are made of a material such as plastic that contains a certain amount of flexibility and resiliency. As depicted in FIG. 2-C, the distal end of fore-end 134 is placed between hinge plates 140A and 140B, pintles 136A and 136B thus encountering the leading edges of plates 140A and 140B. The leading edges of hinge plates 140A and 140B are sloped somewhat inward so that as pintles 136A and 136B are forced against these leading edges. plates 140A and 140B are forced apart and pintles 136A and 136B can slide between plates 140A and 140B and into receiving holes 138A and 138B. Plates 140A and 140B then spring back to their parallel positions and the hinged connection between fore-end 134 and rotating spine 150 is thus completed. Naturally, any other kind of convenient "pop together" hinge assembly can be used.

When shaft 130 is properly situated in pushrod channel 82 and aligned approximately parallel to the longitudinal axis of hypo unit 42, fore-end 130 slopes obliquely down toward the surface of hypo unit 42 at an angle of about 24 degrees.

As explained in detail below in Subsection C of Section VIII, although shaft 130 and fore-end 134 are essentially rigid, an important feature of both is that they will flex, or bend, slightly during deployment of shield 148, first to allow clearance for rocking heel 156 to pivot during the initial rotation of shield 148, and then to allow rubber band 64 to hold shield 148 against contours of the surface of hypo unit 42 as a shield face 154 slides forward along the surface of hypo unit 42.

2. Wedge-Shaped Stopper Variation of the Pushrod

Wedge-shaped stopper 142, shown in FIG. 5-A, is a wedge-shaped structure which is added onto the proximal portion of shaft 130 and which tapers to its smallest cross-sectional dimension at its proximal end. The distal end of wedge-shaped stopper 142 presents a flat stopping surface facing in the distal direction perpendicular to the longitudinal axis of the pushrod channel 82.

Wedge-shaped stopper 142, affixed to the proximal end of shaft 130, can be forcefully inserted small-end-first into pushrod channel 82 in the proximal direction due to the ability of the material used in the construction of the parts to flex enough to allow entry. But once shaft 130 has been inserted into pushrod channel 82 and the flat face of wedge-shaped stopper 142 has breached the proximal opening of pushrod channel 82, shaft 130 is prevented thereafter from being withdrawn from pushrod channel 82.

The function of permitting shaft 130 entry into but not exit from pushrod channel 82 could also be accomplished by the internal placement in pushrod channel 82 of an upward projecting, rearward angling prong or mechanical finger, together with the placement of a receiving slot or wedge-shaped notch in the bottom side of shaft 130 near its proximal end, whereby the prong would be shoved rearward and down out of the way to permit insertion of shaft 130, but would spring up and catch in the slot to prevent complete subsequent withdrawal of shaft 130 from pushrod channel 82.

The utility of wedge-shaped stopper 142 and structures of like purpose lies in their use in conjunction with a needle trap 168 or an alternate needle trap 170 as depicted in FIGS. 3-A, 3-B, 3-C, 4-A, 4-B, and 4-C, and as discussed below in Subpart 4 of Subsection D.

3. Bendable Fulcrum Hinge Variation of the Pushrod

Pushrod 128 is connected to the shield 148 via pintle, or "T" type, fulcrum hinge 144. In an alternate version, pintle, or "T" type, fulcrum hinge 144 could be replaced by a bendable fulcrum hinge 146 of the type shown in FIG. 3-B, made of plastic or some other flexible material. This would simplify manufacture without compromising operation.

4. Low Dosage Variation of the Pushrod

A low dosage pushrod 208 is used in conjunction with typical low dosage hypo unit 184 shown in FIG. 10-A. Low dosage pushrod 208 has a shorter, smaller, more flexible low dosage fore-end 214 that attaches at a low dosage elbow 212 to a shortened low dosage shaft 210. The shortened, more delicate structure of low dosage pushrod 208 is designed to be more flexible than pushrod 128, thereby permitting the invention to properly operate under the lesser loads generated by small rubber band 216.

5. Integral Variation of the Pushrod

Figure 13:
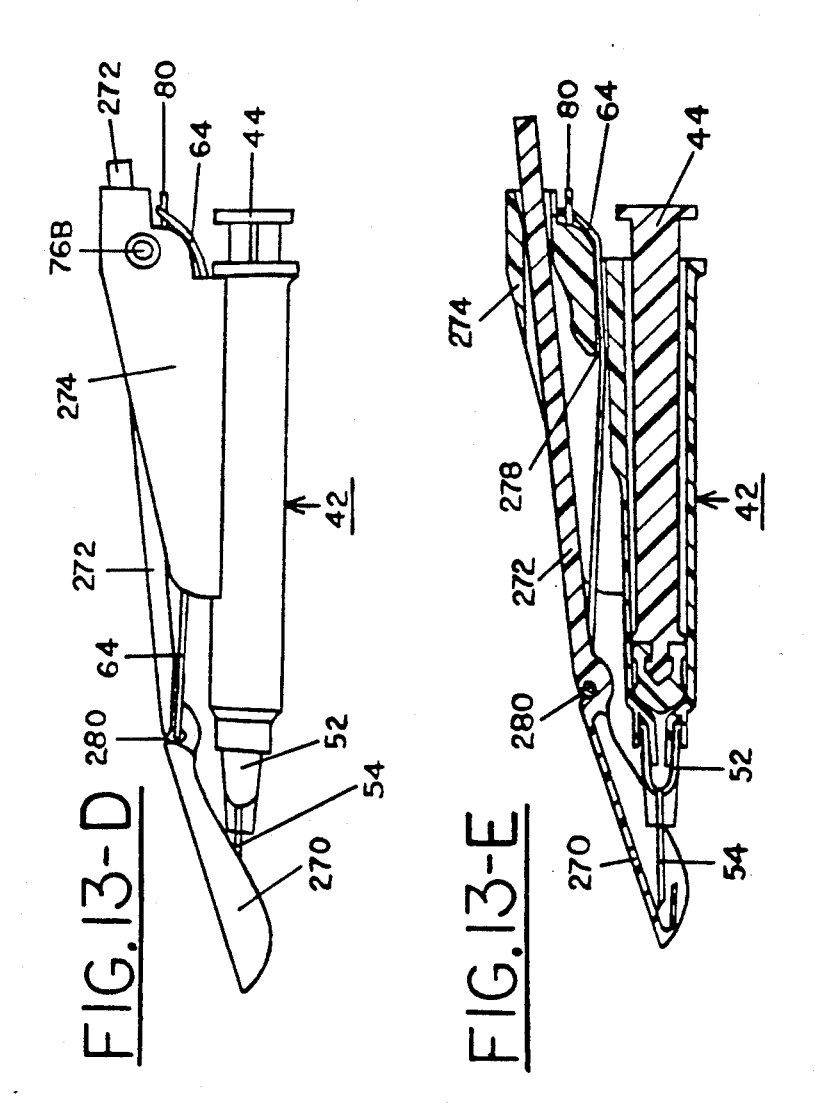

In the design of integral pushrod 260, shown in FIG. 11-A, an integral bendable fulcrum hinge 252, shown clearly in FIGS. 11-A and 11-H, is employed. Integral bendable fulcrum hinge 252 is wider than bendable fulcrum hinge 146 shown in FIG. 13-B, in keeping with wider integral fore-end 266. And integral shaft 262 is also wide; both integral shaft 262 and integral fore-end 266 are the same width as integral shield 254 shown in FIG. 11-B.

Integral shaft 262 also differs from the basic version by having a "T" shaped cross-section, as can be seen from an examination of FIGS. 11-A and 11-D. This "T" shape stiffens integral shaft 262 and also allows it to be more securely held in the channel formed by the union of integral right portion of pushrod channel 230A and integral left portion of pushrod channel 230B, as may be seen from an examination of FIGS. 11-C and 11-D. Integral fore-end 266 does not have a "T" shaped cross-section. Instead, it has a flattened rectangular cross-section, as may be seen from an examination of the profile of integral fore-end 266 depicted in FIG. 11-A. It attaches to integral shaft 262 at about a 24 degree angle at integral elbow 264, as shown in FIG. 11-A 6. Summary of The Most Important Features Shared by all Versions of the Pushrod Component of the Invention First: The pushrod component advances the shield component to the distal end of the hypo unit.

Second: The pushrod component's shaft is radially displaced from the syringe barrel of the hypo unit so that its rearward projecting proximal end does not interfere with the operation of the primary plunger, and so that the method of resistance may pull against its distal end downward as well as rearward.

Third: The pushrod component's correct depression is assisted by finger nubs placed close to its longitudinal axis, or by secondary flanges.

Fourth: The pushrod component has an obliquely slanting distal end that angles down toward the surface of the hypo unit, thereby bringing the point where forward force is applied against the shield component, that is, the fulcrum hinge, close to the surface of the hypo unit, while at the same time allowing the shaft of the pushrod to be positioned radially farther away from the surface of the hypo unit.

D. Description of the Shield

The shield component of the invention is a structure that has an internal region for the containment of the dangerous distal end of a used hypodermic needle projecting from the distal end of a hypo unit. The parts and structure of the basic version of the shield are explained in Subpart 1 below. Alternate versions of certain parts of the basic version of the shield are explained in Subparts 2, 3, 4, 5, and 6. The most important features of the shield component of the invention are summarized in Subpart 7.

1. Basic Version of the Shield

In FIG. 1-E it may be seen that shield 148 is attached to the distal end of fore-end 134 by pintle, or "T" type, fulcrum hinge 144.

Referring unless otherwise noted to the front view in FIG. 2-A, the cutaway side view in FIG. 2-B, and the rear view in FIG. 2-C, it may be seen that rotating spine 150 is a rigid flat elongated rectangular member that forms the backbone of shield 148. A right shield wall 152A and a corresponding left shield wall 152B are integrally connected to rotating spine 150 along the edges of the long sides of rotating spine 150.

Shield walls 152A and 152B are rigid, flat, elongated structures, the two-dimensional shapes of which resemble the shape defined by a chord and an arc. Considered in profile, there are thus basically two edges to each flat wall, a curved edge and a straight edge.

Along the lengths of the straight edges of shield walls 152A and 152B, that is, the edges defined by a chord, the walls are integrally connected, as has been stated, to the edge of each long side of rotating spine 150. Walls 152A and 152B are connected to rotating spine 150 in opposite, parallel, complimentary positions, such that the parallel planes defined by the flat surfaces of walls 152A and 152B are at right angles to the plane defined by the flat back surface of rotating spine 150.

The twin leading edges of the curved sides of walls 152A and 152B, that is, the leading edges defined by an arc, comprise shield-face 154. Shield face 154 "straddles" the cylindrical surface of hypo unit 42 as shield 148 slides forward after rotation during deployment.

As shown in FIG. 1-C, as well as in FIGS. 2-A, 2-B, and 2-C, at the proximal end of rotating spine 150 is rocking heel 156, which is the notched leading edge at the proximal end of rotating spine 150. The notch causes the corners at either end of the notch to project farther proximally than the notched center area between the corners, thereby allowing rocking heel 156 to straddle the cylindrical surface of hypo unit 42 as shield 148 rotates. Additionally, it should be noted that the center portion of the notch which forms rocking heel 156 is deep enough to allow clearance for rubber band 64 within the notch as rocking heel 156 straddles the curved surface of hypo unit 42, provided the angle formed by the length of rotating spine 150 against the surface of hypo unit 42 is about 24 degrees or greater.

Pintle, or "T" type, fulcrum hinge 144 connects fore-end 134 of pushrod 128 to rotating spine 150. "T" type fulcrum hinge 144 is located near the proximal end of rotating spine 150, a short distance distally from rocking heel 156. The distance from rocking heel 156 to fulcrum hinge 144 should be about one-sixth to one-fourth the length of rotating spine 150. The exact distance varies depending on subtle differences in the strengths, dimensions, and positions of all other parts of the invention. This is to say that "T" type fulcrum hinge 144 should be close to rocking heel 156, but still a mechanically significant distance distally from it to enable the mechanically leveraged forces involved in the deployment of shield 148 to operate with optimal result.

Between pintle, or "T" type, fulcrum hinge 144 and rocking heel 156 are a rocking heel right side inlet 158A and a rocking heel left side inlet 158B. These inlets are cutouts made through right and left shield walls 152A and 152B, and into either side of rotating spine 150, as depicted. Rubber band 64 is looped across the back of rotating spine 150 and pulled down into these cutouts, or inlets. Rubber band 64 is then pulled down between the proximal ends of the shield walls, herein referred to as a right shield wall tip 160A and a left shield wall tip 160B, and around into the notch of rocking heel 150.

Referring to FIGS. 2-A and 2-B unless otherwise noted, a needle retaining plate 162 is shown that is a flattened, elongated rectangular member connected at right angles along the edge of each of its two longer sides to right and left shield walls 152A and 152B. Retaining plate 162 is about one third the length of rotating spine 150. The distal end of retaining plate 162 connects to the distal end of rotating spine 150 in such a way as to form a "V" shaped enclosure situated between the parallel shield walls. This "V" shaped enclosure is referred to herein as needle enclosure 164. Needle 54 of hypo unit 42 is safely contained in needle enclosure 164 after deployment of shield 148.

At the distal end of needle enclosure 164, where rotating spine 150 and retaining plate 162 join, the material of which the parts are made is somewhat thickened to form a point barrier 166 that will resist a strong blow or other pressure from pushing the sharp tip of needle 54 through the distal end of deployed shield 148.

2. Rolling Heel Variation of the Shield Component

Rolling heel 172 is a barbell-shaped structural feature clearly shown in FIGS. 4-A and 4-B. It is a part that may be used in place of rocking heel 156 as shown in FIGS. 2-A, 2-B, 2-C, 3-A, and 3-B. As does rocking heel 156, rolling heel 172 serves as an attachment point for tensing rubber band 64 and is the area of the shield component that is urged against the surface of hypo unit 42 as the shield component rotates longitudinally to bring shield face 154 into contact with the surface of hypo unit 42. In conjunction with rolling heel 172, rolling heel right and left side inlets 174A and 174B assume the function of rocking heel right and left side inlets 158A and 158B.

A rolling heel right shield wall 153A, shown in FIG. 8-C, and a rolling heel left shield wall 153B, shown in FIG. 9-A, are used in conjunction with rolling heel 172. These walls are of slightly differing shape from shield walls 152A and 152B because the rolling heel variation does not require right or left shield wall tips 160A and 160B shown in FIG. 3-B. Because the walls used with the rolling heel have a slightly different shape, the face that the leading edges of the walls define has been given distinct designation as a rolling heel shield face 155, which is shown in FIGS. 8-C and 9-A.

The special purpose of rolling heel 172, as compared to rocking heel 156, is that after the pushrod component and shield component have been fully inserted into the housing component during assembly of the invention, rolling heel 172 protrudes beyond the front and the sides of the housing component. This facilitates stringing the rubber band upon the proximal end of the shield component prior to attaching the housing component to the hypo unit, and it ensures the proper operation of rubber band 64 when rubber band 64 or small rubber band 216 is strung around the outside of the housing component of the invention, as is done in the case of second alternate housing 112 and third alternate housing 192.

3. Modified Needle Enclosure Variation of the Shield Component

FIGS. 4-A and 4-B show a modified needle enclosure 176 that possesses added material which forms a narrower, closer-fitting needle containment area that funnels down at its distal end into a tubular space that receives the tip of needle 54. The distal end of this tube-shaped area is closed and thickened to resist penetration. The advantage is that closer fitting modified needle enclosure 176 will more securely retain needle 54, especially in the presence of lateral forces applied against the distal end of hypo unit 42. Also, the narrow tubular enclosure area provides an ideal space in which to place a small amount of viscous disinfectant during manufacture.

The parts that are modified to achieve modified needle enclosure 176 are labeled in FIGS. 4-A and 4-B as modified needle retaining plate 178, modified right and left shield walls 180A and 180B, and modified rotating spine 182. These parts are modified relative to their unmodified corresponding parts only in that they are thickened to create a closer fitting enclosure to receive needle 54 where they join at the distal end of the shield component of the invention.

4. The Needle Trap Variations of the Shield Component

A needle trap 168 is shown in FIGS. 3-A, 3-B, and 3-C, and an alternate needle trap 170 is depicted in FIGS. 4-A, 4-B, and 4-C. Both needle trap 168 and alternate needle trap 170 are inward angling projections connected to the inner surfaces of the walls of the shield component of the invention. These projections are designed to allow needle 54 to enter the shield component but to prevent it from subsequently exiting the shield component. This is their essence: that needle 54 can pass laterally through them in one direction into the interior region of the shield component, but is inhibited from laterally exiting the interior region of the shield component through them in the other direction.

Both trap 168 and alternate trap 170 are designed for use with any and all variations of the shield component of the invention. The purpose of both trap 168 and alternate trap 170 is to further inhibit the needle tip from accidentally breaching needle enclosure 164 or modified needle enclosure 176 after the shield component of the invention has been deployed, especially when the distal end of hypo unit 42 encounters energetic lateral forces directed against shield face 154 or rolling shield face 155 due to accidental lateral collisions when hypo unit 42 is being swung in a fast arch. An additional benefit in some situations is that it also makes the intentional removal of the deployed shield component much more difficult, especially when trap 168 or alternate trap 170 is used in conjunction with wedge-shaped stopper 142, as discussed below.

The traps work by directing accidental lateral forces closer to the base of needle 54 instead of laterally against the tip of needle 54 where they would otherwise be directed due to the tip of needle 54 coming into forceful contact with the distal portion of the inside surface of needle retaining plate 162. If any lateral force is so great that it bends needle 54, needle 54 must bend much farther to exit a shield equipped with trap 168 or alternate trap 170 than a shield not so equipped.

On any embodiment of the invention utilizing rubber band 64 or small rubber band 216 as a method of resistance, needle trap 168 or alternate needle trap 170 can also be used to insure that needle 54 is kept within the shield component of the invention after deployment, even if rubber band 64 or small rubber band 216 for any reason breaks prior to permanent disposal of hypo unit 42.

This purpose is accomplished in conjunction with wedge-shaped stopper 142, which is depicted in FIG. 5-A. wedge-shaped stopper 142 is designed to be optionally affixed to the proximal end of shaft 130 during the manufacturing process. As explained above in Subsection C, Subpart 2, wedge-shaped stopper 142 permits shaft 130 to be slidably inserted into the pushrod channel 82, but prevents the proximal end of shaft 130 from being withdrawn after wedge-shaped stopper 142 is inserted into, and breaches the proximal end of, pushrod channel 82.

Even if rubber band 64 or small rubber band 216 breaks after deployment of the shield component, and shaft 130 is jostled to the maximum forward position permitted by wedge-shaped stopper 142, which would otherwise allow the tip of needle 54 to breach the proximal edge of needle retaining plate 162 or modified needle retaining plate 178, trap 168 or alternate trap 170 will prevent needle 54 from easily exiting the shield component of the invention. This is because the traps permit lateral entry but not lateral exit of needle 54.

In any embodiment of the invention using a plastic spring as a method of resistance, if at any time after deployment of the shield component, the plastic spring for any reason became fully extended, trap 168 or alternate trap 170 would still prevent the needle from easily laterally exiting the interior of the shield component and becoming exposed.

5. The Low Dosage Variation of the Shield Component

Low dosage shield 202, depicted in FIG. 10-A, is designed to be used in conjunction with typical low dosage hypo unit 184. A low dosage shield face 204 has a low dosage lip surmounting ramp 206 designed to assist shield face 204 up and over typical projecting hub lip 190 that projects from typical low dosage needle hub 188 of the type disclosed in U.S. Pat. No. 4,040,421 to Young (1977). Furthermore, the proximal portion of low dosage shield face 204 conforms to the shape presented by the profile of low dosage needle hub 188.

6. The Integral Variation of the Shield Component

Integral shield 254 is depicted in FIGS. 11-A, 11-B, 11-C, 11-E, 11-G, and 11-H.

Referring to FIGS. 11-A, 11-C, and 11-E, it can be seen that in conjunction with integral shield 154, integral expansion spring 244 is used in place of rubber band 64; therefore, there are no side inlets for the purpose of rubber band attachment made into an integral rotating spine 250, integral right and left shield walls 258A and 258B, or integral shield face 256.

As shown in FIGS. 11-C, 11-G, and 11-H, integral expansion spring 244 is connected to the proximal end of integral rotating spine 250 by an integral bendable heel connection 246. This is a flexible connection which is located, as shown in FIG. 11-G, between an integral right rocking heel 248A and an integral left rocking heel 248B. As shown in FIG. 11-H, the integral bendable fulcrum hinge 252 is located about one-fifth the length of integral rotating spine 250 distally from bendable heel connection 246.

Integral shield 254 is connected to the distal end of integral fore-end 266 via integral bendable fulcrum hinge 252 instead of pintle, or "T" type, fulcrum hinge 144 used on many of the other variations of the invention. Integral bendable fulcrum hinge 252 differs from bendable fulcrum hinge 146, as seen in FIG. 3-B, in that the integral version of the bendable hinge is wider to match wider integral shaft 262 and integral fore-end 266.

Connecting all the parts with hinges made of a bendable material allows integral shield 254, along with all the other components of the integral embodiment of the invention, to be molded in one piece, in one operation from one type of material.

7. Summary of the Most Important Features Shared by all Versions of the Shield Component of the Invention First: The shield component is moved forward along the outside surface of the hypo unit by the forward travel of the pushrod against the pull of an expansion spring or rubber band moored closer to the surface of the hypo unit than the pushrod channel, which tends to cause the shield to be urged laterally toward the side of the hypo unit.

Second: The shield component laterally engulfs the needle upon surmounting the distal end of the hypo unit.

Third: The shield component is made secure about the needle by being pulled rearward by the rubber band or other method of resistance upon the release of manually applied forward pressure upon the proximal end of the pushrod component.

Fourth: The shield component is stored in a longitudinally-rotated, inverted position prior to deployment and is rotated about a fulcrum point by being pushed forward at the fulcrum point by the pushrod and being pulled rearward at its proximal end by the expansion spring or rubber band. This rotation brings the distal part of the shield forward and presents the face of the shield to the surface of the hypo unit.

E. Description of the Methods of Resistance

1. The Basic Version of the Method of Resistance

In its basic version, the method of resistance is rubber band 64. In the low dosage variation shown in FIG. 10-A, small rubber band 216 is used.

Rubber band 64, as shown in FIGS. 2-A, 2-B, and 2-C, is hitched to the proximal end of the shield component of the invention by being looped across the back of rotating spine 150, pulled through rocking heel right and left side inlets 158A and 158B, pulled down between right and left shield wall tips 160A and 160B, and pulled around into the notch of rocking heel 156. Rubber band 64 is hitched to rolling heel 172, shown in FIGS. 4-A and 4-B, in the same manner. And small rubber band 216 is hitched to low dosage shield 202 also in the same manner.

After hitching rubber band 64 to the shield component, rubber band 64 is then routed to the proximal end of the housing component. Routing may be through rubber band channel 78 as seen in FIGS. 1-G through 1-L, or laterally through the open bottom of first alternate rubber band channel 102 shown in FIGS. 6-A and 6-B. Routing may also be around the outside of the housing component as is done in conjunction with second alternate housing 112 shown in FIGS. 8-A, 8-B, and 8-C, or third alternate housing 192 shown in FIG. 10-A.

2. The Integral Version of the Method of Resistance

In the integral, one-piece embodiment of the invention, the method of supplying resilient resistance is integral expansion spring 244 seen in FIG. 11-A, which is a molded spring made of plastic or a similar material. Instead of having a spiral configuration as many springs have, in the preferred form integral expansion spring 244 is folded two-dimensionally in a series of plications that diminish in size in the distal direction. Among the benefits of this shape are that it simplifies the spring's manufacture, minimizes its width, and most effectively utilizes the space available for its placement.

Those parts of spring 244 subject to the greatest amount of stress—most notably, each of those sections where spring 244 folds 180 degrees accordion-style back upon itself—should be thickened or otherwise hardened or structurally reinforced. Conversely, spring 244 should become progressively thinner near the center of each of the straight sections. This is done so that when spring 244 is expanded, stress and flection are distributed evenly throughout the material of which spring 244 is composed.

As can be seen in the sectional view presented in FIG. 11-E, before deployment of the shield component, integral expansion spring 244 is designed to occupy a position within the housing component between integral right and left fore-end shelves 228A and 228B, and beneath integral fore end 266 and above integral floor 222.

As shown in FIG. 11-A, integral expansion spring 244 attaches at its distal end to integral rotating spine 250 at integral bendable heel connection 246. As can be seen in FIGS. 11-A and 11-C, the proximal end of integral expansion spring 244 attaches to the proximal end of integral floor 222 at an integral bendable spring mooring point 242.

An important feature of integral expansion spring 244 is that it is not under tension except during the deployment process. Prior to deployment of integral shield 254, integral spring 244 resides within the housing component in a nonstressed state.

Another important feature of integral spring 244 is that partial resiliency of the material from which it is made, as opposed to full resiliency, is all that is required. During the depression and subsequent release of integral pushrod 260 during deployment of integral shield 254, spring 244 must contract after expansion only about a quarter of the distance it has expanded.

It is these operational features of integral spring 244 that allow the integral embodiment of the invention to be made of most types of plastic and other semiresilient materials, and in particular, the same type of material of which typical syringe barrels are made.

Most types of springs made of most types of plastic have two limitations that interfere with their use in many applications. First, plastic springs often fail to adequately perform because they lack the capacity to "remember" and fully return to their original shapes when stored under tension in a flexed position. Second, even when plastic expansion springs are not stored under tension, they have a tendency to be not fully resilient over a wide range of flection; which is to say that when stretched very far, they don't come all the way back. Much of the potential energy generated during the sudden expansion process is not put back into the contraction process, but is instead dissipated through changes in the structure of the plastic at critically stressed points and the generation of minute amounts of heat.

Neither of these limitations of most kinds of plastic interfere with its use in the integral embodiment of this invention.

3. Summary of the Most Important Features of the Rubber Band and Integral Expansion Spring First: The rubber band or spring urges the shield rearward, thereby preventing the shield from accidentally moving forward unassisted prior to intentional deployment; it also pulls the shield rearward about the needle at the concluding phase of the deployment sequence.

Second: The rubber band or spring urges the shield laterally against the side of the hypo unit as the shield moves forward during deployment, and when the shield component surmounts the distal end of the hypo unit, it urges the shield component to laterally engulf the needle.

Third: The rubber band or spring pulls rearward upon the proximal end of the shield as the shield is pushed forward by the pushrod, and in so doing, urges the shield to rotate about the fulcrum hinge.

F. Description of the Preferred Embodiment of the Invention

The preferred embodiment of the invention utilizes hypo unit 42 with shoe-modified syringe barrel 94 in conjunction with first alternate housing 92, such as is shown in FIG. 6-A. Pushrod 128 is attached to the shield component via pintle, or "T" type fulcrum hinge 144, such as is shown disassembled in FIG. 2-C. Shield 148 uses rocking heel 156 such as is shown in FIGS. 2-A, 2-B, and 2-C, rather than rolling heel 172 shown in FIGS. 4-A and 4-B. Needle enclosure 164 as shown in FIG. 2-B is used rather than modified needle enclosure 176 shown in FIG. 4-B. Wedge-shaped stopper 142, shown in FIG. 5-A is not used. Alternate needle trap 170 as shown in FIGS. 4-A, 4-B, and 4-C is used. Rubber band 64 is used as a method of resistance.

G. Description of the Simplified, Non-Rotating Embodiment of the Invention

An additional, simplified, version of the invention is disclosed in FIGS. 13-A through 13-E, wherein a rigid shield 270 is used which does not rotate longitudinally about a fulcrum point during deployment. Instead, it is rigidly joined to a rigid pushrod 272 slidably mounted within a rigid pushrod channel 276.

Rigid pushrod 272 and the other parts used in the non-rotating embodiment of the invention are termed "rigid" to distinguish these parts from their similar counterparts used in the other embodiments, and to emphasize the rigid, non-rotating nature of the connection between the shield component and the pushrod component in this embodiment. The parts are not termed "rigid" because they are in any general way less flexible or resilient than the parts used in the construction of the other embodiments.

To the contrary, the cross-sectional shape of rigid pushrod 272 has the shape of a flattened rectangle precisely to make it slightly more flexible than its cross-sectionally square counterparts. This cross-sectional shape contributes to "up-and-down" flexibility; that is, rigid pushrod 272 has added laterally flexibility within the plane defined generally by the longitudinal axis of hypo unit 42 and the longitudinal axis of rigid pushrod channel 276. Such flexibility allows the path of rigid shield 270 to be less dependent during deployment on the exact path taken by the proximal end of rigid pushrod 272 when rigid pushrod 272 is pushed forward.

This, in turn, causes rigid shield 270 to be more surely and reliably pulled down toward needle 54 during deployment even if the operator's depression of rigid pushrod 272 is badly executed. In other words, even if the operator misdirects the depression of the rigid pushrod 272 in a way that tends to direct rigid shield 270 up, away from the surface of hypo unit 42, the outward "bowing" of rigid pushrod 272 caused by its being pushed forward against the resistance of rubber band 64 will still tend to cause rigid shield 270 to be pulled down to laterally engulf needle 54.

As can be seen in the sectional views shown in FIGS. 13-C and 13-E, rigid pushrod channel 276 widens at the top portion of its proximal end, and also widens at the bottom portion of its distal end, thereby permitting rigid pushrod 272 to rotate longitudinally a few degrees within rigid pushrod channel 276 so as to permit the forward end of rigid pushrod 272, together with attached rigid shield 270, to move laterally toward the longitudinal axis of hypo unit 42 as rigid shield 270 is pushed forward. However, the top distal portion and the bottom proximal portion of rigid pushrod channel 276 prevents rigid pushrod 272 from rotating within rigid pushrod channel 276 in the opposite direction past a parallel position relative to the longitudinal axis of hypo unit 42.

Thus, when rigid pushrod 272 is pushed forward, its distal end may move closer to the surface of hypo unit 42, but not farther away. This feature, along with the aforementioned flexibility built into the length of rigid pushrod 272, helps prevent a misdirected thumb stroke from resulting in an unsuccessful deployment of rigid shield 270.

Unlike the other versions of the shield component, which are stored in an inverted position prior to deployment, rigid shield 270 is stored within a rigid housing 274 facing downward against the surface of hypo unit 42. The proximal end of rubber band 64 is routed through a rigid rubber band channel 278 and secured to rubber band peg 80. At the juncture of rigid shield 270 and rigid pushrod 272, a rigid rubber band notch 280 receives the distal end of rubber band 64. The area of rigid pushrod 272 beneath rigid rubber band notch 280 is reduced in width on either side to give rubber band 64 adequate clearance and prevent it from being pinched between the outside surfaces of the sides of rigid shield 270 and the inside surfaces of the walls of rigid housing 274 when rigid shield 270 is inserted into rigid housing 274.

Prior to deployment, rigid shield 270 is held within rigid housing 274 by the fiction of the outside surfaces of rigid shield 270 and rigid pushrod 272 against the inside surfaces of rigid housing 274. Alternately, a "pop-apart" mechanical coupling could be achieved by a snug complimentary fit of the enlarged distal end of rigid pushrod 272 into the enlarged distal end of rigid pushrod channel 276. Small ridges or nodules placed at the mouth of the distal end of rigid pushrod channel 276 would enhance this pop-apart, mechanical coupling effect and lend a "positive" tactile "feel" to the deployment process.

OPERATION OF THE INVENTION

Three operational phases are involved in using the invention.

First, the four components of the invention must be assembled and secured to the hypo unit.

Second, the invention and the hypo unit to which it is secured must be managed prior to the deployment of the shield in such a way that it enhances rather than interferes with the primary use of the hypo unit.

Third, the shield must be deployed after the needle of the hypo unit has been withdrawn from the patient.

Each phase of operation will be discussed separately below in Subsections A, B, and C. In each subsection, the phase of operation under discussion will pertain first to the basic embodiment of the invention and then an explaination will be given of how certain versions of the various components affect that phase of operation.

A. Assembly of the Invention

1. Assembly of the Basic Version

Referring to FIG. 1-E unless otherwise noted, it may be seen that the distal end of fore-end 134 is connected to the proximal portion of rotating spine 150 via pintle, or "T" type, fulcrum hinge 144. As explained above in Section VII, Subsection C, Subpart 1, and as shown in FIG. 2-C, this hinged connection is accomplished by forcing right and left pintles 136A and 136B between right and left hinge plates 140A and 140B and into right and left receiving holes 138A and 138B.

If bendable fulcrum hinge 146 shown in FIG. 3-B is used, or if integral bendable fulcrum hinge 252 shown in FIG. 11-H is used, the connection is already complete and needs no assembly.

Once shield 148 is hingedly connected to fore-end 134, the shield is rotated back against fore-end 134 so that the back of rotating spine 150 touches and lays flat against the length of fore-end 134. Then rubber band 64 is looped across the back of the proximal end of rotating spine 150 and pulled into rocking heel right and left side inlets 158A and 158B. Rubber band 64 is then pulled down between right and left shield wall tips 160A and 160B of right and left shield walls 152A and 152B, and is then pulled rearward around and into the notch of rocking heel 156, thus securing rubber band 64 to the proximal end of rotating spine 150.

The proximal end of shaft 130 is then inserted a short way into the distal opening of pushrod channel 82.

Rubber band 64 is then pushed or pulled through rubber band channel 78 and moored to the back of housing 66 by looping it around rubber band peg 80. Rubber band 64 may be easily pulled through rubber band channel 78 with the aid of a crocheting hook or similar instrument, or pushed through with a ram rod having a notched forward end.

Shaft 130 is then slid the rest of the way into pushrod channel 82 and the shield is thus drawn into the interior of housing 66 in a rotationally inverted position, completing the assembly of the basic embodiment of the invention. Because housing 66 is molded integral with housing-modified syringe barrel 68, no assembly between the invention and hypo unit 42 is required in the basic embodiment of the invention.

2. Assembly of the First Alternate Housing Version

In the case of first alternate housing 92 shown in FIGS. 6-A and 6-B, shaft 130 is placed part way into pushrod channel 82. Then rotating spine 150 is held against fore-end 134, and rubber band 64 is secured to the proximal end of rotating spine 150 in the same manner as is described above in relation to the basic embodiment of the invention. Then shaft 130 is pulled all the way into pushrod channel 82, thus pulling rotationally-inverted shield 148 all the way into first alternate housing 92. Rubber band 64 is then passed laterally through the open bottom of first alternate rubber band channel 102 and up into the channel proper. Then rubber band 64 is looped around rubber band peg 80 at the back of first alternate housing 102. Then first alternate housing 92 is affixed to hypo unit 42 by placing slotted foot 98 into slotted shoe 100, or into alternate slotted shoe 106 shown in FIG. 7-A.

3. Assembly of the Second Alternate Housing Version

Referring to FIGS. 8-A, 8-B, and 8-C, and FIGS. 4-A and 4-B, in the case of second alternate housing 112, shaft 130 is placed into pushrod channel 82, and the inverted shield component is pushed all the way into second alternate housing 112. Then rubber band 64 is attached to protruding rolling heel 172 by looping rubber band 64 from the bottom up into rolling heel right and left side inlets 174A and 174B. Then rubber band 64 is pulled down and around rolling heel 172 and stretched around the outside of second alternate housing 112 from the bottom up. It is then released, or "dropped," into place in rubber band notch 116.

Then second alternate housing 112 is secured to hypo unit 42 via circumference ring 118 and pawl 120 by putting capped hypo unit 42, cap 56 first, into circumference ring 118 and pulling second alternate housing 112 in the proximal direction to the base of hypo unit 42 until rim stop 126 abuts typical syringe barrel rim 48 and pawl 120 engages upon typical syringe barrel rim 48.

4. Assembly of the Third Alternate Housing Version

Referring to FIG. 10-A, third alternate housing 192 is connected to its respective pushrod and shield components via small rubber band 216 in the same manner as second alternate housing 112 is connected to its pushrod and shield components via rubber band 64.

The assembled unit is then clipped to low dosage hypo unit 184 via clip 194 and fixed pawl 196 by positioning clip 194 against the cylindrical base of low dosage syringe barrel 186 and forcing the jaws of clip 194 onto barrel 186.

5. Assembly of the Integral Version

Referring to FIG. 11-A and 11-E, it can be seen that the integral embodiment is assembled, or in other words, the hingedly connected segments are properly oriented in relation to one another, in a folding operation whereby integral shield 254 is first folded back against integral fore-end 266. Then integral pushrod 260 and integral shield 254 as a unit are folded back against the top side of integral expansion spring 244.

Then integral spring 244, pushrod 260, and shield 254 are folded forward in an arc with integral bendable spring mooring point 242 being the axis of rotation, until the bottom side of integral spring 244 is positioned against integral floor 222. Then integral right wall wing 226A and integral left wall wing 226B are folded up and together and integral fastening crown 238 of integral fastening dowel 236 enters and locks into integral fastening hole 240, securing the wings together, with abutted right roof 232A and left roof 232B stabilizing the assembly and preventing rotation of integral shield 254 prior to deployment.

Integral spacer 234 defines and delimits the space between integral right fore-end shelf 228A and integral left fore-end shelf 228B. Within this delimited space is contained integral spring 244, with the bottom side of integral pushrod 260 to the top of integral spring 244, and integral floor 222 to the bottom of integral spring 244.

6. Assembly of the Simplified, Non-Rotating Embodiment of the Invention

The non-rotating embodiment of the invention is shown in FIGS. 13-A through 13-E. This embodiment is assembled by first routing rubber band 64 through rigid rubber band channel 278 and looping it around rubber band peg 80. Rigid shield 270 is then passed through the loop of rubber band 64 protruding from the distal end of rigid rubber band channel 278. Rubber band 64 is then pulled through the narrow opening of rigid rubber band notch 280. The proximal end of rigid pushrod 272 is then inserted into the distal end of rigid pushrod channel 276. Rigid shield 270 is then pushed all the way into rigid housing 274 and held in place prior to deployment either by friction or by mechanical coupling effect, as explained in Section VII. Subsection G of this specification.

B. Management of the Invention During the Primary Use of the Hypo Unit

1. Management of the Basic Embodiment of the Invention

The basic embodiment of the invention is designed to be packaged fully assembled, connected to the hypo unit, and ready to use. Prior to the deployment of the shield component, the hypo unit equipped with the basic embodiment of the invention is managed very much like a hypo unit not equipped with the invention.

The package is opened, typical cap 56, such as is shown in FIG. 7-A, 8-A and 8-B, is removed, and medicine is drawn into typical fluid chamber 58 such as is shown in FIG. 1-G. If there is a time lapse between loading medicine into the fluid chamber and administering the injection, cap 56 may temporarily be put back on hypo unit 42 until it is time for the injection.

The injection is given in the normal way. During the injection, the "grip" upon hypo unit 42, that is, the finger positions just forward of finger flanges 50 and the thumb position against the proximal end of plunger 44, which parts can be seen in FIG. 1-C, is no different than it would be were the housing component absent. During the injection the housing component is completely out of the way, the bottom rear corner of the housing component being situated just between the tips of the forefinger and middle finger.

After the injection is completed, at the user's option for whatever reason, hypo unit 42 can be handled in one of several ways. It may be recapped with original cap 56 of the type shown in FIG. 7-A. Needle 54 of hypo unit 42, which may be seen in FIG. 1-B, may be placed in a shearing device and sheared off. Hypo unit 42 may be placed uncapped in a puncture resistant container. Or, as typically intended, the invention can be deployed, shielding the tip of the needle. Deployment will be discussed below under "C. Deployment of the Invention."

2. Management of the Embodiment Utilizing the First Alternate Housing

The embodiment using first alternate housing 92, depicted in FIG. 6-A and 6-B, is also designed to be packaged fully assembled, connected to hypo unit 42, and ready to use. However, the advantage of this embodiment is that it gives the user the option of easily removing and discarding the invention upon unpackaging hypo unit 42 prior to giving the injection. At the user's discretion, for whatever the user's perceived good reason, first alternate housing 92, or the proximal portion of shaft 130 projecting rearward from first alternate housing 92, can simply be grasped and pulled rearward, thus removing the invention from slotted shoe 100 affixed to the rear portion of shoe-modified syringe barrel 94.

Because the invention can be discarded at the option of a heath care worker prior to uncapping and using hypo unit 42, this embodiment of the invention cannot be perceived by the user under any circumstances to possess any unavoidable overriding disadvantages or drawbacks. Hospital administrators and other suppliers of hypo units never have to be faced with the problematic choice between providing an unshielded, unsafe product, or alternatively, compelling health care workers to use or to tolerate in an unused condition a device that, in any particular situation for whatever reason, they don't want to use.

The further advantage provided by alternate slotted shoe 106, depicted in FIG. 7-A, is that it permits this embodiment of the invention to be produced using unmodified typical syringe barrel 46 instead of shoe-modified syringe barrel 94, thus avoiding the necessity of in any way modifying current syringe barrel production methods and machinery.

Once the choice has been made to use, instead of remove, the invention from hypo unit 42, the management of the embodiment utilizing first alternate housing 92 is identical to the management of the basic embodiment of the invention, as described above.

3. Management of the Embodiment Utilizing the Integral Assembly

The embodiment utilizing integral assembly 218, as depicted in FIGS. 11-A through 11-H, is also designed to be packaged fully assembled, connected to a fully assembled hypo unit, and ready to use. However, production of this embodiment has the advantage of entailing the lowest variable costs of manufacture after the incurrence of the necessary fixed manufacturing costs. Management of this embodiment is identical to the management of the basic embodiment of the invention, as described above.

4. Management of the Embodiments Utilizing the Second and Third Alternate Housings Two embodiments of the invention which are designed to possibly packaged and marketed without accompanying hypo units in the same package are the embodiments utilizing second alternate housing 112, depicted in FIGS. 8-A, 8-B, and 8-C; and the embodiment utilizing third alternate housing 192, depicted in FIG. 10-A. The packaging of these embodiments could be coordinated with the packaging of the correct size and type of unmodified injection devices to which they are designed to be affixed, through color coding or some other method of easy recognition. Attachment to the injection devices would be on an individual basis or in small quantities as the need arises at some point along the vertical line of distribution after manufacture.

Use of the invention on this basis would be at the discretion of medical personnel or administrators, or according to published government or health-industry safety guidelines, based upon such considerations as the time available for preparation for the injection procedure, the infectious nature of the hospital ward on which the injection devices are to be used; the particular difficulties or dangers surrounding an individual injection, such as the violent disposition of the patient or the chaos of the injection environment; and the special demands of the individuals who are to administer the injections or who are to be exposed to the possibility of harmful contact with infectious medical waste.

In other words, a certain number of shielding units that utilize second and third alternate housings 112 and 192 could be marketed in conjunction with the parallel marketing of a larger number of the typical injection devices to which they could be fitted, to be used as needed or demanded.

After either of these two embodiments of the invention have been attached to freshly unpackaged, still-capped, still-sterile injection devices, the management and use of them does not differ from the management and use of the basic embodiment of the invention, as described above.

5. Management of the Non-Rotating Embodiment

The non-rotating embodiment of the invention is managed the same as the basic embodiment of the invention.

C. Deployment of the Invention

The deployment process will be described with reference to the basic embodiment of the invention, but except where noted, the process does not vary in relation to the other embodiments of the invention. In Subpart 1, the technique of deployment will be explained. In Subpart 2, the mechanical and aspects of deployment will be explained.

1. The Technique of Deployment

After plunger 44 has been depressed, the injection completed, and the needle withdrawn from the patient, the deployment operation is commenced by applying forward directed force against the proximal end of shaft 130.

Depending on the operator's pre-existing grip upon hypo unit 42, this is done using one of three methods.

The first method of applying forward directed force against the proximal end of shaft 130 is as follows: Referring to FIGS. 1-A and 1-C, if the barrel of hypo unit 42 is held between the fore finger and the middle finger, and plunger 44 has been depressed by the thumb, as is the usual situation, after withdrawal of needle 54 from the patient, the thumb may be moved from the proximal end of plunger 44 to the proximal end of shaft 130 without shifting finger grip upon the barrel of hypo unit 42. The thumb then may be brought forward against the proximal end of shaft 130.

As thumb force is exerted, the ends of the operator's fore finger and middle finger pivot slightly rearward upon typical finger flanges 50 which radiate from typical syringe barrel rim 48, bringing the finger tips in contact with right and left finger nubs 76A and 76B. Bracing the finger tips against finger nubs 76A and 76B facilitates the application of thumb force in the forward direction along the longitudinal axis of shaft 130 and also contributes generally to the stability of hypo unit 42 in an operator's hand. The technique of deployment as here described is illustrated in FIG. 1-A.

Pushing shaft 130 forward in the absence of finger nubs 76A and 76B would require bracing the fore finger and the middle finger solely against finger flanges 50, thus causing a tendency for the user to laterally misdirect the thumb stroke applied to the proximal end of shaft 130 at an oblique angle directed toward finger flanges 50 instead of along a straight line forward, especially during the latter stages of the thumb stroke.

Finger nubs 76A and 76B are of great importance in the design and operation of the invention. They allow pushrod 128 to be mounted a convenient radial distance away from longitudinal axis of hypo unit 42 by providing an easily workable method for pushrod 128 to be pushed straight forward despite the lateral displacement.

Removing pushrod 128 radially and linearly from plunger 44, that is, having the line of travel of shaft 128 parallel to but radially distant from the line of travel of plunger 128, and having the proximal end of shaft 128 linearly to the rear of the proximal end of plunger 44, allows plunger 44 to be operated in a conventional manner without accidental, annoying, or otherwise unacceptable interference from a secondary rearward projecting control member. Secondary finger flanges 282A and 282B provide the same result as nubs 76A and 76B, which is a correctly directed thumb stroke and increased stabilization of hypo unit 42 between the operator's fingers, but in a somewhat different manner.

In the embodiment utilizing third alternate housing 192, finger nubs 76A and 76B are less critical because of the extremely light loads and forces involved, but they still do offer some significant assistance in using the apparatus.

The second method of applying forward directed force against the proximal end of shaft 130 is as follows: If the barrel of hypo unit 42 has been held between the thumb on one side, and the middle and ring fingers on the other side during the injection, and plunger 44 has been depressed by the fore finger, the fore finger may be moved from the proximal end of plunger 44 to the proximal end of shaft 130. Then the fore finger can be used to apply a forward directed push to the end of shaft 130 without shifting grip on hypo unit 42.

The third method of applying forward directed force against the proximal end of shaft 130 is as follows: If the barrel of hypo unit 42 has been held between the fore finger, middle finger, and ring finger on one side, and the thumb of the other side during the injection, and plunger 44 has been depressed with the thumb of the other hand, or if hypo unit 42 is withdrawn from the patient using this grip, regardless of how plunger 44 was depressed, the proximal end of shaft 130 may be pushed forward with the thumb of the free hand, or if the other hand is not free, shaft 130 may even be pushed forward by pushing the proximal end of shaft 130 against any available object or surface without changing grip.

The deployment process proceeds the same regardless of the method employed to push shaft 130 forward. This process is illustrated in FIGS. 1-G through 1-L. First, shield 148 is pushed from of housing 66. Then shield 148 rotates with a "clack" sound that transmits tactile and auditory information to the user that the deployment is proceeding properly.

Then shield 148 slides distally along the surface of hypo unit 42, and when retaining plate 162 surmounts the tip of needle 54, needle 54 slaps against the inside surface of rotating spine 150 with a "click" sound that transmits to the user both a sound and a tactile sensation that the deployment is proceeding properly and the pressure against the proximal end of shaft 130 can be released.

When the pressure against the proximal end of shaft 130 is released by the operator's thumb or finger, shaft 130 follows the thumb or finger in the proximal direction a short way until the tip of needle 54 encounters point barrier 166 at the distal end of needle enclosure 164. Further movement of shaft 130 then ceases.

If, for any reason, the deployment would not be successful, shaft 130 would continue to follow the user's thumb or finger in the proximal direction, and would thus convey the information, even to a user who's attention is directed to other tasks instead of being concentrated on the deployment process, that shield 148 has not properly deployed and that needle 54 was not within needle enclosure 164.

The technique of deploying the non-rotating embodiment of the invention differs slightly from the other embodiments in that no rotation of the shield component takes place. Therefore, the operator is deprived of the specific tactile feedback that would otherwise provided by the rotational portion of the deployment.

Also, the depression of rigid pushrod 272 may, in some applications, require a longer "throw," and may also require slightly more emphasis on technique. In specific constructions, if rigid pushrod 272 did not possess the correct amount of flexibility, a more carefully applied line of manual pressure and guidance upon the proximal end of rigid pushrod 272 might be required for reliable operation. The deployment sequence of the non-rotating embodiment can be ascertained from an examination of FIGS. 13-A through 13-E.

2. The Mechanical Process of Deployment a. FIGS. 1-G Through 1-L

The mechanical process of deployment is illustrated in FIGS. 1-G to 1-L, inclusive.

In FIG. 1-G, shield 148 is shown contained within housing 66. When pushrod 128 is pushed forward, it will force shield 148 out of housing 66 and move it toward the distal end of hypo unit 42. The forward moving shield 148 will stretch rubber band 64 or other means of resistance, which in turn exerts a force in the rearward direction upon rocking heel 156.

Because rotating spine 150 is being simultaneously pushed forward at fulcrum hinge 144 and pulled rearward at rocking heel 156, as soon as inverted shield face 154 clears roof 72 of housing 66, rocking heel 156 is brought around in an arc until it lodges against the surface of hypo unit 42. Shield 148 may momentarily slide forward in this position until the increasing loads cause the forward length of advancing pushrod 128 to flex slightly upward away from the surface of hypo unit 42, as illustrated in FIG. 1-H, and permit the distal portion of shield face 154 to continue the rotation that will bring it against the surface of hypo unit 42.

This stage of deployment contributes to the self-alignment of shield 148 because as pushrod 128 flexes, it urges rocking heel 156 down against the convex surface of hypo unit 42, thus aligning the end corners of the concave notch of rocking heel 156 perpendicular to the longitudinal axis of hypo unit 42. Shield 148 will therefore be forced to stay correctly aligned to the surface of hypo unit 42 as it rotates, because of the flection of pushrod 128 as well as the downward pull of rubber band 64.

Requiring that pushrod 128 momentarily flex upward to allow clearance for rocking heel 156 also contributes to an operator's being able to monitor the deployment process through tactile and auditory impressions, because when the loads increase enough to lift pushrod 128 and allow shield 148 to rotate, it "flips" around with enough force to make a small "clack" sound that the user can hear and feel, thus transmitting feedback to the user without the need to visually monitor the deployment process.

Furthermore, requiring that pushrod 128 momentarily rise to allow clearance for rocking heel 156 also enables any particular configuration of the invention to be mounted closer to the surface of hypo unit 42.

As illustrated in FIG. 1-I, when shield 148 rotates and shield face 154 "clacks" against, or comes in contact with, the surface of hypo unit 42, shield 148 will be momentarily blocked from further rotation as it slides forward upon the surface of hypo unit 42. At this point, the capacity of shield face 154 to "straddle" the surface of hypo unit 42 becomes critically important to the extreme reliability of the invention.

Much as a cowboy keeps his perch atop a bucking horse by straddling the animal with his legs while pulling himself centrally toward the steed with his arm, shield 148 is kept correctly perched upon the surface of hypo unit 42 by reason of the twin leading edges of shield face 154 straddling hypo unit 42 while rubber band 64 pulls shield 148 toward hypo unit 42.

As illustrated in FIG. 1-J, when the distal end of shield face 154 slides out onto and engulfs the narrow distal end of hypo unit 42, shield 148 again is permitted to rotate until needle retaining plate 162 encounters the tip of needle 54.

As illustrated in FIG. 1-K, when needle retaining plate 162 surmounts the tip of needle 54, shield 66 will rotate a few more degrees until the inside surface of rotating spine 150 is blocked from further rotation by the tip of needle 54. When the inside surface of rotating spine 150 strikes the tip of needle 54, it makes a "click" that the user can hear and feel, thus helping the user to continue to monitor the deployment process even if his visual attention is directed elsewhere.

As illustrated in FIG. 1-L, when shaft 130 has been fully depressed and needle retaining plate 162 has surmounted the tip of the needle with a "click," the thumb or finger force against the proximal end of shaft 130 is released and rubber band 64 pulls needle enclosure 164 rearward, engulfing the tip of needle 54.

b. Shield Alignment During Deployment

During the deployment process, the nominally parallel orientation of the line of travel of pushrod 128 in relation to the longitudinal axis of hypo unit 42 has some "play" in it. This is because pushrod 128 is slightly flexible, and also because there is a slight amount of "wiggle" between shaft 130 and pushrod channel 82. These factors, rather than contributing to a possible misalignment of shield 148 as it slide forward, actually assists in the proper alignment of shield 148 and makes the deployment process more resistant to failure.

Here is why: The slight flexibility of pushrod 128 and the "play" of pushrod 128 within pushrod channel 82 causes the distance between fulcrum hinge 144 and the longitudinal axis of hypo unit 42 to be variable within a certain range of motion that increases as pushrod 128 advances toward the distal end of hypo unit 42. And rubber band 64, being tethered at its proximal end at a point closer to the surface of hypo unit 42 than the point at which pushrod 128 exits from the distal end of pushrod channel 82, not only tugs against shield 148 in a rearward direction, but also pulls shield 148 laterally, keeping it securely against the surface of hypo unit 42, even when shield 148 is pushed along the irregular contours of the surface at the distal end of hypo unit 42.

Any slight misalignment of pushrod 128 doesn't affect the alignment of shield 148 because the "play" in pushrod 128 allows shield face 154 to seat properly against hypo unit 42 despite potential pushrod 128 misalignment. The forward end of errant pushrod 128 simply flexes, or else pushrod 128 moves slightly within pushrod channel 82, to bring pushrod 128 slightly back into line as rubber band 64 pulls shield face 154 properly and snugly against hypo unit 42.

Thus shield 148 may be said to be self-aligning, because shield face 154 tends to seek its own proper alignment against the surface of hypo unit 42. And because of this tendency toward self-alignment, the proper operation of shield 148 is enhanced rather than inhibited by the slight flexibility of pushrod 128 and the slightly lose fit of pushrod 128 within the pushrod channel 82.

It is this self-aligning effect that makes practical the deployment of a rear-mounted shielding device without the need for any undesirable mechanical connections, additions, or involvement with or to the distal end of the hypodermic needle and syringe apparatus.

c. FIGS. 12-A and 12-B

Refer to FIGS. 12-A and 12-B. FIGS. 12-A and 12-B correspond to, and should be studied in conjunction with, FIGS. 1-H and 1-K, respectively. Assume a two-dimensional model of the invention and the hypo unit, which is an adequate number of dimensions for illustrative purposes because all the significant forces involved in the deployment of the basic embodiment of the invention are manifested within the same plane.

Label the spatial directions as right, left, up, and down. Assume all rotation to be either clockwise or counter-clockwise within the two dimensional plane. Assume hypo unit 42 is oriented generally in a right-left direction, and that the needle at the distal end of hypo unit 42 is pointing left.

Assume the effective mooring point of rubber band 64 to be the proximal end of rubber band channel 78 and define this point as point C. Define the point at which slightly flexible pushrod 128 exits pushrod channel 82 as point D. Define the surface of the syringe barrel of the up side of hypo unit 42 as line segment AB. Define fulcrum hinge 144 as point E, rocking heel 156 as point F, and the point at the distal end of shield 148 as point G. Note that point E is not on line segment FG but rather a slight distance from it. This is because the rotational axis of fulcrum hinge 144 is actually situated above the back of rotating spine 150 rather than being located on it. Define needle 54 as line segment HJ and the tip of needle 54 as point H.

Point D will be farther from line segment AB than will point C. The points C, D, E, and F define the four corners and the four sides of a quadrilateral. If side CD of the quadrilateral remains unchanged in length and remains stationary relative to line segment AB, and side EF remains unchanged in length, then if side DE is forced to lengthen and side CE has a tendency to resist being stretched, angles EFC and FCD will be urged to become larger, and angles FED and EDC will be urged to become smaller.

Urging angle DCF to become larger and urging angle EDC to become smaller will urge the whole quadrilateral, except for the stationary side CD, to swing down. Urging angle EFC to become larger and urging angle FED to become smaller will urge side EF to rotate counter-clockwise relative to side CF.

As side DE lengthens, triangle GEF will rotate counter-clockwise around axis point E relative to expansion-resisting side CF until either angle EFC reaches 180 degrees and point F lies along line CE, or the mechanical advantage of a clockwise force applied to line segment EG equals or exceeds the force urging side EF to rotate counter-clockwise.

The significant mechanical effects are, first, that shield 148 will rotate from an inverted position upon exiting housing 66 and present shield face 154 to the surface of hypo unit 42; second, that shield face 154 will be urged snugly against the surface of hypo unit 42 as shield 148 slides forward; third, that shield 148 will temporarily stop rotating counter-clockwise when the central portion of shield face 154 is urged against the surface of hypo unit 42; fourth, that shield 148 will resume counter-clockwise rotation around the axis of fulcrum hinge 144 a few degrees as shield face 154 negotiates the surface of the distal end of hypo unit 42 and needle retaining plate 162 surmounts the tip of needle 54; and fifth, that when shield 148 is pulled rearward by rubber band 64 after retaining plate 162 has surmounted the tip of needle 54, needle 54 will be contained within needle enclosure 164.

d. The Non-Rotating Embodiment

The mechanical process of deploying the non-rotating embodiment of the invention, shown in FIGS. 13-A through 13-E, differs from the mechanical process of deploying the basic embodiment of the invention in that there is no rotation of the shield component during deployment. But just as in all the other embodiments of the invention, rubber band 64 acts to pull the face of rigid shield 270 laterally against the surface of hypo unit 42 during deployment, as well as urging shield 270 in a rearward direction. In this respect the non-rotating embodiment works according to the same principal as the other embodiments—irrespective of the fact that rigid shield 270 does not rotate about a fulcrum point in a fashion similar to the other versions of the shield component of the invention.

In reference to FIG. 13-E, define the distal end of rigid pushrod channel 276 as point R; the distal end of rigid rubber band channel 278 as point S; and rigid rubber band notch 280 as point T. All together, these points define triangle RST. When side RT, that is, forward advancing rigid pushrod 272, lengthens; and side ST, that is, resisting rubber band 64, urges contraction; then point T, that is, rigid rubber band notch 280 and rigid shield 270 in close proximity thereof, tends to be urged laterally in the direction of the longitudinal axis of hypo unit 42 as well as first forward and then rearward.

RAMIFICATIONS, SCOPE OF INVENTION, AND CONCLUSION

A. Ramifications

The invention disclosed herein enables an operator to shield a hypodermic needle easily and instantaneously with one hand immediately upon withdrawing the needle from the patient, without distracting the operator from the performance of other important medical tasks which may be competing for the operator's immediate time and attention. Prior to deployment, the invention does not in any way impede the injection process.

The invention can be used in conjunction with hypodermic injection products currently being manufactured and marketed, without tampering with any operational features or interfering with any functional aspects of their designs. The invention can be easily and economically produced in a variety of embodiments offering many manufacturing and marketing options. Unlike the recent multitude of other inventions designed to render hypodermic needles safer, this invention is mechanically, economically, and medically suitable and practical to its intended use.

B. Scope of the Invention

While the descriptions and explanations presented herein contain many specificities, these should not be construed as limitations of the scope of the invention but rather as exemplification of several suggested embodiments. Many other variations are possible.

1. Other Embodiments and Variations

For example, in an embodiment using a rubber band strung around the outside of the housing, the rubber band could be moored not between the surface of the hypo unit and the pushrod channel, but near the surface of the hypo unit on the side of the hypo unit opposite the side where the housing is attached. In such an embodiment, the rubber band would be strung to either side of the syringe barrel as well as to either side of the housing. Such a stringing of the rubber band would cause the rubber band to pull the shield with greater force in the downward direction and with less force in the rearward direction.

For another example, the leading edges of the shield walls can be made flexible or hinged so they will flare out somewhat when the shield is pushed from the housing and the shield face encounters the surface of the hypo unit during deployment. This would present a wider shield face to the hypo unit which would better straddle the convex surface of the hypo unit. Widening the shield face would work especially well with syringe barrels of a larger than average diameter.

For another example, the distal end of the pushrod doesn't have to be connected to the fulcrum hinge in all rotating embodiments of the invention. The pushrod could be connected to the rocking heel, the same place where the method of tension is connected. Then, as the pushrod pushes the shield toward the distal end of the hypo unit, the shield, and the distal end of the pushrod, would be urged against the side of the hypo unit, but the shield would not rotate. The shield would only be able to rotate when the as-yet unanchored fulcrum hinge, which is brought forward by the forward movement of the pushrod, is anchored stationary relative to the distal portion of the hypo unit, possibly with a hook engaging upon the forward facing luer lock rim of the syringe barrel. Then, as the pushrod was allowed to retract in a rearward direction, the method of tension would be allowed to pull the proximal end of the shield rearward relative to the newly-anchored fulcrum hinge.

For yet one more example, the rotating spine doesn't have to be one and the same thing as the shield. It could, in some alternative designs, be a separate and distinct structural member from the shield. Such a rotating spine, which could be named a "primary rotating spine," would be constructed and operated as disclosed, with certain differences. It would have no shield side walls or needle enclosure area. A shield of some type would be attached to it in some other way.

One way would be to make the primary rotating spine a flat, rectangular member, without shield side walls, that is hingedly connected to a secondary shield structure at its distal end. The rocking heel of such a primary rotating spine would have a hole instead of a notch through which is strung a rubber band that is strung along the underside length of the primary rotating spine. The distal end of the primary rotating spine would be hingedly connected to a secondary shield of a type similar to what has been previously herein disclosed, complete with a secondary rotating spine.

This secondary shield would have shield side walls, a needle retaining plate, hinge plates to receive pintles made onto the distal end of the primary rotating spine, and a structure similar to a rolling heel upon which to hook the end of the rubber band that was passed through the hole made into the rocking heel at the proximal end of the primary rotating spine. The primary rotating spine would fold back along the fore end in the usual manner previously disclosed herein. The secondary shield would be stored folded back atop the shaft of the pushrod in a completely horizontal, upside-down position within a housing enclosure situated atop the pushrod channel.

Such a configuration would be more complicated than the embodiments previously herein disclosed, but it would have the quality, possibly useful in some applications, of enabling the shield to be deployed by pushing upon a much shortened shaft.

2. Inventive Concepts of the Invention

Although the preceding configurations would be somewhat different in appearance than the other embodiments disclosed herein, they would still operate substantially in conformance with four basic inventive concepts that are melded together to constitute the total invention. These concepts are:

a. First Concept

The first concept is to make a rear-operated pushrod practical by linearly and *radially displacing the pushrod* a convenient operating distance away from the immediate vicinity of the plunger, *and using finger nubs* or *secondary finger flanges* to assist in depressing this radially displaced pushrod in the correct forward direction.

b. Second Concept

The second concept is to use this newly developed pushrod to advance a shield from a relatively proximal position at the base of the hypo unit toward the *unencumbered distal end* of the hypo unit against the pull of a rubber band or other method of resistance that—*be-* cause such resistance is moored at a point lower than the pushrod channel, and within the same general plane as the longitudinal axes of both the hypo unit and the pushrod channel—firmly urges the shield laterally toward and against the side of the hypo unit in addition to pulling upon it in a rearward direction.

This second concept of having the method of resistance moored lower that the pushrod channel, thus pulling the shield downward as well as rearward, is probably the single most important inventive concept behind this invention. Though seemingly simple, it allows for the foolproof and practical deployment of a pushrod-operated shield without attaching any mechanical construction to the distal part of the hypo unit, or otherwise affecting the design, manufacture, or functional use of the distal portion of the hypo unit—something none of the multitude of preceding safety designs have succeeded in accomplishing.

c. Third Concept

The third concept is to use the forward advancing, elongated shield to surmount and *laterally engulf* the needle through an opening designed for the lateral admittance of the needle; then using the method of resistance to *retract the enclosed distal end of the shield rearward* about the needle to complete the shielding process.

d. Fourth Concept

The fourth concept is to use the method of resistance in a secondary capacity to assist in the *longitudinal rotation of a leveraged member about a fulcrum point*. This allows the leveraged member, that is, the rotating spine and any shield assembly connected to it, to be stored "folded back" in an inverted position away from the distal end of the hypo unit prior to deployment. Even when the invention is used in conjunction with comparatively long hypo units, the pushrod can remain short enough to project to the rear of the hypo unit no farther than the correct, optimal distance, while the housing and shield can be kept from encumbering the distal end of the hypo unit.

Using the method of resistance in this secondary capacity also allows the shield to rotate past a parallel position in relation to the longitudinal axis of the shaft of the pushrod, thus allowing the distal end of the shield to "dip down" to engulf the tip of the needle in the latter stages of deployment. The rapid, leveraged rotation of the shield through application of manually applied force also allows the invention to deploy with the proper "snappy" sound and tactile sensation while at the same time permitting the method of resistance to remain unstressed prior to deployment of the invention, as opposed to having any part of the invention stored "cocked" under tension prior to use, and waiting to be "triggered."

It is important to note, however, that even though rotation of the shield about a fulcrum hinge contributes to the overall usability and practicality of the invention, the first three inventive concepts can work without the fourth inventive concept, although probably not as well in most applications.

That is, the shield doesn't have to be made to rotate; it could be rigidly fixed to the end of the pushrod in a fully rotated position. This is how the simplified, non-rotating embodiment of the invention, shown in FIGS. 13-A through 13-E, operates.

In the non-rotating embodiment, the method of resistance still functions to pull the shield, frozen into to a proper angle of engagement in relation to the needle, against the side of the hypo unit as the pushrod is pushed forward against the method of resistance. The method of resistance, being located closer to the longitudinal axis of the hypo unit than the pushrod channel, still causes the shield to laterally engulf the needle when the needle retaining plate surmounts the tip of the needle.

It is true that the lack of a rotating shield does require a longer pushrod in relation to the length of the hypo unit if the shield is to be kept far away from the distal end of the hypo unit prior to deployment, but this does not render the invention completely unworkable or impractical, especially if the invention in this non-rotating form is used in conjunction with a relatively short hypo unit, or one having a relatively short needle.

Conclusion

Therefore, because of the many possible variations upon the basic concepts behind the invention, the scope of the invention should be determined by the appended claims and their legal equivalents rather than the specific embodiments illustrated.

What is claimed is:

1. A shielding device, to be connected to an otherwise ordinary hand-held hypodermic needle and syringe apparatus having a hollow syringe barrel, finger flanges radiating in opposite directions from a rim circumscribing the proximal opening of said syringe barrel, a plunger slidable within and partially projecting rearward from the open proximal end of said syringe barrel, a forward projecting pointed hollow needle, and a means for hermetically joining the proximal end of the lumen of said needle to the distal end of the interior chamber of said syringe barrel, said hand-held hypodermic needle and syringe apparatus being hereinafter referred to as a hypo unit, the improvement being said shielding device, which is intended for connection to said hypo unit, comprising:

a rearward projecting pushrod slidably operable within a pushrod channel secured to said syringe barrel of said hypo unit, the longitudinal axis of said pushrod channel being generally within the same plane as the longitudinal axis of said hypo unit and a greater distance radially from the longitudinal axis of said hypo unit than is the surface of said syringe barrel, the direction of lateral displacement being herein defined as up, and the opposite direction as down;

a shield having an interior region for containment of the distal portion of said needle of said hypo unit, said shield having a proximal end and a distal end, said shield having a shield face on one elongated side, said shield face having a proximal portion and a distal portion, said proximal portion having an opening allowing lateral admission of said needle into the interior of said shield, said distal portion having a barrier preventing the lateral exit of said needle from said shield's interior region;

a connecting means, to connect said shield to the distal portion of said pushrod;

a positioning means, to position said shield face in a generally downward direction toward the surface of said hypo unit, the longitudinal axis of said shield being positioned generally within the same plane as the longitudinal axis of said hypo unit and the longitudinal axis of said pushrod channel, the distal end of said shield being positioned in a generally forward pointing direction;

a resistance means, having a first end connected to said shield, and a second end moored at a mooring point stationary relative to said syringe barrel, said mooring point being to the rear of said first end when said pushrod is extended to a forward position, said mooring point also being a discrete distance below the line defined by the longitudinal axis of said pushrod channel;

an enabling means, enabling the distal portion of said pushrod which extends forward of said pushrod channel to possess enough up and down travel in relation to the longitudinal axis of said hypo unit so that said pushrod does not stop said shield's necessary up and down movement during said shield's deployment;

whereby, when said shield is pushed to the distal end of said hypo unit, said shield laterally engulfs said needle into said shield's interior region through said side opening, and said shield is thereafter retracted by said resistance means to contain the tip of said needle.

2. A shielding device according to claim 1, wherein said resistance means is selected from the group consisting of springs and elastic bands.

3. A shielding device according to claim 1, wherein said enabling means comprises a slight flexibility of said pushrod; whereby the distal portion of said pushrod, with said shield connected thereto, is enabled to move slightly up and down when said pushrod is pushed forward within said pushrod channel.

4. A shielding device according to claim 1, wherein said enabling means comprises a small clearance or free play between said pushrod and the top and bottom inside surfaces of said pushrod channel; whereby the distal portion of said pushrod, with said shield connected thereto, is enabled to move slightly up and down when said pushrod is pushed forward within said pushrod channel.

5. A shielding device for a hypo unit according to claim 1 with a set of two finger nubs, located one to each side of the plane defined by the longitudinal axis of said pushrod channel and the longitudinal axis of said hypo unit, said finger nubs being of a size and shape convenient for purchase of the tips of an operator's forefinger and middle finger, said finger nubs providing such purchase closer to the longitudinal axis of said pushrod channel than the purchase provided by the conventional shape and placement of said finger flanges; whereby said finger nubs facilitate pressing said pushrod squarely and conveniently forward, without a tendency toward oblique misdirection of the pushrod stroke or destabilization of the injection apparatus within the hand, regardless of the distance of said pushrod's radial displacement from the longitudinal axis of said hypo unit, thereby permitting placement of said pushrod a practical distance away from the operating area of said plunger.

6. A shielding device according to claim 1, in which said shield face comprises a pair of leading edges of a pair of side walls forming a portion of said shield, said proximal portion of said shield face and said distal portion of said shield face being situated between said pair of side walls of said shield, said pair of leading edges of said pair of side walls being suitable for straddling and sliding along the convex cylindrical exterior surface of said hypo unit when said shield face is positioned downward against said hypo unit; whereby said pair of leading edges correctly aligns said shield to said hypo unit when said shield is urged against said hypo unit during said shield's deployment to the distal end of said hypo unit.

7. A shielding device according to claim 1, wherein said connecting means and said positioning means are comprised of a rigid joint connecting said shield to the distal portion of said pushrod, said shield face being fixed in a generally downward facing position toward the longitudinal axis of said hypo unit when said pushrod is slidably mounted within said pushrod channel.

8. A shielding device according to claim 1, in which:

said connecting means is comprised of a fulcrum hinge which hingedly joins the distal end of said pushrod to a point connected to said shield a discrete distance from said proximal end of said shield, but closer to said proximal end than to said distal end, and closer to said distal end than the distance from said proximal end to said distal end;

said positioning means is comprised of the application of said first end of said resistance device to said shield at a point nearer to the proximal end of said shield than said fulcrum hinge is to the proximal end of said shield;

said shield is kept, prior to deployment, rotated longitudinally about the axis of said fulcrum hinge in an inverted position with said shield face directed more upward than downward, with said proximal end of said shield being farther forward than said distal end of said shield;

whereby, when said pushrod pushes said shield forward at the point of said fulcrum hinge, and said proximal end of the forward moving shield is pulled rearward by said resistance device, and said shield rotates about said fulcrum hinge, thereby positioning said shield face in a direction generally downward against the surface of said hypo unit, with the distal end of said shield oriented in the forward direction.

9. A shielding device according to claim 1, in which:

said connecting means is comprised of a fulcrum hinge which hingedly joins the distal end of said pushrod to an elongated lever member herein called a rotating spine at a point connected to said rotating spine located a discrete distance from the proximal end of said rotating spine, but closer to said proximal end than to said distal end, and closer to said distal end than the distance from said proximal end to said distal end, with means being provided to connect said rotating spine to said shield;

said positioning means is comprised of the application of said first end of said resistance device to said rotating spine at a point nearer to the proximal end of said rotating spine than said fulcrum hinge is to the proximal end of said rotating spine;

said rotating spine, with said shield connected thereto, is kept, prior to deployment, rotated longitudinally about the axis of said fulcrum hinge with said proximal end of said rotating spine being farther forward than said distal end of said rotating spine;

whereby, when said pushrod pushes said rotating spine forward at the point of said fulcrum hinge, and said distal end of the forward-moving rotating spine is rotated forward by the pull of said resistance device, the means connecting said rotating spine to said shield will position said shield face in a direction generally downward against the surface of said hypo unit, with the distal end of said shield oriented in the forward direction.

10. A shielding device for a hypo unit according to claim 1 in which said pushrod includes a shaft at the proximal end of said pushrod slidable within said pushrod channel, and a fore-end at said pushrod's distal end which turns downward at an elbow point toward the surface of said hypo unit, the downward-turning fore-end being located forward of said pushrod channel; whereby said shaft of said pushrod is enabled to be positioned a greater radial distance away from the surface of said syringe barrel than the distal end of said fore-end of said pushrod.

11. A shielding device for a hypo unit according to claim 1 in which said pushrod channel is structurally supported by a housing connected to the proximal portion of said syringe barrel, said housing having a structurally stable exterior portion suitable for manually gripping and manipulating said hypo unit, said housing having an interior portion suitable for containment of said shield prior to deployment, and said housing having a forward facing opening out of which said shield is pushed by the operation of said pushrod during deployment.

12. A shielding device according to claim 11, where a coupling means is provided to couple and uncouple said housing to and from said syringe barrel; whereby said housing, together with said pushrod channel, said pushrod, and said resistance device, may be secured to said syringe barrel and may thereafter be easily removed from said syringe barrel at the discretion of the operator any time prior to the deployment of said shield.

13. A shielding device according to claim 11, where a coupling means is provided to couple said housing to said syringe barrel in a manner that prevents said housing from thereafter being easily removed; whereby said housing together with said pushrod channel, said pushrod, and said resistance device, may be secured to said syringe barrel and may not thereafter be easily removed by the operator prior to use.

14. A shielding device according to claim 11, where said housing, said pushrod, said shield, and said resistance device are formed as, and comprise, one piece of material, with bendable hinges joining the various segments of the single piece together, said housing being hingedly or bendably divisible into two or more connected sections to facilitate the structural orientation of the bendably joined segments, said housing having fastening means to thereafter fasten said sections of said housing together to form a unified housing structure.

15. A rearward projecting pushrod mechanism for the deployment of a needle shielding device to be used with a hand-held hypodermic needle and syringe medical device of an otherwise ordinary nature having a hollow syringe barrel, finger flanges radiating in opposite directions from a rim circumscribing the proximal opening of said syringe barrel, a plunger slidable within and partially projecting rearward from the open proximal end of said syringe barrel, a forward projecting pointed hollow needle, and a means for hermetically joining the proximal end of the lumen of said needle to the distal end of the interior chamber of said syringe barrel, such hypodermic needle and syringe device being hereinafter called a hypo unit, the improvement being the pushrod mechanism for the deployment of the shielding device, comprising:

a rearward projecting pushrod slidably operable within a pushrod channel secured to said syringe barrel of said hypo unit, the longitudinal axis of said pushrod channel being generally within the same plane as the longitudinal axis of said hypo unit and a greater distance radially from the longitudinal axis of said hypo unit than is the surface of said syringe barrel;

a set of two finger nubs, located one to each side of the plane defined by the longitudinal axis of said pushrod channel and the longitudinal axis of said hypo unit, said finger nubs being of a size and shape convenient for purchase of the tips of an operator's forefinger and middle finger, said finger nubs providing such purchase closer to the longitudinal axis of said pushrod channel than the purchase provided by the conventional shape and placement of said finger flanges;

whereby said finger nubs facilitate pressing said pushrod squarely and conveniently forward, without a tendency toward oblique misdirection of the pushrod stroke or destabilization of the injection apparatus within the hand, regardless of the distance of said pushrod's radial displacement from the longitudinal axis of said hypo unit, thereby permitting placement of said pushrod a practical distance away from the operating area of said plunger.

16. A rearward projecting pushrod mechanism according to claim 15, where said finger nubs are directly connected to said finger flanges, thereby forming two continuous, integral finger purchases located one to each side of the plane defined by the longitudinal axis of said pushrod channel and the longitudinal axis of said hypo unit.

17. A rearward projecting pushrod mechanism according to claim 15, with said pushrod channel being structurally supported by a housing connected to the proximal portion of said syringe barrel, said housing having a structurally stable exterior portion suitable for manually gripping and manipulating said hypo unit, said housing having an interior portion suitable for containment of the pushrod-activated shielding device, said housing having an opening from which said shielding device may be deployed by the operation of said pushrod.

18. A rearward projecting pushrod mechanism according to claim 17 where said housing is connected to said syringe barrel by a foot fitted to the bottom portion of said housing and a shoe fitted to said syringe barrel; whereby said housing may be affixed to said syringe barrel by pushing said foot in a forward direction into said shoe, and said housing may be removed from said syringe barrel by pulling rearward upon said housing or said pushrod while gripping said syringe barrel.

19. A rearward projecting pushrod mechanism according to claim 17, where said housing is connected to said syringe barrel via a circumference ring attached to the bottom portion of said housing and a pawl attached to the rear bottom portion of said housing; whereby said hypo unit, together with any needle cap connected to the distal end thereof, may be pushed distal-end-first into said circumference ring, with said housing being thereafter pulled rearward to the proximal end of said syringe barrel, said pawl surmounting and then engaging behind said rim circumscribing the opening at the proximal end of said syringe barrel.

20. A rearward projecting pushrod mechanism according to claim 17, where said housing is connected to said syringe barrel via a clip attached to the bottom portion of said housing and a fixed pawl attached to the rear bottom portion of said housing, said clip having sides made of a resilient material and a bottom opening between such sides, said sides forming a semicircular inner portion that will accept and cling to the cylindrical base portion of said syringe barrel; whereby said clip will accept the forced lateral insertion of the base of said syringe barrel and thereby secure said housing to said syringe barrel, with said fixed pawl engaging behind said rim circumscribing the proximal opening of said syringe barrel and preventing forward movement of said housing in relation to said syringe barrel.

21. A rearward projecting pushrod mechanism for the deployment of a shielding device to be used with a hand-held hypodermic needle and syringe medical device of an otherwise ordinary nature having a hollow syringe barrel, finger flanges radiating in opposite directions from a rim circumscribing the proximal opening of said syringe barrel, a plunger slidable within and partially projecting rearward from the open proximal end of said syringe barrel, a forward projecting pointed hollow needle, and a means for hermetically joining the proximal end of the lumen of said needle to the distal end of the interior chamber of said syringe barrel, such hypodermic needle and syringe device being hereinafter called a hypo unit, the improvement being the pushrod mechanism for the deployment of said shielding device, comprising:

- a rearward projecting pushrod slidable operable within a pushrod channel secured to said syringe barrel of said hypo unit, the longitudinal axis of said pushrod channel being generally within the same plane as the longitudinal axis of said hypo unit and a greater distance radially from the longitudinal axis of said hypo unit than is the surface of said syringe barrel;
- a set of two secondary finger stops, placed one on each side of said syringe barrel forward of said finger flanges of said syringe barrel of said hypo unit, the distance between each such secondary finger stop from each such finger flange on the same side of said syringe barrel being approximately the width of the distal end of an average adult human finger, said secondary finger stops being of a size and shape sufficient to allow an operator to brace a forefinger on one side of said syringe barrel between one finger flange and one secondary finger stop, and to brace a middle finger of the same hand on the other side of said syringe barrel between the other finger flange and the other secondary finger stop, thereby inhibiting the rotation of said syringe barrel between the grip of the operator's forefinger and middle finger;
- whereby said secondary finger flanges facilitate pressing said pushrod squarely and conveniently forward, without a tendency toward oblique misdirection of the pushrod stroke or destabilization of the injection apparatus within the hand, regardless of the distance of said pushrod's radial displacement from the longitudinal axis of said hypo unit, thereby permitting placement of said pushrod a practical distance away from the operating area of said plunger.

22. A safety assembly, for shielding the used needle tip of a hand-held hypodermic needle and syringe device herein referred to as a hypo unit, said hypo unit including a syringe barrel with a plunger projecting proximally therefrom and slidable therein, and a hypodermic needle projecting distally therefrom, said safety assembly comprising: a shield with an interior region and an opening along one side, said shield being moved forward along the outside surface of said hypo unit by the operation of a pushrod slidable within a channel attached to the proximal portion of said syringe barrel of said hypo unit, said pushrod being pushed forward against a means of tension pulling rearward and downward in an oblique direction which intersects the longitudinal axis of said hypo unit; whereby, when said shield is being pushed toward the distal end of said hypo unit, said shield is urged in the direction of the surface of said hypo unit, and when said shield arrives at the distal portion of said hypo unit, said shield is urged by the pull of said means of tension to laterally engulf said needle into said shield's interior region through said side opening, said shield being thereafter retracted rearward by said means of tension to contain the tip of said needle.

23. A safety shield according to claim 22, wherein said shield is connected to a rotational fulcrum point, said shield prior to deployment being kept rotated longitudinally about said rotational fulcrum point in an inverted position, the distal end of said shield being kept rearward of the proximal end of said shield, said proximal end of said shield being connected to said means of tension, and said rotational fulcrum point being pushed toward the distal portion of said hypo unit by said pushrod during deployment; whereby said shield face is rotated toward said hypo unit when said means of tension pulls said proximal end of said shield rearward relative to said rotational fulcrum point.

* * * * *